US010179808B2

(12) United States Patent
Chi et al.

(10) Patent No.: US 10,179,808 B2
(45) Date of Patent: Jan. 15, 2019

(54) KV1.3 ANTAGONISTS AND METHODS OF USE

(71) Applicant: Janssen Biotech, Inc., Horsham, PA (US)

(72) Inventors: Ellen Chi, San Diego, CA (US);
Wilson Edwards, San Diego, CA (US);
Chichi Huang, Spring House, PA (US);
Wai-Ping Leung, San Diego, CA (US);
Ronald Swanson, San Diego, CA (US);
Alan Wickenden, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 14/163,158

(22) Filed: Jan. 24, 2014

(65) Prior Publication Data

US 2014/0255401 A1 Sep. 11, 2014

Related U.S. Application Data

(60) Provisional application No. 61/757,389, filed on Jan. 28, 2013, provisional application No. 61/756,777, filed on Jan. 25, 2013.

(51) Int. Cl.
*C07K 14/435* (2006.01)
*C07K 14/765* (2006.01)

(52) U.S. Cl.
CPC ...... *C07K 14/43522* (2013.01); *C07K 14/765* (2013.01); *C07K 2319/30* (2013.01); *C07K 2319/31* (2013.01)

(58) Field of Classification Search
CPC ............ C07K 14/43522; C07K 14/765; C07K 2319/31; C07K 2319/30
See application file for complete search history.

(56) References Cited

U.S. PATENT DOCUMENTS

| 8,043,829 | B2 | 10/2011 | Sullivan et al. | |
|---|---|---|---|---|
| 2009/0281028 | A1* | 11/2009 | Sullivan | A61K 47/48215 514/4.8 |
| 2011/0236461 | A1 | 9/2011 | Underhill | |
| 2014/0155325 | A1* | 6/2014 | Mark | A61K 45/06 514/9.5 |

FOREIGN PATENT DOCUMENTS

| JP | 2010-527607 A | 8/2010 |
|---|---|---|
| JP | 2012-521360 A | 9/2012 |
| WO | WO 2006/002850 A2 | 1/2006 |
| WO | WO 2006/042151 A2 | 4/2006 |
| WO | WO 2006/116156 A2 | 11/2006 |
| WO | WO 2008/088422 A2 | 7/2008 |
| WO | WO 2009/075773 A3 | 12/2009 |

OTHER PUBLICATIONS

Abdel-Mottaleb, et al., "OdK2, a Kv1.3 channel-selective toxin from the venom of the Iranian scorpion *Odonthobuthus doriae*," Toxicon, 51: 1424-1430 (2008).
Abdul, et al, "Activity of Potassium Channel-blockers in Breast Cancer," Anticancer Research, 23: 3347-3352 (2003).
Beeton, et al, "Targeting Effector Memory T Cells with a Selective Peptide Inhibitor of Kv1.3 Channels for Therapy of Autoimmune Diseases," Molecular Pharmacology, 67(4): 1369-1381 (2005).
Beeton, et al., "Kv1.3 channels are a therapeutic target for T cell-mediated autoimmune diseases," Proceedings of the National Academy of Science USA, 103(46): 17414-17419 (2006).
Bielanska, et al, "Voltage-Dependent Potassium channels Kv1.3 and Kv1.5 in Human Cancer," Current Cancer Drug Targets, 9:904-914 (2009).
Cahalan, et al, "The functional network of ion channels in T lymphocytes," Immunology Review, 231(1): 59-87 (2009).
Chandy, et al., "K+ channels as targets for specific immunomodulation," Trends in Pharmacological Science, 25(5): 280-289 (2004).
Cheong, et al., "Potent suppression of vascular smooth muscle cell migration and human neointimal hyperplasia by Kv11.3 channel blockers," Cardiovascular Research, 89: 282-289 (2011).
Edwards, et al., "Targeting the Ion channel Kv1.3 with Scorpion Venom Peptides Engineered for Potency, Selectivity, and Half-life," Journal of Biological Chemistry, 289(33): 22704-22714 (2014).
Escoubas, et al., "Venomics as a drug discovery platform," Expert Reviews of Proteomics, 6(3): 221-224 (2009).
Fraser, et al., "Predominant expression of Kv1.3 voltage-gated K+ channel subunit in rat prostate cancer cell lines: electrophysiological, pharmacological and molecular characterization," Pfugers Arch—European Journal of Physiology, 446: 559-571 (2003).
Hyodo, et al., "Voltage-gated potassium channel Kv1.3 blocker as a potential treatment for rate-anti-glomerular basement membrane glomerulonephritis," American Journal of Physiological Renal Physiology, 299: F1258-F1269 (2010).
Khanna, et al., "K+ channels and the microglial respiratory burst," American Journal of Physiology Cell Physiology, 280: C796-C806 (2010).
Glenn F. King, "Venoms as a Platform for human drugs: translating toxins into therapeutics," Expert Opinion on Biological Therapy, 11(11): 1469-1484 (2011).
Koo, et al., "Blockade of the voltage-gated potassium channel Kv1.3 inhibits immune responses in vivo," The Journal of Immunology, 158: 5120-5128 (1997).
Koo, et al., "Correolide and Derivatives Are Novel Immunosuppressants Blocking the Lymphocyte Kv1.3 Potassium Channels," Cellular Immunology, 197: 99-107 (1999).
Mouhat, et al., "K+ channel types targeted by synthetic OSK1, a toxin from *Orthochirus scrobiculosus* scorpion venom," Biochemistry Journal, 385: 95-104 (2005).
Overington, et al., "How many drug targets are there?" Nature Reviews, 5: 993-996 (2006).
Rangaraju, et al., "Kv1.3 potassium channels as a therapeutic target in multiple sclerosis," Expert Opinion on Therapeutic Targets, 13:8: 909-924 (2009).
Read, et al., "Induction of Inflammatory Bowel Disease in Immunodeficient Mice by Depletion of Regulatory T Cells," Current Protocols in Immunology, 15.13.1-15.13.10 (1999).
Ron Swanson, "Engineering Novel Therapeutics Targeting the Ion Channel Kv1.3" 5th Immunotherapeutics & Immunomonitoring Conference, Jan. 31-Feb. 1, 2013 (Powerpoint Presentation).

(Continued)

*Primary Examiner* — Ruixiang Li
(74) *Attorney, Agent, or Firm* — Kirk Baumeister

(57) ABSTRACT

The present invention relates to Kv1.3 antagonists, and polynucleotides encoding them, and methods of making and using the foregoing.

12 Claims, 28 Drawing Sheets
Specification includes a Sequence Listing.

(56) References Cited

OTHER PUBLICATIONS

Tarcha, et al., "Durable Pharmacological Responses from the Peptide ShK-186, a Specific Kv1.3 Channel Inhibitor That Suppresses T Cell Mediators of Autoimmune Disease," The Journal of Pharmacology and Experimental Therapeutics, 342(3): 642-653 (2012).

Tschritter, et al., "A New Variant in the Human Kv1.3 Gene Is Associated with Low Insulin Sensitivity and Impaired Glucose Tolerance," The Journal of Clinical Endocrinology & Metabolism, 91(2): 654-658 (2006).

Wang, et al., "Activated T cells Inhibit Neurogenesis by Releasing Granzyme B: Rescue by Kv1.3 blockers," Journal of Neuroscience, 30(14): 5020-5027 (2010).

Wickenden, et al., "Ion channel drug discovery: challenges and future direction," Future Med. Chemistry, 4(5): 661-679 (2012).

Wulff, et al., "K+ Channel Expression during B Cell Differentiation: Implications for Immunomodulation and Autoimmunity," The Journal of Immunology, 173: 776-786 (2004).

Xu, et al., "The voltage-gated potassium channel Kv1.3 regulates energy homeostasis and body weight," Human Molecular Genetics, 12(5): 551-559 (2003).

Xu, et al., "The voltage-gated potassium channel Kv1.3 regulates peripheral insulin sensitivity," Proceedings of the National Academy of Science, 101(9): 3112-3117 (2004).

NCBI Accession No. 2CK4_A (Oct. 10, 2012).

Han, et al., "Structural Basis of a Potent Peptide Inhibitor Designed for Kv1.3 Channel, a Therapeutic Target of Autoimmune Disease," Journal of Biological Chemistry, 283: 19058-19065 (2008).

* cited by examiner

Figure 1

```
                                          Cys pairs
Odk2    GVPTDVKCRGSEQCIKPCKDAGMRFGKCMNGKCHCTPK
Osk-1   GVIINVKCKISRQCLEPCKKAGMRFGKCMNGKCHCTPK
                       Cys8-Cys28
                       Cys14-Cys33
                       Cys18-Cys35
```

Figure 4A

| Peptide ID/ clone ID | Sequence at amino acid residues | | | | | | | | | | | | | | | | | | | | | | | | | | | | | | | | | | | | | | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | |
| Odk2 | G | V | P | T | D | V | K | C | R | G | S | P | Q | C | I | Q | P | C | K | D | A | G | M | R | F | G | K | C | M | N | G | K | C | H | C | T | P | K | 1 |
| Osk-1 | G | V | I | I | N | V | K | C | K | I | S | R | Q | C | L | E | P | C | K | K | A | G | M | R | F | G | K | C | M | N | G | K | C | H | C | T | P | K | 2 |
| KV1D579 | G | V | P | T | D | V | K | C | R | I | S | R | Q | C | L | K | P | C | K | D | A | G | M | R | F | G | K | C | M | N | G | K | C | H | C | T | P | K | 3 |
| KV1D665 | G | V | P | T | D | V | K | C | R | I | S | R | Q | C | L | K | P | C | K | D | A | G | M | R | F | G | K | C | M | N | G | K | C | D | C | T | P | K | 4 |
| KV1D402 | G | V | P | T | D | V | K | C | R | I | S | R | Q | C | L | K | P | C | K | D | A | G | M | R | F | G | K | C | M | N | G | K | C | H | C | T | P | K | 5 |
| KV1D560 | G | V | P | T | D | V | K | C | R | I | S | A | Q | C | L | K | P | C | K | D | A | G | M | R | F | G | K | C | M | V | G | K | C | H | C | T | P | E | 6 |
| KV1D437 | G | V | P | T | D | V | K | C | R | I | S | R | Q | C | L | K | P | C | K | D | A | G | M | R | F | G | K | C | M | N | G | K | C | H | C | T | P | K | 7 |
| KV1D392 | G | V | P | T | D | V | K | C | R | I | S | R | Q | C | L | K | P | C | K | D | A | G | M | R | F | G | K | C | L | N | G | K | C | H | C | T | P | K | 8 |
| KV1D356 | G | V | P | T | D | V | K | C | R | I | A | R | Q | C | D | K | P | C | K | D | A | G | M | H | F | G | K | C | M | N | G | K | C | H | C | T | P | K | 9 |
| KV1D623 | G | V | P | T | D | V | K | C | R | I | S | R | Q | C | L | K | P | C | K | D | A | G | M | R | F | G | K | C | M | N | G | K | C | H | C | T | P | K | 10 |
| KV1D583 | G | V | P | T | D | V | K | C | R | I | S | R | Q | C | L | K | P | C | E | D | A | G | M | R | F | G | K | C | M | N | G | K | C | H | C | T | P | K | 11 |
| KV1D604 | G | V | P | T | D | V | K | C | E | I | S | R | Q | C | L | K | P | C | K | D | A | G | M | R | F | G | K | C | M | N | G | K | C | H | C | T | P | K | 12 |
| KV1D344 | G | V | P | T | D | V | K | C | R | I | S | R | Q | C | L | K | P | C | K | D | A | G | M | R | F | G | K | C | M | N | G | K | C | H | C | T | P | K | 13 |
| KV1D294 | L | V | P | T | D | V | K | C | R | I | S | R | Q | C | L | K | P | C | K | D | A | G | M | R | F | G | K | C | M | N | G | K | C | H | C | T | P | K | 14 |
| KV1D575 | G | V | P | T | D | V | K | C | A | I | S | R | Q | C | L | K | P | C | K | D | A | G | M | R | F | G | K | C | M | N | G | K | C | H | C | T | P | K | 15 |
| KV1D608 | G | V | P | T | D | V | K | C | R | I | S | R | Q | C | L | K | P | C | K | D | A | G | M | R | F | G | K | C | M | N | G | K | C | H | C | T | P | K | 16 |
| KV1D570 | G | V | P | T | D | V | K | C | R | I | S | R | Q | C | L | K | P | C | K | D | A | G | M | R | F | G | R | C | M | N | G | K | C | H | C | T | P | K | 17 |
| KV1D647 | G | V | P | T | D | V | K | C | R | I | S | R | Q | C | L | K | P | C | K | D | A | G | M | K | F | G | K | C | M | N | G | K | C | H | C | T | P | K | 18 |
| KV1D625 | G | V | P | T | D | V | K | C | R | I | S | R | Q | C | L | K | P | C | K | D | A | G | M | R | F | G | K | C | M | N | G | K | C | H | C | T | P | K | 19 |
| KV1D564 | G | V | P | T | D | V | K | C | R | I | S | R | Q | C | L | K | P | C | K | D | A | G | M | R | F | G | K | C | M | N | G | K | C | H | C | T | P | K | 20 |
| KV1D342 | G | V | P | T | D | V | K | C | R | I | S | R | Q | C | I | E | P | C | K | D | A | G | M | R | F | G | K | C | M | N | G | K | C | H | C | T | P | K | 21 |
| KV1D197 | G | V | P | T | D | V | K | C | R | I | S | R | Q | C | L | K | P | C | K | D | A | G | M | R | F | G | K | C | M | N | G | E | C | H | C | T | P | K | 22 |
| KV1D414 | G | V | P | T | D | V | K | C | R | I | S | P | Q | C | I | E | P | C | K | D | A | G | M | R | F | G | K | C | M | N | G | K | C | H | C | T | P | K | 23 |
| KV1D163 | G | V | P | T | D | V | K | C | K | I | S | R | Q | C | L | K | P | C | K | D | A | G | M | R | F | G | K | C | M | N | G | K | C | H | C | T | P | K | 24 |
| KV1D664 | G | V | P | T | D | V | K | C | R | I | S | R | Q | C | L | K | P | C | K | D | A | G | M | R | F | G | K | C | M | N | G | K | C | V | C | T | P | K | 25 |

Figure 4A (continued)

| | | | | | | | | | | | | | | | | | | | | | | | | | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| KV1D67 | G | V | P | - | D | K | C | R | S | P | Q | C | I | E | P | C | K | D | A | G | M | R | F | G | K | C | M | N | G | K | C | H | C | T | P | K |
| KV1D387 | G | V | P | T | D | K | C | R | S | R | Q | C | L | K | P | C | K | D | A | G | M | R | F | G | K | C | M | N | G | K | C | H | C | T | P | K |
| KV1D293 | H | V | P | T | D | K | C | R | S | R | Q | C | L | K | P | C | K | D | A | G | M | R | F | G | K | C | A | N | G | K | C | H | C | T | P | K |
| KV1D578 | G | V | P | T | D | K | C | R | S | R | Q | C | L | K | P | C | K | D | A | G | M | R | F | G | K | C | M | N | G | K | C | H | C | T | P | K |
| KV1D562 | G | V | P | T | D | K | C | R | S | R | Q | C | L | Q | P | C | K | D | A | G | M | R | F | G | K | C | M | N | G | K | C | H | C | T | P | K |
| KV1D607 | G | V | P | T | D | K | C | R | S | E | Q | C | L | K | P | C | V | D | A | G | M | R | F | G | K | C | M | N | G | K | C | H | C | T | P | K |
| KV1D37 | G | V | P | T | D | K | C | R | S | R | Q | C | L | K | P | C | K | D | A | G | M | R | F | G | K | C | M | N | G | K | C | H | C | T | P | K |
| KV1D338 | G | V | P | T | E | K | C | R | S | R | Q | C | L | L | P | C | K | D | A | G | M | R | F | G | K | C | M | N | G | K | C | H | C | T | P | K |
| KV1D229 | G | V | P | T | N | V | C | K | S | R | Q | C | L | K | P | C | K | D | A | G | M | R | F | G | K | C | A | N | G | K | C | H | C | T | P | K |
| KV1D203 | G | V | P | T | D | K | C | R | S | P | P | C | Q | L | P | C | K | D | A | G | M | R | F | G | K | C | M | N | G | K | C | H | C | T | P | K |
| KV1D179 | G | V | P | - | D | K | C | K | S | R | Q | C | L | E | P | C | K | D | A | G | M | R | F | G | K | C | M | N | G | K | C | H | C | T | P | L |
| KV1D439 | G | V | P | T | D | K | C | R | S | R | Q | C | L | E | P | C | K | D | A | G | M | R | F | G | K | C | M | N | G | K | C | H | C | T | P | K |
| KV1D580 | G | V | P | T | D | K | C | R | S | R | Q | C | H | K | P | C | K | D | A | G | M | R | F | G | K | C | M | N | G | K | C | H | C | T | P | K |
| KV1D589 | G | V | P | T | D | K | C | R | S | R | Q | C | L | E | P | C | K | D | A | G | M | R | F | G | K | C | M | N | G | K | C | H | C | T | P | K |
| KV1D660 | G | V | P | T | D | K | C | R | S | R | Q | C | L | L | P | C | K | D | A | G | M | R | F | G | K | C | M | N | G | K | C | H | C | T | P | K |
| KV1D296 | V | V | P | T | D | K | C | R | S | R | Q | C | L | L | P | C | K | D | A | G | M | R | F | G | K | C | M | N | G | K | C | H | C | T | P | K |
| KV1D261 | G | V | P | - | N | V | C | R | S | P | Q | C | L | Q | P | C | Q | D | A | G | M | R | F | G | K | C | M | N | G | K | C | H | C | T | P | K |
| KV1D159 | G | V | P | T | N | V | C | K | S | R | Q | C | L | Q | P | C | K | D | A | G | M | R | F | G | K | C | M | N | G | K | C | H | C | T | P | K |
| KV1D133 | G | V | P | I | D | K | C | R | S | P | Q | C | L | Q | P | C | K | D | A | G | M | R | F | G | K | C | M | N | G | K | C | H | C | T | P | K |
| KV1D161 | G | V | P | - | D | K | C | R | S | R | Q | C | L | L | P | C | K | D | A | G | M | R | F | G | K | C | M | N | G | K | C | H | C | T | P | K |
| KV1D69 | G | V | P | - | D | K | C | R | S | R | Q | C | L | L | P | C | K | D | A | D | M | R | F | G | K | C | M | N | G | K | C | H | C | T | P | K |
| KV1D603 | G | V | P | T | D | K | C | R | S | R | Q | C | L | K | P | C | K | D | A | G | M | R | F | G | K | C | M | N | G | K | C | H | C | T | P | K |
| KV1D556 | G | V | P | T | D | K | C | R | S | R | Q | C | L | K | P | C | K | D | A | G | M | R | F | G | K | C | M | N | G | K | C | H | C | T | P | K |
| KV1D591 | G | V | P | T | D | K | C | R | S | R | Q | C | L | D | P | C | K | D | A | G | M | R | F | G | K | C | M | N | G | K | C | H | C | T | P | K |
| KV1D597 | G | V | P | T | D | K | C | R | S | R | Q | C | L | K | P | C | K | D | A | G | M | R | F | G | K | C | M | N | G | K | C | H | C | T | P | K |
| KV1D590 | G | V | P | T | D | K | C | R | S | R | Q | C | L | V | P | C | K | D | A | G | M | R | F | G | K | C | M | N | G | K | C | H | C | T | P | K |
| KV1D551 | D | V | P | T | D | K | C | R | S | R | Q | C | L | K | P | L | K | D | A | G | M | R | F | G | K | C | M | N | G | K | C | H | C | T | P | K |
| KV1D619 | G | V | P | T | D | K | C | R | S | R | Q | C | L | K | P | C | K | D | A | G | M | R | F | G | K | C | M | N | G | K | C | H | C | T | P | K |
| KV1D291 | Q | V | P | I | D | K | C | R | S | P | Q | C | L | E | P | C | K | D | A | G | M | R | F | G | K | C | M | N | G | K | C | H | C | T | P | K |
| KV1D258 | G | V | P | - | N | V | C | K | G | S | P | C | - | E | P | C | K | D | A | G | M | R | F | G | K | C | M | N | G | K | C | H | C | T | P | K |

Figure 4A (continued)

| ID | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 |
|---|---|---|---|---|---|---|---|---|---|---|---|---|---|---|---|---|---|---|---|---|---|---|---|---|---|---|---|---|---|---|---|
| KV1D618 | G | V | P | T | D | V | K | C | R | S | Q | C | L | K | P | C | K | D | A | G | M | R | F | G | K | C | M | N | G | K | C |
| KV1D337 | V | P | T | D | V | Q | C | R | S | R | Q | C | L | K | P | C | K | D | A | G | M | R | F | G | K | C | M | N | G | K | C |
| KV1D430 | G | V | P | T | D | V | K | C | R | S | R | C | L | K | P | C | K | D | A | G | M | R | F | G | K | C | M | N | G | K | C |
| KV1D343 | G | V | P | T | D | V | K | C | R | S | Q | C | L | K | P | C | K | D | A | G | M | R | F | G | K | C | M | N | G | K | C |
| KV1D656 | G | V | P | T | D | V | K | C | Q | S | R | C | L | K | P | C | K | D | A | G | M | R | F | G | K | C | M | N | G | K | C |
| KV1D335 | G | V | P | T | D | V | K | C | R | S | R | C | L | K | P | C | K | D | A | G | M | R | F | G | K | C | M | N | D | G | K | C |
| KV1D438 | G | V | P | T | D | A | C | R | S | R | Q | C | L | K | P | C | K | D | A | G | M | R | F | G | K | C | M | N | G | K | C | H |
| KV1D225 | G | V | P | T | N | V | K | C | R | S | R | Q | C | L | K | P | C | K | D | A | G | M | R | F | G | K | C | M | N | G | K | C |
| KV1D657 | G | V | P | T | D | V | K | C | R | S | R | Q | C | L | K | P | C | K | D | A | G | M | R | F | G | K | C | M | N | G | K |
| KV1D582 | G | V | P | T | D | V | K | C | R | S | R | Q | C | V | K | P | C | K | D | A | G | M | R | F | G | K | C | M | N | G | H |
| KV1D413 | G | V | P | T | D | V | K | C | R | S | R | Q | C | L | K | P | C | K | D | A | G | M | R | F | G | K | C | M | N | G | K |
| KV1D415 | G | V | P | T | D | A | K | C | R | S | R | Q | C | L | K | P | C | K | D | A | G | M | R | F | G | K | C | M | N | G | K |
| KV1D328 | G | V | P | T | D | V | K | C | R | S | R | Q | C | I | K | P | C | K | D | A | G | M | R | F | G | K | C | M | N | G | K |
| KV1D193 | G | V | P | I | D | V | K | C | R | S | R | P | C | I | Q | E | P | C | K | D | A | G | M | R | F | G | K | C | M | N | G | K |
| KV1A1_1E02 | G | V | P | T | D | V | K | C | K | S | R | P | C | I | Q | E | P | C | K | D | A | G | M | R | F | G | K | C | M | N | G | K |
| KV1D255 | G | V | I | T | N | V | K | C | K | S | P | P | C | I | Q | E | P | C | K | D | A | G | M | R | F | G | K | C | M | N | G | K |
| KV1D51 | G | V | P | T | D | V | K | C | K | S | R | P | C | I | Q | E | P | C | K | D | A | G | M | R | F | G | K | C | M | N | G | K |
| KV1D259 | G | V | I | N | V | K | C | K | S | R | P | C | I | L | K | P | C | K | D | A | G | M | R | F | G | K | C | M | N | G | K | C |
| KV1D340 | G | V | P | T | D | V | K | C | L | S | R | Q | C | L | K | P | C | K | D | A | G | M | R | F | G | K | C | M | N | G | K |
| KV1D433 | G | V | P | T | D | V | K | C | R | S | R | C | L | K | P | C | K | D | A | G | M | R | F | G | K | C | M | N | G | K | C |
| KV1D581 | G | V | P | T | D | V | K | C | R | S | R | C | L | K | P | C | K | D | A | G | M | R | F | G | K | C | M | N | G | K | C |
| KV1D372 | G | V | P | Q | D | V | K | C | R | S | R | C | L | K | P | C | K | D | A | R | M | R | F | G | K | C | M | N | G | K | C |
| KV1D314 | G | V | P | T | D | V | K | C | R | S | P | P | C | L | E | E | P | C | K | D | A | E | M | R | F | G | K | C | M | N | G | K |
| KV1D374 | G | V | P | T | D | V | K | C | R | S | P | P | C | L | E | E | P | C | K | D | A | H | M | R | F | G | K | C | M | N | G | K |
| KV1D375 | G | V | P | T | D | V | K | C | R | S | P | C | L | K | P | C | K | D | A | G | M | R | F | G | K | C | M | N | G | K | C |
| KV1D576 | G | V | P | T | D | V | K | C | R | S | R | C | A | K | P | C | K | D | A | G | M | R | F | G | K | C | M | N | G | K | C |
| KV1D587 | G | V | P | T | D | V | K | C | R | S | R | C | L | E | P | C | K | D | A | G | M | R | F | G | K | C | M | N | G | K |
| KV1D33 | G | V | P | T | N | V | K | C | R | S | R | C | I | Q | P | C | K | D | A | G | M | R | F | G | K | C | M | N | G | K | C |
| KV1D269 | G | V | P | T | N | V | K | C | R | S | R | C | L | E | P | C | K | D | A | G | M | R | F | G | K | C | M | N | G | K |
| KV1D101 | G | V | P | T | D | V | K | C | R | S | R | C | I | K | P | C | K | D | A | G | M | R | F | G | K | C | M | N | G | K |
| KV1LA1_2C09 | G | V | I | D | V | K | C | R | G | S | R | C | I | K | P | C | K | D | A | G | M | R | F | G | K | C | M | N | G | K | C | N |

Figure 4A (continued)

| | | | | | | | | | | | | | | | | | | | | | | | | |
|---|---|---|---|---|---|---|---|---|---|---|---|---|---|---|---|---|---|---|---|---|---|---|---|---|
| | | | | | | | | | | | | | | | | | | | | 87 | | | | |
| KV1D99 | G | V | P | T | N | V | K | C | R | I | S | P | Q | C | I | E | P | C | K | D | A | G | M | R | F | G | K | C | M | N | G | K | C | H | C | T | P | K | 87 |
| KV1LA1_1G01 | G | V | P | T | N | V | K | C | K | I | S | P | Q | C | I | E | P | C | K | A | G | M | R | F | G | K | C | M | N | G | K | C | H | C | T | P | K | | 88 |
| KV1LA1_3F10 | G | V | P | T | D | V | K | C | R | I | S | P | Q | C | I | Q | P | C | K | D | A | G | M | R | F | G | K | C | M | N | G | K | C | H | C | T | P | K | | 89 |
| KV1D289 | A | V | P | T | N | V | K | C | R | I | S | P | R | C | L | E | P | C | K | D | A | G | M | R | F | G | K | C | M | N | G | K | C | H | C | T | P | K | | 90 |
| KV1D586 | G | V | P | T | D | V | K | C | R | I | S | R | R | C | L | Q | P | C | K | D | A | G | M | R | F | G | K | C | M | N | G | K | C | H | C | T | P | K | | 91 |
| KV1D311 | G | V | V | P | D | V | K | C | R | I | S | R | R | C | L | K | P | C | K | D | A | G | M | R | F | G | K | C | M | N | G | K | C | H | C | T | P | K | | 92 |
| KV1D436 | G | V | P | T | D | V | K | C | R | I | S | R | R | C | L | K | P | C | K | D | A | G | M | R | F | G | K | C | M | N | G | K | C | H | C | T | P | Q | | 93 |
| KV1D406 | G | V | P | T | D | V | K | C | R | I | S | R | R | C | I | K | P | C | K | D | A | G | M | R | F | G | K | C | M | N | E | K | C | H | C | T | P | K | | 94 |
| KV1D315 | G | V | P | E | D | V | K | C | R | I | S | R | R | C | L | Q | P | C | K | K | A | G | M | R | F | G | K | C | M | N | G | K | C | H | C | T | P | K | | 95 |
| KV1D265 | G | V | P | N | V | K | C | K | I | S | R | R | C | I | Q | P | C | K | K | A | G | M | R | F | G | K | C | M | N | G | K | C | H | C | T | P | K | | | 96 |
| KV1D233 | G | V | P | T | N | V | K | C | R | I | S | R | R | C | L | Q | P | C | K | K | A | G | M | R | F | G | K | C | M | N | G | K | C | H | C | T | P | K | | 97 |
| KV1D237 | G | V | P | T | N | V | K | C | R | I | S | R | R | C | I | E | P | C | K | D | A | G | M | R | F | G | K | C | M | N | G | K | C | H | C | T | P | K | | 98 |
| KV1D141 | G | V | P | T | N | V | K | C | R | I | S | R | R | C | I | E | P | C | K | A | A | G | M | R | F | G | K | C | M | N | G | K | C | H | C | T | P | K | | 99 |
| KV1D129 | G | V | P | T | N | V | K | C | R | I | S | R | R | C | I | E | P | C | K | D | A | G | M | R | F | G | K | C | M | N | G | K | C | H | C | T | P | K | | 100 |
| KV1D77 | G | V | P | T | D | V | K | C | R | I | S | R | R | C | I | Q | P | C | K | D | A | G | M | R | F | G | K | C | M | N | G | K | C | H | C | T | P | K | | 101 |
| KV1D97 | G | V | P | T | I | V | K | C | R | I | S | R | R | C | I | E | P | C | K | D | A | G | M | R | F | G | K | C | M | N | G | K | C | H | C | T | P | K | | 102 |
| KV1D257 | G | V | P | T | N | V | K | C | K | I | S | R | R | C | I | Q | P | C | K | D | A | G | M | R | F | G | K | C | M | N | G | K | C | H | C | T | P | K | | 103 |
| KV1D245 | G | V | P | T | N | V | K | C | R | I | S | R | R | C | I | Q | P | C | K | D | A | G | M | R | F | G | K | C | M | N | G | K | C | H | C | T | P | K | | 104 |
| KV1D173 | G | V | P | T | D | V | K | C | K | I | S | R | R | C | I | E | P | C | K | K | A | G | M | R | F | G | K | C | M | N | G | K | C | H | C | T | P | K | | 105 |
| KV1D63 | G | V | P | T | D | V | K | C | R | I | S | P | R | C | L | H | P | C | K | D | A | Q | M | R | F | G | K | C | M | N | G | K | C | H | C | T | P | K | | 106 |
| KV1D588 | G | V | P | T | D | V | K | C | R | I | S | R | R | C | L | K | P | C | K | D | A | G | M | R | F | G | K | C | M | N | G | K | C | H | C | T | P | K | | 107 |
| KV1D365 | G | V | P | T | D | V | K | C | R | I | S | R | R | C | L | K | P | C | K | D | A | G | M | R | F | G | K | C | M | N | G | K | C | H | C | T | P | K | | 108 |
| KV1D384 | G | V | P | T | D | V | K | C | R | I | S | R | R | C | L | K | P | C | K | D | A | G | L | R | F | G | K | C | M | N | G | K | C | H | C | T | P | K | | 109 |
| | | | | | | | | | | | | | | | | | | | | | | | | | | | | | | | | | | | | | | | 110 |

*Ratio of Kv1.3 %Binding/Kv1.1 %Binding

Figure 4B

| Peptide ID/ clone ID | SEQ ID NO: | Library origin | Kv1.3 %Binding (of KV1C2) | Kv1.1 %Binding (of KV1C2) | Binding Selectivity* | Thallium flux IC$_{50}$ (nM) |
|---|---|---|---|---|---|---|
| Odk2 | 1 | | | | | |
| Osk-1 | 2 | | | | | |
| KV1D579 | 3 | KV1D26L1 | 319.5 | 4.1 | 77.6 | 0.458 |
| KV1D665 | 4 | KV1D26L1 | 151.8 | 8.2 | 18.5 | 0.227 |
| KV1D402 | 5 | KV1D26L1 | 226.1 | 29.0 | 7.8 | 2.178 |
| KV1D560 | 6 | KV1D26L1 | 379.0 | 55.9 | 6.8 | 0.995 |
| KV1D437 | 7 | KV1D26L1 | 232.3 | 36.5 | 6.4 | 1.054 |
| KV1D392 | 8 | KV1D26L1 | 359.2 | 59.4 | 6.1 | 1.067 |
| KV1D356 | 9 | KV1D26L1 | 418.0 | 77.9 | 5.4 | 0.332 |
| KV1D623 | 10 | KV1D26L1 | 88.7 | 17.2 | 5.2 | 2.404 |
| KV1D583 | 11 | KV1D26L1 | 245.1 | 51.7 | 4.7 | 1.014 |
| KV1D604 | 12 | KV1D26L1 | 213.6 | 48.9 | 4.4 | 1.384 |
| KV1D344 | 13 | KV1D26L1 | 199.5 | 47.3 | 4.2 | 1.837 |
| KV1D294 | 14 | KV1D26L1 | 358.5 | 86.6 | 4.1 | 0.116 |
| KV1D575 | 15 | KV1D26L1 | 364.2 | 93.3 | 3.9 | 0.385 |
| KV1D608 | 16 | KV1D26L1 | 200.0 | 54.3 | 3.7 | 0.404 |
| KV1D570 | 17 | KV1D26L1 | 321.9 | 95.3 | 3.4 | 0.533 |
| KV1D647 | 18 | KV1D26L1 | 83.2 | 27.0 | 3.1 | 0.948 |
| KV1D625 | 19 | KV1D26L1 | 190.8 | 62.8 | 3.0 | 0.197 |
| KV1D564 | 20 | KV1D26L1 | 235.2 | 77.8 | 3.0 | 1.374 |
| KV1D342 | 21 | KV1D26L1 | 263.1 | 87.7 | 3.0 | 0.634 |
| KV1D197 | 22 | KV1C2L1 | 162.7 | 55.7 | 2.9 | #N/A |
| KV1D414 | 23 | KV1D26L1 | 362.8 | 129.5 | 2.8 | 0.791 |
| KV1D163 | 24 | KV1C2L1 | 81.7 | 28.7 | 2.8 | #N/A |
| KV1D664 | 25 | KV1D26L1 | 386.5 | 140.3 | 2.8 | 0.110 |
| KV1D67 | 26 | KV1C2L1 | 118.0 | 47.0 | 2.5 | #N/A |
| KV1D387 | 27 | KV1D26L1 | 245.5 | 98.6 | 2.5 | 1.042 |
| KV1D293 | 28 | KV1D26L1 | 332.6 | 136.0 | 2.4 | 0.238 |
| KV1D578 | 29 | KV1D26L1 | 300.5 | 126.7 | 2.4 | 0.181 |
| KV1D562 | 30 | KV1D26L1 | 180.6 | 78.1 | 2.3 | 0.927 |
| KV1D607 | 31 | KV1D26L1 | 404.9 | 182.2 | 2.2 | 0.802 |
| KV1D37 | 32 | KV1C2L1 | 174.5 | 80.7 | 2.2 | #N/A |
| KV1D338 | 33 | KV1D26L1 | 274.5 | 125.4 | 2.2 | 0.618 |
| KV1D229 | 34 | KV1C2L1 | 171.3 | 82.7 | 2.1 | #N/A |
| KV1D203 | 35 | KV1C2L1 | 131.5 | 63.6 | 2.1 | #N/A |
| KV1D179 | 36 | KV1C2L1 | 113.0 | 53.2 | 2.1 | #N/A |
| KV1D439 | 37 | KV1D26L1 | 393.5 | 187.7 | 2.1 | 0.271 |
| KV1D580 | 38 | KV1D26L1 | 411.1 | 202.3 | 2.0 | 0.450 |
| KV1D589 | 39 | KV1D26L1 | 443.9 | 222.0 | 2.0 | 0.214 |
| KV1D660 | 40 | KV1D26L1 | 375.6 | 194.7 | 1.9 | 0.113 |
| KV1D296 | 41 | KV1D26 | 322.2 | 168.5 | 1.9 | 0.106 |
| KV1D261 | 42 | KV1C2L1 | 150.9 | 78.5 | 1.9 | #N/A |
| KV1D159 | 43 | KV1C2L1 | 121.5 | 65.1 | 1.9 | #N/A |
| KV1D133 | 44 | KV1C2L1 | 194.9 | 108.4 | 1.8 | #N/A |

Figure 4B (continued)

| | | | | | | |
|---|---|---|---|---|---|---|
| KV1D161 | 45 | KV1C2L1 | 179.9 | 98.3 | 1.8 | #N/A |
| KV1D69 | 46 | KV1C2L1 | 161.2 | 88.2 | 1.8 | #N/A |
| KV1D603 | 47 | KV1D26L1 | 280.2 | 157.7 | 1.8 | 0.224 |
| KV1D556 | 48 | KV1D26L1 | 253.0 | 144.6 | 1.7 | 1.102 |
| KV1D591 | 49 | KV1D26L1 | 258.2 | 148.0 | 1.7 | 0.982 |
| KV1D597 | 50 | KV1D26L1 | 293.5 | 170.0 | 1.7 | 0.141 |
| KV1D590 | 51 | KV1D26L1 | 428.9 | 249.3 | 1.7 | 0.139 |
| KV1D551 | 52 | KV1D26L1 | 228.1 | 132.7 | 1.7 | 0.202 |
| KV1D619 | 53 | KV1D26L1 | 219.6 | 128.7 | 1.7 | 0.568 |
| KV1D291 | 54 | KV1D26L1 | 271.2 | 159.1 | 1.7 | 0.091 |
| KV1D258 | 55 | KV1C2L1 | 98.2 | 57.7 | 1.7 | #N/A |
| KV1D618 | 56 | KV1D26L1 | 431.9 | 258.6 | 1.7 | 0.622 |
| KV1D337 | 57 | KV1D26L1 | 373.0 | 225.5 | 1.7 | 0.334 |
| KV1D430 | 58 | KV1D26L1 | 396.6 | 241.2 | 1.6 | 0.698 |
| KV1D343 | 59 | KV1D26L1 | 209.0 | 128.3 | 1.6 | 0.332 |
| KV1D656 | 60 | KV1D26L1 | 258.1 | 158.5 | 1.6 | 0.314 |
| KV1D335 | 61 | KV1D26L1 | 338.3 | 207.9 | 1.6 | 0.325 |
| KV1D438 | 62 | KV1D26L1 | 358.1 | 223.0 | 1.6 | 0.650 |
| KV1D225 | 63 | KV1C2L1 | 191.7 | 121.3 | 1.6 | #N/A |
| KV1D657 | 64 | KV1D26L1 | 122.6 | 78.1 | 1.6 | 0.469 |
| KV1D582 | 65 | KV1D26L1 | 261.0 | 166.2 | 1.6 | 0.632 |
| KV1D413 | 66 | KV1D26L1 | 371.4 | 240.1 | 1.5 | 0.693 |
| KV1D415 | 67 | KV1D26L1 | 444.9 | 293.1 | 1.5 | 0.873 |
| KV1D328 | 68 | KV1D26L1 | 351.1 | 231.8 | 1.5 | 0.151 |
| KV1D193 | 69 | KV1C2L1 | 168.1 | 111.8 | 1.5 | #N/A |
| KV1LA1_1E02 | 70 | KV1C2L1 | 153.9 | 100.6 | 1.5 | #N/A |
| KV1D255 | 71 | KV1C2L1 | 151.6 | 103.8 | 1.5 | #N/A |
| KV1D51 | 72 | KV1C2L1 | 109.8 | 74.9 | 1.5 | #N/A |
| KV1D259 | 73 | KV1C2L1 | 108.3 | 73.1 | 1.5 | #N/A |
| KV1D340 | 74 | KV1D26L1 | 406.8 | 274.3 | 1.5 | 0.536 |
| KV1D433 | 75 | KV1D26L1 | 384.9 | 260.5 | 1.5 | 0.516 |
| KV1D581 | 76 | KV1D26L1 | 208.4 | 141.8 | 1.5 | 0.116 |
| KV1D372 | 77 | KV1D26L1 | 328.1 | 224.2 | 1.5 | 0.213 |
| KV1D314 | 78 | KV1D26L1 | 377.0 | 260.3 | 1.4 | 0.108 |
| KV1D374 | 79 | KV1D26L1 | 357.4 | 247.3 | 1.4 | 0.240 |
| KV1D375 | 80 | KV1D26L1 | 383.8 | 267.8 | 1.4 | 0.139 |
| KV1D576 | 81 | KV1D26L1 | 179.9 | 125.8 | 1.4 | 0.159 |
| KV1D587 | 82 | KV1D26L1 | 275.3 | 193.7 | 1.4 | 0.662 |
| KV1D33 | 83 | KV1C2L1 | 194.3 | 140.5 | 1.4 | #N/A |
| KV1D269 | 84 | KV1C2L1 | 192.5 | 133.3 | 1.4 | #N/A |
| KV1D101 | 85 | KV1C2L1 | 167.4 | 116.4 | 1.4 | #N/A |
| KV1LA1_2C09 | 86 | KV1C2L1 | 150.4 | 111.0 | 1.4 | #N/A |
| KV1D99 | 87 | KV1C2L1 | 142.6 | 99.0 | 1.4 | #N/A |
| KV1LA1_1G01 | 88 | KV1C2L1 | 134.8 | 95.7 | 1.4 | #N/A |
| KV1D31 | 89 | KV1C2L1 | 128.2 | 94.4 | 1.4 | #N/A |
| KV1LA1_3F10 | 90 | KV1C2L1 | 110.6 | 77.2 | 1.4 | #N/A |

Figure 4B (continued)

| | | | | | | |
|---|---|---|---|---|---|---|
| KV1D289 | 91 | KV1D26L1 | 338.1 | 243.7 | 1.4 | 0.103 |
| KV1D586 | 92 | KV1D26L1 | 291.6 | 210.6 | 1.4 | 0.251 |
| KV1D311 | 93 | KV1D26L1 | 393.2 | 287.8 | 1.4 | 0.130 |
| KV1D436 | 94 | KV1D26L1 | 343.0 | 252.9 | 1.4 | 0.512 |
| KV1D406 | 95 | KV1D26L1 | 426.9 | 319.0 | 1.3 | 0.671 |
| KV1D315 | 96 | KV1D26L1 | 339.2 | 255.4 | 1.3 | 0.094 |
| KV1D265 | 97 | KV1C2L1 | 246.1 | 195.1 | 1.3 | #N/A |
| KV1D233 | 98 | KV1C2L1 | 246.0 | 194.4 | 1.3 | #N/A |
| KV1D237 | 99 | KV1C2L1 | 208.2 | 158.7 | 1.3 | #N/A |
| KV1D141 | 100 | KV1C2L1 | 204.4 | 161.1 | 1.3 | #N/A |
| KV1D129 | 101 | KV1C2L1 | 197.6 | 150.6 | 1.3 | #N/A |
| KV1D77 | 102 | KV1C2L1 | 195.5 | 150.0 | 1.3 | #N/A |
| KV1D97 | 103 | KV1C2L1 | 193.5 | 154.4 | 1.3 | #N/A |
| KV1D257 | 104 | KV1C2L1 | 189.0 | 141.5 | 1.3 | #N/A |
| KV1D245 | 105 | KV1C2L1 | 175.2 | 131.5 | 1.3 | #N/A |
| KV1D173 | 106 | KV1C2L1 | 164.5 | 131.1 | 1.3 | #N/A |
| KV1D63 | 107 | KV1C2L1 | 113.1 | 90.4 | 1.3 | #N/A |
| KV1D588 | 108 | KV1D26L1 | 438.7 | 337.8 | 1.3 | 0.536 |
| KV1D365 | 109 | KV1D26L1 | 456.8 | 352.0 | 1.3 | 0.326 |
| KV1D384 | 110 | KV1D26L1 | 449.1 | 356.9 | 1.3 | 0.536 |

*ratio Kv1.3 %Binding/Kv1.1 %Binding
N/A: not done

Figure 6

| Protein | % Binding* | Thallium flux IC$_{50}$ (nM) | C-terminal extension | | Extended peptide | |
|---|---|---|---|---|---|---|
| | | | Amino acid sequence | SEQ ID NO: | Amino acid sequence | SEQ ID NO: |
| KV1D819L1_55F01 | 367.0% | 0.776 | HAAG | 123 | GVPINVKCKISRQCIEPCKDAGMRFGKCMNGKCHCTPKHAAG | 269 |
| KV1D819L1_94C07 | 153.6% | 3.273 | RRPT | 124 | GVPINVKCKISRQCIEPCKDAGMRFGKCMNGKCHCTPKRRPT | 270 |
| KV1D819L1_94D07 | 132.8% | 5.559 | ASKP | 125 | GVPINVKCKISRQCIEPCKDAGMRFGKCMNGKCHCTPKASKP | 271 |
| KV1D819L1_74F03 | 128.5% | 4.677 | PKPQ | 126 | GVPINVKCKISRQCIEPCKDAGMRFGKCMNGKCHCTPKPKPQ | 272 |
| KV1D819L1_67B04 | 124.5% | 11.614 | QDQT | 127 | GVPINVKCKISRQCIEPCKDAGMRFGKCMNGKCHCTPKQDQT | 273 |
| KV1D819L1_92E05 | 122.1% | 3.508 | AHRP | 128 | GVPINVKCKISRQCIEPCKDAGMRFGKCMNGKCHCTPKAHRP | 274 |
| KV1D819L1_62A05 | 121.5% | 7.079 | QPTH | 129 | GVPINVKCKISRQCIEPCKDAGMRFGKCMNGKCHCTPKQPTH | 275 |
| KV1D819L1_62A06 | 121.1% | 8.511 | REQT | 130 | GVPINVKCKISRQCIEPCKDAGMRFGKCMNGKCHCTPKREQT | 276 |
| KV1D819L1_53C04 | 120.8% | 2.851 | PPKP | 131 | GVPINVKCKISRQCIEPCKDAGMRFGKCMNGKCHCTPKPPKP | 277 |
| KV1D819L1_67D09 | 120.7% | 8.710 | KQGA | 132 | GVPINVKCKISRQCIEPCKDAGMRFGKCMNGKCHCTPKKQGA | 278 |
| KV1D819L1_68D08 | 119.4% | 3.467 | TRPA | 133 | GVPINVKCKISRQCIEPCKDAGMRFGKCMNGKCHCTPKTRPA | 279 |
| KV1D819L1_63A05 | 119.4% | 3.273 | APHK | 134 | GVPINVKCKISRQCIEPCKDAGMRFGKCMNGKCHCTPKAPHK | 280 |
| KV1D819L1_62A07 | 119.2% | 7.674 | RTEH | 135 | GVPINVKCKISRQCIEPCKDAGMRFGKCMNGKCHCTPKRTEH | 281 |
| KV1D819L1_67C09 | 118.4% | 6.383 | PTHT | 136 | GVPINVKCKISRQCIEPCKDAGMRFGKCMNGKCHCTPKPTHT | 282 |
| KV1D819L1_61A03 | 115.4% | 4.416 | RAEK | 137 | GVPINVKCKISRQCIEPCKDAGMRFGKCMNGKCHCTPKRAEK | 283 |
| KV1D819L1_67C04 | 113.4% | 5.754 | PAPA | 138 | GVPINVKCKISRQCIEPCKDAGMRFGKCMNGKCHCTPKPAPA | 284 |
| KV1D819L1_4B09 | 112.8% | | SHRP | 139 | GVPINVKCKISRQCIEPCKDAGMRFGKCMNGKCHCTPKSHRP | 285 |
| KV1D819L1_4B09 | 112.8% | | SHRP | 140 | GVPINVKCKISRQCIEPCKDAGMRFGKCMNGKCHCTPKSHRP | 286 |
| KV1D819L1_70A08 | 110.9% | 5.821 | PPTR | 141 | GVPINVKCKISRQCIEPCKDAGMRFGKCMNGKCHCTPKPPTR | 287 |
| KV1D819L1_70B02 | 110.7% | 1.603 | HHTT | 142 | GVPINVKCKISRQCIEPCKDAGMRFGKCMNGKCHCTPKHHTT | 288 |
| KV1D819L1_70B11 | 110.6% | 4.677 | HRPA | 143 | GVPINVKCKISRQCIEPCKDAGMRFGKCMNGKCHCTPKHRPA | 289 |
| KV1D819L1_74F06 | 109.9% | 6.457 | KAHP | 144 | GVPINVKCKISRQCIEPCKDAGMRFGKCMNGKCHCTPKKAHP | 290 |
| KV1D819L1_74D02 | 108.8% | 7.161 | QTTQ | 145 | GVPINVKCKISRQCIEPCKDAGMRFGKCMNGKCHCTPKQTTQ | 291 |

Figure 6 (continued)

| | | | | | |
|---|---|---|---|---|---|
| KV1D819L1_51C08 | 108.8% | 4.217 | PTPT | 146 | GVPINVKCKISRQCIEPCKDAGMRFGKCMNGKCHCTPKPTPT | 292 |
| KV1D819L1_70C06 | 108.0% | 4.786 | TQAP | 147 | GVPINVKCKISRQCIEPCKDAGMRFGKCMNGKCHCTPKTQAP | 293 |
| KV1D819L1_13E06 | 106.4% | 1.660 | RKPH | 148 | GVPINVKCKISRQCIEPCKDAGMRFGKCMNGKCHCTPKRKPH | 294 |
| KV1D819L1_53C07 | 106.4% | 0.473 | HTPP | 149 | GVPINVKCKISRQCIEPCKDAGMRFGKCMNGKCHCTPKHTPP | 295 |
| KV1D819L1_69B03 | 105.9% | 8.222 | TKPP | 150 | GVPINVKCKISRQCIEPCKDAGMRFGKCMNGKCHCTPKTKPP | 296 |
| KV1D819L1_71F11 | 105.4% | 1.549 | PRPT | 151 | GVPINVKCKISRQCIEPCKDAGMRFGKCMNGKCHCTPKPRPT | 297 |
| KV1D819L1_74G05 | 105.3% | 6.607 | KQTA | 152 | GVPINVKCKISRQCIEPCKDAGMRFGKCMNGKCHCTPKKQTA | 298 |
| KV1D819L1_51C06 | 105.2% | 5.012 | PHTP | 153 | GVPINVKCKISRQCIEPCKDAGMRFGKCMNGKCHCTPKPHTP | 299 |
| KV1D819L1_62A09 | 105.1% | 6.683 | HTPP | 154 | GVPINVKCKISRQCIEPCKDAGMRFGKCMNGKCHCTPKHTPP | 300 |
| KV1D819L1_94D05 | 105.0% | 0.380 | HAKP | 155 | GVPINVKCKISRQCIEPCKDAGMRFGKCMNGKCHCTPKHAKP | 301 |
| KV1D819L1_38H08 | 104.9% | | TRRP | 156 | GVPINVKCKISRQCIEPCKDAGMRFGKCMNGKCHCTPKTRRP | 302 |
| KV1D819L1_45B11 | 103.7% | 6.237 | PTTP | 157 | GVPINVKCKISRQCIEPCKDAGMRFGKCMNGKCHCTPKPTTP | 303 |
| KV1D819L1_63C05 | 103.3% | 3.802 | RQHA | 158 | GVPINVKCKISRQCIEPCKDAGMRFGKCMNGKCHCTPKRQHA | 304 |
| KV1D819L1_61D11 | 102.6% | 1.660 | PTRP | 159 | GVPINVKCKISRQCIEPCKDAGMRFGKCMNGKCHCTPKPTRP | 305 |
| KV1D819L1_61C05 | 102.3% | 5.309 | PAPH | 160 | GVPINVKCKISRQCIEPCKDAGMRFGKCMNGKCHCTPKPAPH | 306 |
| KV1D819L1_74B07 | 102.2% | 6.457 | ADKP | 161 | GVPINVKCKISRQCIEPCKDAGMRFGKCMNGKCHCTPKADKP | 307 |
| KV1D819L1_61B08 | 102.2% | 2.483 | PHHQ | 162 | GVPINVKCKISRQCIEPCKDAGMRFGKCMNGKCHCTPKPHHQ | 308 |
| KV1D819L1_35E07 | 102.1% | 5.495 | GRRT | 163 | GVPINVKCKISRQCIEPCKDAGMRFGKCMNGKCHCTPKGRRT | 309 |
| KV1D819L1_62B05 | 101.8% | 5.495 | RPDA | 164 | GVPINVKCKISRQCIEPCKDAGMRFGKCMNGKCHCTPKRPDA | 310 |
| KV1D819L1_74E02 | 101.7% | 2.065 | NHRP | 165 | GVPINVKCKISRQCIEPCKDAGMRFGKCMNGKCHCTPKNHRP | 311 |
| KV1D819L1_70B04 | 101.1% | 4.732 | NHQG | 166 | GVPINVKCKISRQCIEPCKDAGMRFGKCMNGKCHCTPKNHQG | 312 |
| KV1D819L1_51C04 | 100.9% | 6.095 | TAPP | 167 | GVPINVKCKISRQCIEPCKDAGMRFGKCMNGKCHCTPKTAPP | 313 |
| KV1D819L1_51A08 | 100.8% | 6.457 | RHPH | 168 | GVPINVKCKISRQCIEPCKDAGMRFGKCMNGKCHCTPKRHPH | 314 |
| KV1D819L1_51B11 | 100.3% | 3.162 | PSRP | 169 | GVPINVKCKISRQCIEPCKDAGMRFGKCMNGKCHCTPKPSRP | 315 |
| KV1D819L1_68A08 | 99.5% | 4.786 | PQHQ | 170 | GVPINVKCKISRQCIEPCKDAGMRFGKCMNGKCHCTPKPQHQ | 316 |
| KV1D819L1_70D07 | 99.1% | 2.512 | PTQH | 171 | GVPINVKCKISRQCIEPCKDAGMRFGKCMNGKCHCTPKPTQH | 317 |
| KV1D819L1_74F07 | 99.0% | 4.624 | HTKP | 172 | GVPINVKCKISRQCIEPCKDAGMRFGKCMNGKCHCTPKHTKP | 318 |
| KV1D819L1_7F10 | 98.8% | | RKKP | 173 | GVPINVKCKISRQCIEPCKDAGMRFGKCMNGKCHCTPKRKKP | 319 |

Figure 6 (continued)

| ID | % | | 4-letter | # | Sequence | # |
|---|---|---|---|---|---|---|
| KV1D819L1_13A02 | 98.4% | 4.169 | HNRP | 174 | GVPINVKCKISRQCIEPCKDAGMRFGKCMNGKCHCHCTPKHNRP | 320 |
| KV1D819L1_62E06 | 98.3% | 6.026 | PEKP | 175 | GVPINVKCKISRQCIEPCKDAGMRFGKCMNGKCHCHCTPKPEKP | 321 |
| KV1D819L1_74A08 | 98.3% | 6.237 | RAQT | 176 | GVPINVKCKISRQCIEPCKDAGMRFGKCMNGKCHCHCTPKRAQT | 322 |
| KV1D819L1_51E05 | 97.7% | 4.842 | PAAT | 177 | GVPINVKCKISRQCIEPCKDAGMRFGKCMNGKCHCHCTPKPAAT | 323 |
| KV1D819L1_62A02 | 97.6% | 10.000 | RTEQ | 178 | GVPINVKCKISRQCIEPCKDAGMRFGKCMNGKCHCHCTPKRTEQ | 324 |
| KV1D819L1_68C11 | 97.4% | 4.898 | PPAK | 179 | GVPINVKCKISRQCIEPCKDAGMRFGKCMNGKCHCHCTPKPPAK | 325 |
| KV1D819L1_74E03 | 97.3% | 7.943 | EPRP | 180 | GVPINVKCKISRQCIEPCKDAGMRFGKCMNGKCHCHCTPKEPRP | 326 |
| KV1D819L1_62B07 | 97.1% | 6.998 | TATH | 181 | GVPINVKCKISRQCIEPCKDAGMRFGKCMNGKCHCHCTPKTATH | 327 |
| KV1D819L1_67B08 | 97.0% | 5.370 | ARPD | 182 | GVPINVKCKISRQCIEPCKDAGMRFGKCMNGKCHCHCTPKARPD | 328 |
| KV1D819L1_61B02 | 96.8% | 2.754 | AHPH | 183 | GVPINVKCKISRQCIEPCKDAGMRFGKCMNGKCHCHCTPKAHPH | 329 |
| KV1D819L1_61D06 | 96.6% | 3.981 | AAPS | 184 | GVPINVKCKISRQCIEPCKDAGMRFGKCMNGKCHCHCTPKAAPS | 330 |
| KV1D819L1_74C08 | 96.5% | 6.095 | RPRP | 185 | GVPINVKCKISRQCIEPCKDAGMRFGKCMNGKCHCHCTPKRPRP | 331 |
| KV1D819L1_61E08 | 96.5% | 2.951 | PDKP | 186 | GVPINVKCKISRQCIEPCKDAGMRFGKCMNGKCHCHCTPKPDKP | 332 |
| KV1D819L1_58A06 | 96.3% | 7.079 | TPHP | 187 | GVPINVKCKISRQCIEPCKDAGMRFGKCMNGKCHCHCTPKTPHP | 333 |
| KV1D819L1_97C07 | 95.8% | 3.548 | RTRP | 188 | GVPINVKCKISRQCIEPCKDAGMRFGKCMNGKCHCHCTPKRTRP | 334 |
| KV1D819L1_62A11 | 95.8% | 10.471 | AQQH | 189 | GVPINVKCKISRQCIEPCKDAGMRFGKCMNGKCHCHCTPKAQQH | 335 |
| KV1D819L1_4H07 | 95.7% | | TRRP | 190 | GVPINVKCKISRQCIEPCKDAGMRFGKCMNGKCHCHCTPKTRRP | 336 |
| KV1D819L1_4H07 | 95.7% | | TRRP | 191 | GVPINVKCKISRQCIEPCKDAGMRFGKCMNGKCHCHCTPKTRRP | 337 |
| KV1D819L1_57B07 | 95.1% | 1.259 | RQPP | 192 | GVPINVKCKISRQCIEPCKDAGMRFGKCMNGKCHCHCTPKRQPP | 338 |
| KV1D819L1_63D11 | 95.0% | 5.248 | RTPP | 193 | GVPINVKCKISRQCIEPCKDAGMRFGKCMNGKCHCHCTPKRTPP | 339 |
| KV1D819L1_74G06 | 95.0% | 10.000 | EKPT | 194 | GVPINVKCKISRQCIEPCKDAGMRFGKCMNGKCHCHCTPKEKPT | 340 |
| KV1D819L1_68A01 | 94.6% | 0.372 | GHTA | 195 | GVPINVKCKISRQCIEPCKDAGMRFGKCMNGKCHCHCTPKGHTA | 341 |
| KV1D819L1_42C09 | 94.5% | 5.309 | PTKP | 196 | GVPINVKCKISRQCIEPCKDAGMRFGKCMNGKCHCHCTPKPTKP | 342 |
| KV1D819L1_61C03 | 94.3% | 1.603 | PTTP | 197 | GVPINVKCKISRQCIEPCKDAGMRFGKCMNGKCHCHCTPKPTTP | 343 |
| KV1D819L1_70A06 | 94.2% | 6.761 | TGHT | 198 | GVPINVKCKISRQCIEPCKDAGMRFGKCMNGKCHCHCTPKTGHT | 344 |
| KV1D819L1_45E05 | 93.9% | 3.055 | GGPQ | 199 | GVPINVKCKISRQCIEPCKDAGMRFGKCMNGKCHCHCTPKGGPQ | 345 |
| KV1D819L1_31H11 | 93.7% | 3.055 | HRRQ | 200 | GVPINVKCKISRQCIEPCKDAGMRFGKCMNGKCHCHCTPKHRRQ | 346 |
| KV1D819L1_68A07 | 93.5% | 4.266 | HNAP | 201 | GVPINVKCKISRQCIEPCKDAGMRFGKCMNGKCHCHCTPKHNAP | 347 |
| KV1D819L1_45E07 | 93.4% | 4.217 | PQPQ | 202 | GVPINVKCKISRQCIEPCKDAGMRFGKCMNGKCHCHCTPKPQPQ | 348 |

Figure 6 (continued)

| | | | | | | |
|---|---|---|---|---|---|---|
| KV1D819L1_15B03 | 92.8% | | NRRP | 203 | GVPINVKCKISRQCIEPCKDAGMRFGKCMNGKCHCTPKNRRP | 349 |
| KV1D819L1_61C07 | 92.5% | 3.936 | QAAP | 204 | GVPINVKCKISRQCIEPCKDAGMRFGKCMNGKCHCTPKQAAP | 350 |
| KV1D819L1_67E03 | 92.4% | 3.199 | QPQD | 205 | GVPINVKCKISRQCIEPCKDAGMRFGKCMNGKCHCTPKQPQD | 351 |
| KV1D819L1_3B08 | 81.4% | | ATRP | 206 | GVPINVKCKISRQCIEPCKDAGMRFGKCMNGKCHCTPKATRP | 352 |
| KV1D819L1_72E02 | 80.7% | 0.092 | NRPP | 207 | GVPINVKCKISRQCIEPCKDAGMRFGKCMNGKCHCTPKNRPP | 353 |
| KV1D819L1_2A05 | 64.3% | | RRRP | 208 | GVPINVKCKISRQCIEPCKDAGMRFGKCMNGKCHCTPKRRRP | 354 |
| KV1D819L1_5D10 | 57.3% | | AHRH | 209 | GVPINVKCKISRQCIEPCKDAGMRFGKCMNGKCHCTPKAHRH | 355 |
| KV1D819L1_5H06 | 53.6% | | AQRP | 210 | GVPINVKCKISRQCIEPCKDAGMRFGKCMNGKCHCTPKAQRP | 356 |
| KV1D819L1_74G01 | 53.0% | 4.955 | TSDT | 211 | GVPINVKCKISRQCIEPCKDAGMRFGKCMNGKCHCTPKTSDT | 357 |
| KV1D819L1_116E01 | 49.3% | 2.163 | RRPG | 212 | GVPINVKCKISRQCIEPCKDAGMRFGKCMNGKCHCTPKRRPG | 358 |
| KV1D819L1_55B03 | 43.9% | 0.036 | QSKA | 213 | GVPINVKCKISRQCIEPCKDAGMRFGKCMNGKCHCTPKQSKA | 359 |
| KV1D819L1_55E04 | 43.6% | 0.033 | AGPR | 214 | GVPINVKCKISRQCIEPCKDAGMRFGKCMNGKCHCTPKAGPR | 360 |
| KV1D819L1_55E03 | 40.1% | 0.028 | RSRT | 215 | GVPINVKCKISRQCIEPCKDAGMRFGKCMNGKCHCTPKRSRT | 361 |
| KV1D819L1_55H07 | 38.7% | 0.019 | RHKR | 216 | GVPINVKCKISRQCIEPCKDAGMRFGKCMNGKCHCTPKRHKR | 362 |
| KV1D819L1_62F01 | 35.5% | 0.275 | NAAK | 217 | GVPINVKCKISRQCIEPCKDAGMRFGKCMNGKCHCTPKNAAK | 363 |
| KV1D819L1_7F01 | 32.8% | 10.715 | APHT | 218 | GVPINVKCKISRQCIEPCKDAGMRFGKCMNGKCHCTPKAPHT | 364 |
| KV1D819L1_94H02 | 30.8% | 0.030 | GGKR | 219 | GVPINVKCKISRQCIEPCKDAGMRFGKCMNGKCHCTPKGGKR | 365 |
| KV1D819L1_103H06 | 29.2% | 4.624 | RREP | 220 | GVPINVKCKISRQCIEPCKDAGMRFGKCMNGKCHCTPKRREP | 366 |
| KV1D819L1_119F03 | 28.2% | | HTRT | 221 | GVPINVKCKISRQCIEPCKDAGMRFGKCMNGKCHCTPKHTRT | 367 |
| KV1D819L1_2A08 | 28.1% | | NHRT | 222 | GVPINVKCKISRQCIEPCKDAGMRFGKCMNGKCHCTPKNHRT | 368 |
| KV1D819L1_3H01 | 24.2% | | PNRT | 223 | GVPINVKCKISRQCIEPCKDAGMRFGKCMNGKCHCTPKPNRT | 369 |
| KV1D819L1_113G03 | 24.1% | 0.025 | PKTA | 224 | GVPINVKCKISRQCIEPCKDAGMRFGKCMNGKCHCTPKPKTA | 370 |
| KV1D819L1_99F08 | 22.3% | | TRRP | 225 | GVPINVKCKISRQCIEPCKDAGMRFGKCMNGKCHCTPKTRRP | 371 |
| KV1D819L1_3A01 | 22.2% | | RHNT | 226 | GVPINVKCKISRQCIEPCKDAGMRFGKCMNGKCHCTPKRHNT | 372 |
| KV1D819L1_93A04 | 20.4% | 0.036 | TDAR | 227 | GVPINVKCKISRQCIEPCKDAGMRFGKCMNGKCHCTPKTDAR | 373 |
| KV1D819L1_102D1 | 19.6% | 0.022 | HRQQ | 228 | GVPINVKCKISRQCIEPCKDAGMRFGKCMNGKCHCTPKHRQQ | 374 |
| KV1D819L1_116E04 | 19.3% | | NQRT | 229 | GVPINVKCKISRQCIEPCKDAGMRFGKCMNGKCHCTPKNQRT | 375 |
| KV1D819L1_91E03 | 19.3% | 0.039 | RPRH | 230 | GVPINVKCKISRQCIEPCKDAGMRFGKCMNGKCHCTPKRPRH | 376 |

Figure 6 (continued)

| Name | % | val | 4-letter | # | Sequence | # |
|---|---|---|---|---|---|---|
| KV1D819L1_61G03 | 18.6% | | HNET | 231 | GVPINVKCKISRQCIEPCKDAGMRFGKCMNGKCHCTPKHNET | 377 |
| KV1D819L1_93A08 | 18.5% | 0.106 | ARNA | 232 | GVPINVKCKISRQCIEPCKDAGMRFGKCMNGKCHCTPKARNA | 378 |
| KV1D819L1_3E09 | 18.4% | 0.040 | TTRT | 233 | GVPINVKCKISRQCIEPCKDAGMRFGKCMNGKCHCTPKTTRT | 379 |
| KV1D819L1_4E01 | 18.2% | | ARRN | 234 | GVPINVKCKISRQCIEPCKDAGMRFGKCMNGKCHCTPKARRN | 380 |
| KV1D819L1_60H04 | 18.1% | 0.022 | TGRK | 235 | GVPINVKCKISRQCIEPCKDAGMRFGKCMNGKCHCTPKTGRK | 381 |
| KV1D819L1_2E07 | 17.9% | | ASDN | 236 | GVPINVKCKISRQCIEPCKDAGMRFGKCMNGKCHCTPKASDN | 382 |
| KV1D819L1_91H11 | 17.0% | 0.009 | HERT | 237 | GVPINVKCKISRQCIEPCKDAGMRFGKCMNGKCHCTPKHERT | 383 |
| KV1D819L1_99F01 | 16.5% | | TPHR | 238 | GVPINVKCKISRQCIEPCKDAGMRFGKCMNGKCHCTPKTPHR | 384 |
| KV1D819L1_95H11 | 16.0% | 0.005 | RRTA | 239 | GVPINVKCKISRQCIEPCKDAGMRFGKCMNGKCHCTPKRRTA | 385 |
| KV1D819L1_117E05 | 16.0% | 0.038 | NTRT | 240 | GVPINVKCKISRQCIEPCKDAGMRFGKCMNGKCHCTPKNTRT | 386 |
| KV1D819L1_3A05 | 15.4% | | PTTR | 241 | GVPINVKCKISRQCIEPCKDAGMRFGKCMNGKCHCTPKPTTR | 387 |
| KV1D819L1_97G04 | 15.2% | 0.013 | QRNG | 242 | GVPINVKCKISRQCIEPCKDAGMRFGKCMNGKCHCTPKQRNG | 388 |
| KV1D819L1_115H04 | 14.1% | 0.039 | AHRN | 243 | GVPINVKCKISRQCIEPCKDAGMRFGKCMNGKCHCTPKAHRN | 389 |
| KV1D819L1_93H05 | 13.5% | 0.041 | PRSA | 244 | GVPINVKCKISRQCIEPCKDAGMRFGKCMNGKCHCTPKPRSA | 390 |
| KV1D819L1_111G02 | 13.3% | 0.019 | QRQS | 245 | GVPINVKCKISRQCIEPCKDAGMRFGKCMNGKCHCTPKQRQS | 391 |
| KV1D819L1_112F01 | 13.3% | 0.016 | QRRK | 246 | GVPINVKCKISRQCIEPCKDAGMRFGKCMNGKCHCTPKQRRK | 392 |
| KV1D819L1_115H06 | 13.2% | 0.012 | ARAK | 247 | GVPINVKCKISRQCIEPCKDAGMRFGKCMNGKCHCTPKARAK | 393 |
| KV1D819L1_3A03 | 13.2% | | RTRQ | 248 | GVPINVKCKISRQCIEPCKDAGMRFGKCMNGKCHCTPKRTRQ | 394 |
| KV1D819L1_96E04 | 12.6% | 0.019 | AKRD | 249 | GVPINVKCKISRQCIEPCKDAGMRFGKCMNGKCHCTPKAKRD | 395 |
| KV1D819L1_60B02 | 12.2% | 0.248 | DDGA | 250 | GVPINVKCKISRQCIEPCKDAGMRFGKCMNGKCHCTPKDDGA | 396 |
| KV1D819L1_96G04 | 12.0% | 0.013 | RDKT | 251 | GVPINVKCKISRQCIEPCKDAGMRFGKCMNGKCHCTPKRDKT | 397 |
| KV1D819L1_87G02 | 11.4% | 0.004 | HRRK | 252 | GVPINVKCKISRQCIEPCKDAGMRFGKCMNGKCHCTPKHRRK | 398 |
| KV1D819L1_4B01 | 11.0% | | RQTR | 253 | GVPINVKCKISRQCIEPCKDAGMRFGKCMNGKCHCTPKRQTR | 399 |
| KV1D819L1_61H04 | 8.7% | 0.141 | PNRD | 254 | GVPINVKCKISRQCIEPCKDAGMRFGKCMNGKCHCTPKPNRD | 400 |
| KV1D819L1_54D11 | 8.3% | 0.028 | HRHK | 255 | GVPINVKCKISRQCIEPCKDAGMRFGKCMNGKCHCTPKHRHK | 401 |
| KV1D819L1_12C08 | 7.9% | 0.331 | HRNR | 256 | GVPINVKCKISRQCIEPCKDAGMRFGKCMNGKCHCTPKHRNR | 402 |
| KV1D819L1_87C11 | 7.8% | 0.022 | RAKR | 257 | GVPINVKCKISRQCIEPCKDAGMRFGKCMNGKCHCTPKRAKR | 403 |
| KV1D819L1_57F05 | 7.2% | 0.021 | QRTR | 258 | GVPINVKCKISRQCIEPCKDAGMRFGKCMNGKCHCTPKQRTR | 404 |

Figure 6 (continued)

| | | | | |
|---|---|---|---|---|
| KV1D819L1_54G07 | 5.5% | 0.030 | ATRH | 259 | GVPINVKCKISRQCIEPCKDAGMRFGKCMNGKCHCTPKATRH | 405 |
| KV1D819L1_13F03 | 5.5% | 0.004 | ARRS | 260 | GVPINVKCKISRQCIEPCKDAGMRFGKCMNGKCHCTPKARRS | 406 |
| KV1D819L1_71B03 | 5.2% | 0.022 | AKTR | 261 | GVPINVKCKISRQCIEPCKDAGMRFGKCMNGKCHCTPKAKTR | 407 |
| KV1D819L1_53G01 | 4.8% | 0.065 | NARQ | 262 | GVPINVKCKISRQCIEPCKDAGMRFGKCMNGKCHCTPKNARQ | 408 |
| KV1D819L1_71G05 | 4.4% | 0.031 | NRQR | 263 | GVPINVKCKISRQCIEPCKDAGMRFGKCMNGKCHCTPKNRQR | 409 |
| KV1D819L1_6H05 | 4.2% | | PTNA | 264 | GVPINVKCKISRQCIEPCKDAGMRFGKCMNGKCHCTPKPTNA | 410 |
| KV1D819L1_45E01 | 4.1% | 0.195 | TRTD | 265 | GVPINVKCKISRQCIEPCKDAGMRFGKCMNGKCHCTPKTRTD | 411 |
| KV1D819L1_41D01 | 3.6% | 0.750 | ADTR | 266 | GVPINVKCKISRQCIEPCKDAGMRFGKCMNGKCHCTPKADTR | 412 |
| KV1D819L1_40A01 | 3.3% | 0.120 | TSRQ | 267 | GVPINVKCKISRQCIEPCKDAGMRFGKCMNGKCHCTPKTSRQ | 413 |
| KV1D819L1_50D06 | 3.3% | 0.015 | PRNT | 268 | GVPINVKCKISRQCIEPCKDAGMRFGKCMNGKCHCTPKPRNT | 414 |

*°Binding measured as % binding compared to KV1D261_26

Figure 7A

| Protein | Linker SEQ ID NO: | Competitive Binding Ki (nM) | Thallium Flux Kv1.3 IC$_{50}$ (nM) | Thallium Flux Kv1.1 IC$_{50}$ (nM) | Fold Selectivity* | C-terminal extension Amino acid sequence | C-terminal extension SEQ ID NO: | T cell inhibition %Inhibition @1nM | T cell inhibition IC$_{50}$ (nM) |
|---|---|---|---|---|---|---|---|---|---|
| KV1G28.KV1W699 | 428 | 3.60 | 1.122 | 63.096 | 56 | PKTA | 224 | 34.5% | NT |
| KV1G47.KV1W718 | 428 | 2.90 | 0.891 | 89.125 | 100 | TDAR | 227 | 21.9% | NT |
| KV1G48.KV1W719 | 428 | 18.00 | 0.891 | 28.184 | 32 | AHRN | 243 | 32.0% | NT |
| KV1G11.KV1W682 | 116 | 1.94 | 0.794 | 158.489 | 200 | HERT | 237 | 17.5% | NT |
| KV1G27.KV1W698 | 428 | 2.00 | 0.708 | 50.119 | 71 | PRNT | 268 | 47.4% | NT |
| KV1G42.KV1W713 | 428 | 1.30 | 0.562 | 63.096 | 112 | RNRE | 431 | 21.3% | NT |
| KV1G29.KV1W700 | 428 | 1.30 | 0.562 | 63.096 | 112 | ARNA | 232 | 35.0% | NT |
| KV1G38.KV1W709 | 428 | 2.30 | 0.501 | 63.096 | 126 | HRPA | 143 | 31.0% | NT |
| KV1G26.KV1W697 | 428 | 0.79 | 0.501 | 31.623 | 63 | RRTA | 239 | 37.9% | NT |
| KV1G37.KV1W708 | 428 | 1.20 | 0.447 | 35.481 | 79 | AGPR | 214 | 36.3% | NT |
| KV1G43.KV1W714 | 428 | 0.75 | 0.447 | 28.184 | 63 | NTRT | 240 | 39.8% | NT |
| KV1G40.KV1W711 | 428 | 0.90 | 0.398 | 44.668 | 112 | RRPG | 212 | 29.2% | NT |
| KV1G10.KV1W681 | 428 | 0.78 | 0.398 | 39.811 | 100 | NRPP | 207 | 30.1% | NT |
| KV1G35.KV1W706 | 428 | 0.49 | 0.398 | 39.811 | 100 | HHRQ | 432 | 31.6% | NT |
| KV1G30.KV1W701 | 428 | 1.40 | 0.398 | 28.184 | 71 | AKTR | 261 | 29.8% | NT |
| KV1G31.KV1W702 | 428 | 1.10 | 0.355 | 25.119 | 71 | RPRH | 230 | 32.9% | NT |

Figure 7A (continued)

| | | | | | | | | |
|---|---|---|---|---|---|---|---|---|
| KV1G39.KV1W710 | 428 | 0.49 | 0.355 | 17.783 | 50 | GGKR | 219 | 49.5% | NT |
| KV1G44.KV1W715 | 428 | 1.00 | 0.316 | 19.953 | 63 | TRAK | 433 | 37.1% | NT |
| KV1G36.KV1W707 | 428 | 0.32 | 0.282 | 17.783 | 63 | NRQR | 263 | 45.1% | NT |
| KV1G33.KV1W704 | 428 | 0.26 | 0.282 | 12.589 | 45 | RHKR | 216 | 15.1% | NT |
| KV1G34.KV1W705 | 428 | 0.15 | 0.282 | 10.000 | 35 | HRRK | 252 | 29.2% | NT |
| KV1G12.KV1W683 | 116 | 1.93 | 0.251 | 50.119 | 200 | HAKP | 155 | 23.6% | NT |
| KV1G13.KV1W684 | 116 | 0.61 | 0.251 | 31.623 | 126 | NARQ | 262 | 30.6% | NT |
| KV1G41.KV1W712 | 428 | 0.85 | 0.251 | 31.623 | 126 | RTRP | 188 | 34.8% | NT |
| KV1G18.KV1W689 | 116 | 0.85 | 0.126 | 39.811 | 316 | PNRT | 223 | 36.5% | NT |
| KV1G14.KV1W685 | 116 | 0.89 | 0.126 | 25.119 | 200 | AQRP | 210 | 38.5% | NT |
| KV1G19.KV1W690 | 116 | 0.59 | 0.063 | 25.119 | 398 | TTRT | 233 | 42.3% | NT |
| KV1G20.KV1W691 | 116 | 0.71 | 0.063 | 19.953 | 316 | ATRP | 206 | 44.4% | NT |
| KV1G9.KV1W680 | 116 | 0.29 | 0.032 | 15.849 | 501 | AHRP | 128 | 50.8% | 0.61 |
| KV1G6.KV1W677 | 116 | 0.08 | 0.025 | 7.943 | 316 | TGRK | 235 | 56.9% | 0.21 |
| KV1G16.KV1W687 | 116 | 0.20 | 0.025 | 7.943 | 316 | ARRN | 234 | 54.8% | 0.26 |
| KV1G15.KV1W686 | 116 | 0.31 | 0.016 | 10.000 | 631 | AHRH | 209 | 57.5% | 0.37 |
| KV1G7.KV1W678 | 116 | 0.24 | 0.013 | 10.000 | 794 | RRRP | 208 | 35.7% | 1.43 |

NT = Not tested

SEQ ID NO: 116: AS(AP)$_{20}$GS

SEQ ID NO: 428: GS(AP)$_{20}$AS

*ratio IC$_{50(Kv1.1)}$/IC$_{50(Kv1.3)}$

Figure 7B

| Compound ID | Competitive Binding Ki (nM) | T cell inhibition IC$_{50}$ (nM) | C-terminal extension | | Peptide | |
|---|---|---|---|---|---|---|
| | | | Amino acid sequence | SEQ ID NO: | Amino acid sequence | SEQ ID NO: |
| KV1G65.KV1W736 | 12.3 | 7.3 | AHRH | 209 | GVPTDVKCRISRQCEKPCKDAGMRFGKCMNGKCHCTPKAHRH | 415 |
| KV1G64.KV1W735 | 5.95 | 4.4 | TGRK | 235 | GVPTDVKCRISRQCEKPCKDAGMRFGKCMNGKCHCTPKTGRK | 416 |
| KV1G63.KV1W734 | 3.74 | 3.4 | ARRN | 234 | GVPTDVKCRISRQCEKPCKDAGMRFGKCMNGKCHCTPKARRN | 417 |
| KV1G49.KV1W720 | 28.6 | 15.8 | none | | GVPTDVKCRISRQCEKPCKDAGMRFGKCMNGKCHCTPK | 3 |

Figure 8

| Protein ID | Fusion partner | Linker SEQ ID NO: | Peptide portion | Peptide SEQ ID NO: | Patch clamp IC$_{50}$ (nM) Kv1.3 | Patch clamp IC$_{50}$ (nM) Kv1.1 | Patch clamp IC$_{50}$ (nM) Selectivity** | Thallium flux IC$_{50}$ (nM) KV1.3 | Thallium flux IC$_{50}$ (nM) KV1.1 | Thallium flux IC$_{50}$ (nM) Selectivity** | Tcell inhibition, IC$_{50}$ (nM) | Competitive Binding EC$_{50}$ (nM) | Competitive Binding Ki (nM) | C-terminal extension Amino acid sequence | C-terminal extension SEQ ID NO: |
|---|---|---|---|---|---|---|---|---|---|---|---|---|---|---|---|
| KV1C2 | Fc | 119 | OdK2 | 1 | 13 | 865 | 67 | 21.40 | >1000 | >46.7 | 69.9 | | | | |
| KV1N2 | Fc | 119 | OsK1 | 2 | 0.3 | 2 | 7 | 0.03 | 0.10 | 3.2 | 2.8 | | | | |
|

Figure 8 (continued)

| | | | | | | | | | |
|---|---|---|---|---|---|---|---|---|---|
| KV1G11.KV1W682 | HSA | 116 | p261 extended | | 0.794 | 158.489 | 200 | NT | 98.9 | 1.94 | HERT | 237 |
| KV1G26.KV1W697 | HSA | 116 | p261 extended | | 0.501 | 31.623 | 63 | NT | 40.3 | 0.79 | RRTA | 239 |
| KV1G27.KV1W698 | HSA | 116 | p261 extended | | 0.708 | 50.119 | 71 | NT | 102.0 | 2.00 | PRNT | 268 |
| KV1G28.KV1W699 | HSA | 116 | p261 extended | | 1.122 | 63.096 | 56 | NT | 183.6 | 3.60 | PKTA | 224 |
| KV1G29.KV1W700 | HSA | 116 | p261 extended | | 0.562 | 63.096 | 112 | NT | 66.3 | 1.30 | ARNA | 232 |
| KV1G30.KV1W701 | HSA | 116 | p261 extended | | 0.398 | 28.184 | 71 | NT | 71.4 | 1.40 | AKTR | 261 |
| KV1G31.KV1W702 | HSA | 116 | p261 extended | | 0.355 | 25.119 | 71 | NT | 56.1 | 1.10 | RPRH | 230 |
| KV1G33.KV1W704 | HSA | 116 | p261 extended | | 0.282 | 12.589 | 45 | NT | 13.3 | 0.26 | RHKR | 216 |
| KV1G34.KV1W705 | HSA | 116 | p261 extended | | 0.282 | 10.000 | 35 | NT | 7.7 | 0.15 | HRRK | 252 |
| KV1G35.KV1W706 | HSA | 116 | p261 extended | | 0.398 | 39.811 | 100 | NT | 25.0 | 0.49 | HHRQ | 432 |
| KV1G36.KV1W707 | HSA | 116 | p261 extended | | 0.282 | 17.783 | 63 | NT | 16.3 | 0.32 | NRQR | 263 |
| KV1G37.KV1W708 | HSA | 116 | p261 extended | | 0.447 | 35.481 | 79 | NT | 61.2 | 1.20 | AGPR | 214 |
| KV1G38.KV1W709 | HSA | 116 | p261 extended | | 0.501 | 63.096 | 126 | NT | 117.3 | 2.30 | HRPA | 143 |
| KV1G39.KV1W710 | HSA | 116 | p261 extended | | 0.355 | 17.783 | 50 | NT | 25.0 | 0.49 | GGKR | 219 |
| KV1G40.KV1W711 | HSA | 116 | p261 extended | | 0.398 | 44.668 | 112 | NT | 45.9 | 0.90 | RRPG | 212 |
| KV1G41.KV1W712 | HSA | 116 | p261 extended | | 0.251 | 31.623 | 126 | NT | 43.4 | 0.85 | RTRP | 188 |
| KV1G42.KV1W713 | HSA | 116 | p261 extended | | 0.562 | 63.096 | 112 | NT | 66.3 | 1.30 | RNRE | 431 |
| KV1G43.KV1W714 | HSA | 116 | p261 extended | | 0.447 | 28.184 | 63 | NT | 38.3 | 0.75 | NTRT | 240 |
| KV1G44.KV1W715 | HSA | 116 | p261 extended | | 0.316 | 19.953 | 63 | NT | 51.0 | 1.00 | TRAK | 433 |
| KV1G47.KV1W718 | HSA | 116 | p261 extended | | 0.891 | 89.125 | 100 | NT | 147.9 | 2.90 | TDAR | 227 |
| KV1G48.KV1W719 | HSA | 116 | p261 extended | | 0.891 | 28.184 | 32 | NT | 918.0 | 18.00 | AHRN | 243 |
| KV1G65.KV1W736 | HSA | 116 | p579 extended | | 9.1 | 6.6 | 2.6 | 7.3 | 629 | 12.3 | AHRH | 209 |
| KV1G64.KV1W735 | HSA | 116 | p579 extended | | 9.2 | 6.7 | 2.4 | 4.4 | 304 | 5.95 | TGRK | 235 |
| KV1G63.KV1W734 | HSA | 116 | p579 extended | | 9.1 | 7.1 | 2.0 | 3.4 | 191 | 3.74 | ARRN | 234 |
| KV1G49.KV1W720 | HSA | 116 | p579 extended | | 1.00 | 252.00 | 252.00 | 15.8 | 1460 | 28.6 | none | |

NT= not tested
*in CHO cells
** Ratio: $EC_{50}(Kv1.1)/EC_{50}(Kv1.3)$
SEQ ID NO: 116: AS(AP)$_{20}$GS
SEQ ID NO: 120: GS(G4S)$_8$
SEQ ID NO: 119: GS(G$_4$S)$_4$

KV1.3 ANTAGONISTS AND METHODS OF USE

This application claims the benefit of U.S. Provisional Application No. 61/757,389, filed 28 Jan. 2013, and U.S. Provisional Application No. 61/756,777, filed 25 Jan. 2013, the entire contents of which are incorporated herein by reference.

FIELD OF THE INVENTION

The present invention relates to antagonists of Kv1.3, polynucleotides encoding them, and methods of making and using the foregoing. The antagonists are based on variants of the OdK2 peptide.

BACKGROUND OF THE INVENTION

Ion channels regulate a diversity of cellular functions through generation of ionic currents, including cardiac, CNS, and immune physiology. It is estimated that between 5-30% of marketed drugs may regulate ion channel activity (Overington et al., Nat Reviews Drug Discovery 5:993-6, 2006). Subfamily selectivity is a desired feature of new therapeutics to improve efficacy and safety of current non-selective drugs, and poses a significant challenge for small molecules and known naturally occurring peptide toxins (Wickenden et al., Future Med Chem 4:661-79, 2012). This is especially true within large homologous families such as voltage-gated $K^+$, $Ca^+$ and $Na^+$ channels.

Kv1.3, the potassium voltage-gated channel subfamily A member 3, is expressed on T cells and functions to regulate T cell activation. Sustained calcium signaling is required for T cell activation for upregulation of cell surface activation markers and increase in cytokine production and proliferation via calcineurin dependent dephosphorylation and nuclear translocation of nuclear factor of activated T cells (NFAT). Inositol triphosphate (IP3) dependent release of internal calcium stores from the endoplasmic reticulum activates the calcium release activated calcium channels (CRAC) on the cell surface, providing an influx of extracellular calcium and sustained calcium signaling (reviewed in Cahalan et al., Immunol Rev 231:59-87, 2009). An efflux of potassium is required for the cells to remain in a hyperpolarized state and for calcium influx to be maintained for full T cell activation. This potassium efflux appears to be regulated through the voltage-gated potassium channel Kv1.3 and the calcium-activated potassium channel KCa3.1. Blockers selective for Kv1.3 have demonstrated that Kv1.3 is the potassium channel responsible for regulating calcium signaling, even in the absence of any inhibition of KCa3.1. (Beeton et al., Mol Pharmacol 67:1369-81, 2005). Blocking Kv1.3 depolarizes T cells and inhibits calcium entry, cytokine production, and proliferation of activated T cells in vitro (reviewed in Cahalan et al., Immunol Rev 231:59-87, 2009).

Kv1.3 blockers have been shown to reduce T cell dependent disease progression in autoimmune models, such as experimental autoimmune encephalomyelitis (EAE), experimental arthritis, delayed-type hypersensitivity (DTH), allergic contact dermatitis and glomerulonephritis (Rangaraju et al., Expert Opin Ther Targets 13:909-24, 2009; Beeton et al., Proc Natl Acad Sci USA. 103:17414-9, 2006; Koo et al., J Immunol 158:5120-8, 1997; Hyodo et al., Am J Physiol Renal Physiol 299:F1258-69, 2010). The calcium calcineurin NFAT pathway inhibitors cyclosporine A (Neoral, Sandimmune, Gengraf) and Tacrolimus (FK-506 or fujimycin) are approved treatments for severe immune disorders, including transplant rejection and severe rheumatoid arthritis. The broad distribution of calcineurin in tissues such as kidneys may result in a higher degree of mechanism based toxicity, narrow safety margins, and limited therapeutic application for these compounds. T cell inhibition using selective Kv1.3 blockers may result in increased safety profile and greater efficacy in the treatment of T cell mediated inflammatory and autoimmune diseases.

Kv1.3 may play a role in regulating weight gain and improving insulin sensitivity. Kv1.3 deficient mice show reduced weight gain, higher insulin sensitivity, and reduced plasma glucose levels (Xu et al., Hum Mol Genet 12:551-9, 2003). Kv1.3 blockers have been shown to increase glucose transporter 4 (GLUT4) cell surface expression in skeletal muscle and adipose tissue, and result in increased insulin sensitivity in normal and ob/ob obese mice, and to increase glucose uptake in primary adipocytes in vitro (Xu et al., Proc Natl Acad Sci USA 101:3112-7, 2004). In humans, a single nucleotide polymorphism (SNP) in the Kv1.3 gene has been associated with decreased insulin sensitivity and impaired glucose tolerance (Tschritter, Clin Endocrinol Metab 91:654-8, 2006).

Kv1.3 may have a critical function in smooth muscle proliferative disorders like restenosis in patients following vascular surgery, such as angioplasty. Kv1.3 expression is increased in proliferating human and mouse smooth muscle cells. Kv1.3 blockers inhibit calcium entry, reduce smooth muscle cell migration, and inhibit neointimal hyperplasia in ex vivo human vein samples (Cheong et al., Cardiovasc Res 89:282-9, 2011).

Increasing evidence indicates that Kv1.3 channels are involved in the activation and/or proliferation of many types of cells, including tumor cells (Bielanska et al., Curr Cancer Drug Targets 9:904-14, 2009), microglia (Khanna et al., Am J Physiol Cell Physiol 280:C796-806, 2001) and differentiation of neuronal progenitor cells (Wang et al., J Neurosci 30:5020-7, 2010) suggesting that Kv1.3 blockers may be beneficial in the treatment of neuroinflammatory and neurodegenerative diseases, and cancers.

Toxin peptides produced by a variety of organisms have evolved to target ion channels. Snakes, scorpions, spiders, bees, snails, sea anemone, insects, arachnids, cnidarians, reptiles, and mollusks are a few examples of organisms that produce venom that can serve as a rich source of small bioactive toxin peptides or "toxins" that potently and selectively target ion channels and receptors. In most cases, these toxin peptides have evolved as potent antagonists or inhibitors of ion channels, by binding to the channel pore and physically blocking the ion conduction pathway or by antagonizing channel function by binding to a region outside the pore (e.g., the voltage sensor domain). Toxins peptides are typically about 20-80 amino acids long with distinct disulfide bond pairing, and can be divided into a number of superfamilies based on their disulfide connections and peptide folds. Many venom toxins are being engineered to improve their properties such as selectivity (King, Expert Opin Biol Ther 11:1469-84, 2011; Escoubas and King, Expert Review Proteomics 6:221-4, 2009).

Venom peptides demonstrating Kv1.3 blocking include ShK, OdK2, OsK1, margatoxin, kaliotoxin etc (see Chandy et al., Trends in Pharmacol Sci 25:280-9, 2004). Kv1.3 blockers OdK2 and OsK1 (alpha-KTx3.7) are homologous members of the α-KTx3 scorpion toxin family from the venom of *Odontobuthus doriae* and *Orthochirus scrobiculosus*, respectively (Abdel-Mottaleb et al., Toxicon 51:1424-30, 2008; Mouhat et al., Biochem J 385(Pt 1):95-104, 2005;

Int. Pat. Publ. No. WO2006/002850). OsK1 (alpha-KTx3.7) was reported to block Kv1.3, Kv1.1 and Kv1.2 channels potently and KCa3.1 channel moderately (Mouhat et al., Biochem J 385(Pt 1):95-104, 2005). OdK2 (alpha-KTx3.11) was reported to block Kv1.3 while having no activity on Kv1.1, Kv1.2, Kv1.4, Kv1.5, and Kv1.6) (Abdel-Mottaleb et al., Toxicon 51:1424-30, 2008; Epub 2008 Mar. 29).

Engineered toxin peptides with improved potency, selectivity and/or half life including OsK1 and ShK have been reported (Int. Pat. Appl. Publ. WO2006/002850; Int. Pat. Appl. Publ. WO2006/042151; Int. Pat. Appl. Publ. WO2008/088422, Int. Pat. Appl. Publ. WO2006/116156).

There exists a need for more potent and selective Kv1.3 blockers for the therapeutic treatment of Kv1.3-mediated diseases such as T-cell mediated inflammatory and autoimmune diseases such as lupus and multiple sclerosis.

BRIEF DESCRIPTION OF THE DRAWINGS

FIG. 1 Amino acid sequence alignment of native OdK2 (SEQ ID NO: 1) and OsK1 (SEQ ID NO: 2) (shown as OsK-1 in the figure). Cysteine residues are highlighted in grey. Disulfide bridges and cysteine pairs are shown. The nine divergent residues between OdK2 and OsK1 are highlighted in black.

FIG. 4. A) Amino acid sequences, B) Activity and selectivity of peptide variant fusion proteins determined in binding and thallium flux assays using cells expressing Kv1.3 and Kv1.1.

FIG. 6. Activity of p261 C-terminal extension HSA fusion protein library. Amino acid sequences of the C-terminal extensions and the resulting extended p261 amino acid sequences are shown, along with activity in binding and thallium flux assays.

FIG. 7. Characterization of A) p261 B) p579 C-terminal extension HSA fusion proteins.

FIG. 8. Characteristics of select OdK2 variant fusion proteins.

SUMMARY OF THE INVENTION

Figure 2A:
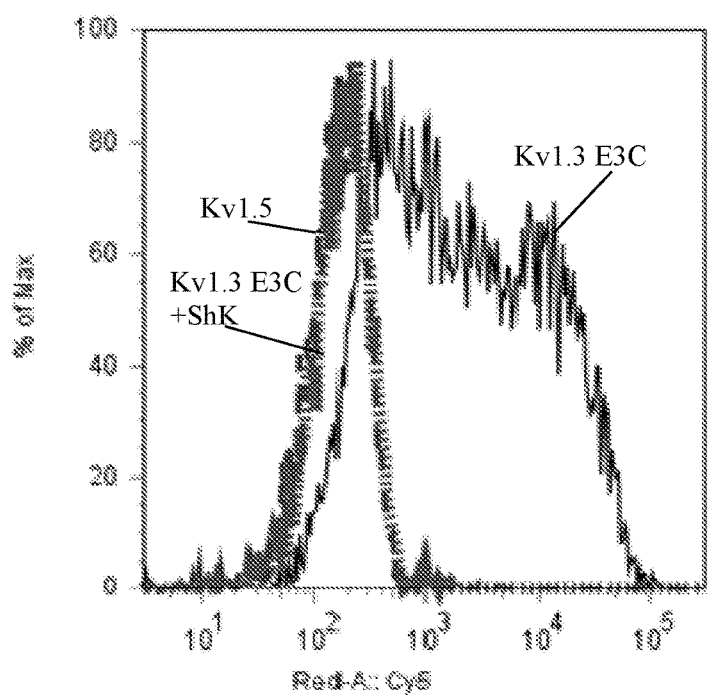
FIG. 2 Binding of A) KV1C2 (Odk2-Fc fusion) and B) KV1N2 (OsK1-Fc fusion) to Kv1.3 E3C cells (solid black), Kv1.3 E3C cells in the presence of a 10-fold excess ShK (dashed grey), and to Kv1.5 (negative control cells; dotted grey). Binding was detected with anti-human Fc-Cy5 using flow cytometry. Data are shown as histogram overlays of Geometric mean fluorescence intensity (GMFI) (Geom. Mean, Red A: Cy5).

One embodiment of the invention is an isolated fusion protein comprising a peptide antagonist of Kv1.3 conjugated to a half-life extending moiety, wherein the peptide antagonist of Kv1.3 comprises
the sequence shown in SEQ ID NO: 1 having a substitution of glycine to isoleucine at position 10 (G10I), and optionally having 1, 2, 3, 4, 5, 6 or 7 additional substitutions; or an amino acid sequence which is at least 80% identical to SEQ ID NO: 1, further comprising a G10I substitution; and the peptide antagonist of Kv1.3 optionally comprises a C-terminal extension of four amino acids.

Another embodiment of the invention is an isolated fusion protein comprising a peptide antagonist of Kv1.3 conjugated to a half-life extending moiety via a linker, the peptide antagonist of Kv1.3 having an optional C-terminal extension of four amino acids, wherein
the peptide antagonist of Kv1.3 comprises the amino acid sequence of SEQ ID NOs: 3-110;
the C-terminal extension comprises the amino acid sequence of SEQ ID NOs: 123-268;
the linker comprises the amino acid sequence of SEQ ID NOs: 112-122 or 428; and
the half-life extending moiety is human serum albumin.

Another embodiment of the invention is an isolated polynucleotide encoding the fusion protein of the invention.

Another embodiment of the invention is a vector comprising the isolated polynucleotide of the invention.

Another embodiment of the invention is a host cell comprising the vector of the invention.

Another embodiment of the invention is a method of producing the isolated fusion protein of the invention, comprising culturing the host cell of the invention and recovering the fusion protein expressed by the host cell.

Another embodiment of the invention is a pharmaceutical composition comprising the fusion protein of the invention and a pharmaceutically acceptable carrier.

Another embodiment of the invention is a method of suppressing T cell activation in a subject having a condition associated with undesired T cell activation, comprising administering to the subject an effective amount of the isolated fusion protein of the invention to suppress T cell activation.

Another embodiment of the invention is an isolated peptide antagonist of Kv1.3 comprising
the sequence shown in SEQ ID NO: 1 having a substitution of glycine to isoleucine at position 10 (G10I), and optionally having 1, 2, 3, 4, 5, 6 or 7 additional substitutions; or an amino acid sequence which is at least 80% identical to SEQ ID NO: 1, further comprising a G10I substitution; and the peptide antagonist of Kv1.3 optionally comprises a C-terminal extension of four amino acids.

Another embodiment of the invention is an isolated polynucleotide encoding the peptide antagonist of the invention.

Another embodiment of the invention is a method of producing the isolated peptide antagonist of Kv1.3 of the invention, comprising culturing the host cell of the invention and recovering the peptide antagonist of Kv1.3 expressed by the host cell.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The term "polypeptide" means a molecule that comprises at least two amino acid residues linked by a peptide bond to form a polypeptide. Polypeptides of less than about 80 amino acids may be referred to as "peptides". Polypeptides may also be referred as "proteins".

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "complementary sequence" means a second isolated polynucleotide sequence that is antiparallel to a first isolated polynucleotide sequence and that comprises nucleotides complementary to the nucleotides in the first polynucleotide sequence.

The term "vector" means a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a polypeptide encoded by a polynucleotide sequence present in the expression vector.

The term "wild type OdK2" or "OdK2" or "native OdK2" as used herein refers to scorpion *Odontobuthus doriae* OdK2 polypeptide having a sequence shown in SEQ ID NO: 1 (GVPTDVKCRGSPQCIQPCKDAGMRFGKCMNG-KCHCTPK).

The term "wild type OsK1" or "OsK1" or "native OsK1" as used herein refers to scorpion *Orthochirus scrobiculosus* OsK1 polypeptide having a sequence shown in SEQ ID NO: 2 (GVIINVKCKISRQCLEPCKKAGMRFGKCMNG-KCHCTPK).

The term "variant" or "OdK2 variant" as used herein refers to a polypeptide that differs from the wild type OdK2 polypeptide of SEQ ID NO: 1 by one or more modifications for example, substitutions, insertions or deletions of nucleotides or amino acids.

Throughout the specification, residue numbering of OdK2 variants is according to SEQ ID NO: 1. For example, "G10" in the specification refers to the glycine residue at position 10 of SEQ ID NO: 1. Accordingly, OdK2 G10I refers to an OdK2 variant having glycine at position 10 substituted for isoleucine, and OdK2 G10I,P12R refers to an OdK2 variant having glycine at position 10 substituted for isoleucine, and proline at position 12 substituted for arginine.

"Kv1.3" (also known as KCNA3, HPCN3, HGK5, HuKIII, or HLK3) as used herein refers to the well known human potassium voltage-gated channel subfamily A member 3 having a sequence shown in UniProt accession number P22001 and in SEQ ID NO: 418.

"Antagonist of Kv1.3" or "antagonist" as used herein refers to an OdK2 variant or OdK2 variant fusion protein of the invention that inhibits or blocks Kv1.3 function by at least 10%, 20%, 30%, 40%, 50%, 60%, 70%, 75%, 80%, 85%, 90%, 95% or 100%. Amino acid sequence of the wild type OdK2 is shown in SEQ ID NO: 1.

"Fusion protein" as used herein refers to a protein that includes polypeptide or peptide components derived from more than one parental polypeptide or peptide.

"Half-life extending moiety" as used herein refers to a molecule or protein or domain that, when conjugated to the OdK2 variant increases the in vivo half life of the resulting OdK2 variant fusion protein when compared to the free peptide.

"Percent binding" or "% Binding" as used herein refers to a ratio of geometric mean fluorescence intensities (Geo. MFI or GMFI) for an OdK2 variant fusion protein when compared to the control, obtained from a FACS assay using cells expressing Kv1.3 or Kv1.1 channels.

"Binding selectivity" as used herein refers to the ratio of % Binding obtained for Kv1.3 to % Binding obtained for Kv1.1.

"Selective" or "selectivity" as used herein refers to the ratio of an $IC_{50}$ value for Kv1.1 to an $IC_{50}$ value for Kv1.3 for an OdK2 variant fusion protein or OdK2 variant. Selectivity can be assessed using various methodologies, for example electrophysiological patch clamp assays or thallium flux assays as described herein. Selectivity may vary slightly depending on the assay chosen for measurements.

The Kv1.3 blocking peptides Odk2 (SEQ ID NO: 1) and Osk1 (SEQ ID NO: 2) are members of the α-KTx3 scorpion toxin family that differ in amino acid sequence at nine positions. Both OdK2 and Osk1 are 38 amino acids in length, and are each stabilized by three disulfide bonds with paring between Cys8-Cys28, Cys14-Cys33, and Cys18-Cys35 (Abdel-Mottaleb et al., Toxicon 51:1424-30, 2008; Mouhat et al., Biochem J. 385(Pt 1):95-104, 2005; Int. Pat. Publ. No. WO2006/002850). The folded peptides form an α-helix held in close proximity to a 3 stranded anti parallel β-sheet by the disulfide bonds. OdK2 and OsK1 are pore blockers that inhibit channel function through binding to the outer vestibule of the pore region, inserting lysine 27 into the water filled pore, and occluding ion flow. OsK1 (alpha-KTx3.7) is reported to block Kv1.3, Kv1.1 and Kv1.2, channels potently and KCa3.1 channel moderately, with an $IC_{50}$ of 0.014 nM, 0.6 nM, 5.4 nM, and 225 nM, respectively (Mouhat et al., Biochem J 385(Pt 1):95-104, 2005). OdK2 (alpha-KTx3.11) is reported to block Kv1.3 in *Xenopus laevis* oocytes, with an $IC_{50}$ of 7.2 nM, and is reported to have no activity on other Kv1.x subtypes tested (Kv1.1, Kv1.2, Kv1.4, Kv1.5, and Kv1.6) (Abdel-Mottaleb et al., Toxicon 51:1424-30, 2008). These data indicate that OsK1 is very potent but lacks sufficient subtype selectivity, whereas OdK2 appears selective but not highly potent.

The present invention provides isolated OdK2 variants and OdK2 variant fusion proteins that inhibit Kv1.3, polynucleotides encoding them, vectors, host cells, and methods of using the polynucleotides and polypeptides of the invention. The OdK2 variants and OdK2 variant fusion proteins of the invention are more potent towards Kv1.3 when compared to the parent molecules with retained and/or enhanced selectivity. The polypeptides of the invention inhibit potassium currents, thallium flux and/or T cell activation resulting from Kv1.3 activity and therefore may be useful in the treatment of various conditions associated with activated T cells, such as inflammatory and autoimmune diseases.

Compositions of Matter

One embodiment of the invention is an isolated fusion protein comprising a peptide antagonist of Kv1.3 conjugated to a half-life extending moiety, wherein the peptide antagonist of Kv1.3 comprises the sequence shown in SEQ ID NO: 1 having a substitution of glycine to isoleucine at position 10 (G10I), and optionally having 1, 2, 3, 4, 5, 6 or 7 additional substitutions; or an amino acid sequence which is at least 80% identical to SEQ ID NO: 1, further comprising a G10I substitution; and the peptide antagonist of Kv1.3 optionally comprises a C-terminal extension of four amino acids.

In some embodiments the peptide antagonist of Kv1.3 comprises a sequence with no more than 7, no more than 6, no more than 5, no more than 4, no more than 3, or no more than 2 substitutions relative to SEQ ID NO: 1.

In some embodiments, the peptide antagonist of Kv1.3 comprises a sequence which is at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO: 1. Percent identity between peptide sequences can be assessed using well known methods.

Exemplary peptide antagonists of Kv1.3 comprise the sequence of SEQ ID NOs: 3-54, 56-85, and 87-110. The substitution G10I in SEQ ID NO: 1 may be associated with improved selectivity and/or improved affinity for Kv1.3.

In some embodiments described herein, the peptide antagonist of Kv1.3 comprises the sequence GVPXaa$_1$Xaa$_2$VKCXaa$_3$ISRQCXaa$_4$Xaa$_5$PCKDAG-MRFGKCMNGKCHCTPK (SEQ ID NO: 426); wherein a) Xaa$_1$ is I or T, Q or E;
b) Xaa$_2$ is N or D;
c) Xaa$_3$ is K, R, E, A or Q;
d) Xaa$_4$ is I, E, L, D, Q, H, V, K or A; and
e) Xaa$_5$ is E, K, L, Q, D, V or H.

For example, the peptide antagonist of Kv1.3 may comprise the amino acid sequence of SEQ ID NOs: 3, 13, 21, 22, 24, 26, 29, 30, 32, 34, 38, 39, 42-46, 49, 51, 59, 63, 65, 69, 71, 73, 76, 78, 81-83, 85, 87, 89, 92, 96, 101, 103, 104 and 108.

In some embodiments described herein, the peptide antagonist of Kv1.3 comprises the sequence GVPXaa$_1$Xaa$_2$VKCXaa$_3$ISRQCXaa$_4$Xaa$_5$PCKDA-GMRFGKCMNGKCHCTPK (SEQ ID NO: 427); wherein Xaa$_1$ is I or T;
Xaa$_2$ is N or D;
Xaa$_3$ is K or R;
Xaa$_4$ is I or E; and
Xaa$_5$ is E or K.

For example, the peptide antagonist of Kv1.3 may comprise the amino acid sequence of SEQ ID NOs: 3, 22, 34 or 42.

In some embodiment described herein, the C-terminal extension comprises the amino acid sequence of SEQ ID NOs: 123-268.

In some embodiment described herein, the C-terminal extension comprises the amino acid sequence of SEQ ID NOs: 128, 143, 155, 188, 206-210, 212, 214, 216, 219, 223, 224, 227, 230, 232-235, 237, 239, 240, 243, 252, 261-263, or 268.

The OdK2 variant fusion proteins of the invention (i.e. peptide antagonists of Kv1.3 conjugated to a half-life extending moiety) are more potent and selective when compared to the fusion protein of native OdK2 sequence, such as KV1C2 (parent KV1C2 fusion protein) of SEQ ID NO: 425. Exemplary fusion proteins of the invention are those comprising OdK2 variant peptides of SEQ ID NOs: 3, 22, 34 or 42 conjugated to human serum albumin (HSA) via a linker AS(AP)$_{20}$GS (SEQ ID NO: 116).

The parent KV1C2 fusion protein has an IC$_{50}$ of about 13 nM ($1.3 \times 10^{-8}$ M) for inhibiting potassium currents in whole cell patch clamp studies in CHO cells transfected with human Kv1.3, and an IC$_{50}$ value of about 21.4 nM ($2.14 \times 10^{-8}$ M) for inhibiting thallium flux in cells expressing Kv1.3 using FLIPR® Tetra instrument (Molecular Devices). The OdK2 variant fusion protein of the invention as described herein is "equally potent or more potent" Kv1.3 inhibitor when the IC$_{50}$ value in the patch clamp assay described in the materials and methods is about 13 nM ($1.3 \times 10^{-8}$ M) or less, for example $1.0 \times 10^{-8}$ M, $5.0 \times 10^{-9}$ M, $1.0 \times 10^{-9}$ M, $5.0 \times 10^{-10}$ M, $1.0 \times 10^{-10}$ M, $5.0 \times 10^{-11}$ M, $1.0 \times 10^{-11}$ M, $5.0 \times 10^{-12}$ M, $1.0 \times 10^{-12}$ M or less, or the IC$_{50}$ value in the thallium flux assay described in the materials and methods is about 21.4 nM ($2.14 \times 10^{-8}$ M) or less, for example $1.0 \times 10^{-8}$ M, $5.0 \times 10^{-9}$ M, $1.0 \times 10^{-9}$ M, $5.0 \times 10^{-10}$ M, $1.0 \times 10^{-10}$ M, $5.0 \times 10^{-11}$ M, $1.0 \times 10^{-11}$ M, $5.0 \times 10^{-12}$ M, $1.0 \times 10^{-12}$ M or less. The IC$_{50}$ values for patch clamp and thallium flux for exemplary fusion proteins are shown in FIG. 8.

The OdK2 variant and OdK2 variant fusion proteins of the invention as described herein are selective for Kv1.3. Selectivity can be assessed against Kv1.1 using the ratio of an IC$_{50}$ value for Kv1.1 to an IC$_{50}$ value for Kv1.3 for an OdK2 variant fusion protein or OdK2 variant. Selectivity can be further tested against other Kv channels, such as Kv1.2, Kv1.4, Kv1.5, and against hERG, KCa3.1, or Nav1.5 using standard methods. The exemplary OdK2 variant fusion proteins of the invention as described herein can have substantially selectivity for Kv1.3 against Kv1.1, for example 100, 200, 300, 400, 500, 1000, 2000, 3000, 4000, 5000, 6000 or at least 7000 fold selectivity. The parent KV1C2 fusion protein is 68-fold more selective towards human Kv1.3 when compared to human Kv1.1, therefore, the exemplary OdK2 variant fusion proteins of the invention as described herein can have substantially enhanced selectivity, for example about 1.5, 3, 4.5, 6, 7.5, 10, 15, 20, 25, 30, 35, 40, 45, 50, 55, 60, 65, 70, 75, 80, 85, 90, 95, 100 or at least 105 fold improved selectivity when compared to the KV1C2 fusion protein. The presence of glutamic acid at position 15 of SEQ ID NO: 1 has been observed to improve selectivity.

Residue positions 4, 5, 9, 15 and 16 (residue numbering according to native OdK2 peptide of SEQ ID NO: 1) can be substituted in the native OdK2 to improve both potency and selectivity of the resulting OdK2 variants or fusion proteins. The residue positions can be substituted with any amino acid residue as long as the resulting OdK2 variant or its fusion protein, in the above whole cell patch clamp assay or thallium flux assay retains an IC$_{50}$ of about 13 nM ($1.3 \times 10^{-8}$ M) or 21.4 nM ($2.14 \times 10^{-8}$), respectively, or less, and has selectivity (expressed as a ratio of IC$_{50}$ values obtained using patch clamp as described above) for Kv1.3 against Kv1.1 of at least 100. The amino acid sets that can be used for diversification at each selected position include amino acid residues TIQE at position 4, ND at position 5, REAKQ at position 9, ELDIQHVKA at position 15, and KELQDVH at position 16. A glutamic acid (E) at position 15 is associated with increased selectivity for Kv1.3. The substitution G10I is associated with improved selectivity and/or improved affinity for Kv1.3 (residue numbering according to SEQ ID NO: 1). Diversification of OdK2 and its fusion proteins using the amino acid sets described above has resulted in variants displaying improved binding affinity and improved binding selectivity for Kv1.3 when compared to the native peptide or its fusion protein. In another diversification scheme, the amino acid sets that can be used for diversification at each selected position include amino acid residues IT at position 4, ND at position 5, KR at position 9, IE at position 15, and EK at position 16. The resulting variants and/or their fusion proteins can be assessed for selectivity, potency, binding affinity and binding selectivity using well known assays and the ones described within. Exemplary OdK2 variants and their fusion proteins with improved potency and selectivity are variants of SEQ ID NOs: 3, 22, 34 and 42, and their human serum albumin or Fc fusion proteins. Exemplary OdK2 variants with improved binding affinity and % Binding selectivity are variants of SEQ ID NOs: 3, 13, 21, 22, 24, 26, 29, 30, 32, 34, 38, 39, 42-46, 49, 51, 59, 63, 65, 69, 71, 73, 76, 78, 81-83, 85, 87, 89, 92, 96, 101, 103, 104 and 108.

Additional OdK2 variants and OdK2 variant fusion proteins are within the scope of the invention. For example, substitutions can be made in the native OdK2 peptide to positions other than positions 4, 5, 9, 15 and 16 as long as the resulting OdK2 variant and the OdK2 variant fusion protein retains similar selectivity and potency towards Kv1.3 when compared to the parent molecule. Exemplary modifications are for example conservative substitutions that will result in OdK2 variant fusion proteins with similar characteristics to those of the parent molecules. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Non-conservative substitutions can be made to the native OdK2 peptide that involves substitutions of amino acid residues between different classes of amino acids to improve properties of the OdK2 variants and OdK2 variant fusion proteins. Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner. Exemplary additional OdK2 variants and/or OdK2 variant fusion proteins having substitutions resulting in enhanced binding or binding specificity are those having the amino acid sequence of SEQ ID NOs: 4-12, 14-20, 23, 25, 27, 28, 31, 33, 35-37, 40, 41, 47, 48, 50, 52-58, 60-62, 64, 66-68, 70, 72, 74, 75, 77, 79, 80, 84, 86, 88, 90, 91, 93-95, 97-100, 102, 105-107, 109 and 110.

The OdK2 variants (i.e. antagonists according to the invention) as described herein can be fused to a half-life extending moiety to form fusion proteins of the invention. Exemplary half-life extending moieties that can be used include well known human serum albumin, transthyretin (TTR), a thyroxine-binding globulin TGB), albumin-binding domains, or an Fc or fragments thereof. Biologically suitable polymers or copolymers can also be used, for example ethylene glycol, polyethylene glycol (PEG) molecules, such as PEG5000 or PEG20000, dextran, polylysine, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, or carbohydrates (dextran, cellulose, oligo- or polysaccharides.

In another embodiment, the half-life extending moiety of the fusion protein described herein is human serum albumin, albumin binding domain (ADB), or polyethylene glycol (PEG).

In another embodiment, the half-life extending moiety of the fusion protein described herein is human serum albumin.

In another embodiment, the half-life extending moiety of the fusion protein described herein is conjugated to the peptide antagonist of Kv1.3 via a linker.

In another embodiment, the linker of the fusion protein described herein comprises the amino sequence of SEQ ID NOs: 112-122.

The half-life extending moiety can be conjugated directly to the OdK2 variant peptide antagonist of the invention or indirectly via a linker. Exemplary peptide linkers that can be used in fusion proteins of the invention as described herein are linkers having the amino acid sequence of SEQ ID NOs: 112-122 or 428. Non-peptide half-life extending moieties can be conjugated directly to the OdK2 variant using well known chemical coupling methods. For example, OdK2 variants can be pegylated using known methods and those described in U.S. Pat. No. 8,043,829. Peptide or protein half-life extending moieties can be linked to the peptide during translation of the nucleic acid encoding the fusion protein, as explained in more detail below.

OdK2 variants incorporating half-life extending moieties may be compared for functionality by several well known assays. For example, pharmacokinetic properties of OdK2 variants coupled to PEG or human serum albumin may be evaluated in well known in vivo models.

The OdK2 variant fusion proteins of the invention as described herein may be engineered to incorporate a C-terminal extension of four amino acids to the C-terminus of the Odk2 variant before conjugation of the extended peptide to a half-life extending moiety. By not wishing to be bound by any theory, it is believed that extending the C terminus of the OdK2 variant peptide in the fusion proteins would allow for increased binding interactions of the peptide with the extracellular loops of the Kv1.3 channel and increased potency. Exemplary OdK2 fusion proteins with C-terminally extended peptide portion are shown in FIG. 6, FIG. 7A and FIG. 8. The fusion proteins with C-terminally extended peptide portion are typically more potent Kv1.3 inhibitors when compared to the corresponding fusion proteins without the extension. $IC_H$ values for exemplary C-terminally extended variants described herein can be about $1\times10^{-8}$ M or less, for example about $1\times10^{-9}$ M or less, about $1\times10^{-10}$ M or less, about $1\times10^{-11}$ M or less, or about $1\times10^{-12}$ M or less as measured in thallium flux assay described below. Exemplary C-terminal extensions are those shown in SEQ ID NOs: 123-268.

In another embodiment, the isolated fusion protein of the invention comprises:
the peptide antagonist of Kv1.3 of SEQ ID NOs: 3, 22, 34 or 42;
optionally the C-terminal extension of SEQ ID NOs: 128, 143, 155, 188, 206-210, 212, 214, 216, 219, 223, 224, 227, 230, 232, 235, 237, 239, 240, 243, 252, 261-263, or 268;
the linker of SEQ ID NO: 116 or SEQ ID NO:119; and human serum albumin as the half-life extending moiety.

In another embodiment, the isolated fusion protein of the invention comprises
the peptide antagonist of Kv1.3 of SEQ ID NO: 42; the linker of SEQ ID NO: 116; and
human serum albumin as the half-life extending moiety.

In another embodiment, the isolated fusion protein of the invention comprises
the peptide antagonist of Kv1.3 of SEQ ID NO: 42;
the C-terminal extension SEQ ID NO: 209;
the linker of SEQ ID NO: 116; and
human serum albumin as the half-life extending moiety.

In another embodiment, the isolated fusion protein of the invention comprises
the peptide antagonist of Kv1.3 of SEQ ID NO: 3;
the C-terminal extension of SEQ ID NO: 235;
the linker of SEQ ID NO: 116; and
human serum albumin as the half-life extending moiety.

In another embodiment, the isolated fusion protein of the invention comprises
the peptide antagonist of Kv1.3 of SEQ ID NO: 42;
the C-terminal extension of SEQ ID NO: 235;
the linker of SEQ ID NO: 116; and
human serum albumin as the half-life extending moiety.

In another embodiment, the isolated fusion protein of the invention as described herein is at least 100 fold more selective towards human Kv1.3 than towards human Kv1.1, when selectivity is measured as a ratio of an $IC_{50}$ value of the isolated fusion protein for Kv1.1 to an $IC_{50}$ value of the isolated fusion protein for Kv1.3 in a patch clamp assay in cells transfected with Kv1.1 and Kv1.3, respectively.

In another embodiment, the isolated fusion protein of the invention as described herein inhibits potassium currents with an $IC_{50}$ value at least about 10 fold less than an $IC_{50}$ value for a parent KV1C2 fusion protein of SEQ ID NO: 425 in a patch clamp assay in cells transfected with human Kv1.3.

In another embodiment, the isolated fusion protein of the invention as described herein inhibits potassium currents with an $IC_{50}$ value of about $1.5 \times 10^{-8}$ M or less in a patch clamp assay in cells transfected with human Kv1.3.

In another embodiment, the isolated fusion protein of the invention as described herein inhibits in vitro thallium flux with and $IC_{50}$ value of about $2.2 \times 10^{-8}$ M or less in cells transfected with human Kv1.3.

Another embodiment of the invention is an isolated fusion protein comprising a peptide antagonist of Kv1.3 conjugated to a half-life extending moiety via a linker, the peptide antagonist of Kv1.3 having an optional C-terminal extension of four amino acids, wherein
the peptide antagonist of Kv1.3 comprises the amino acid sequence of SEQ ID NOs: 3-110;
the C-terminal extension comprises the amino acid sequence of SEQ ID NOs: 123-268;
the linker comprises the amino acid sequence of SEQ ID NOs: 116 or 119; and
the half-life extending moiety is human serum albumin.

Another embodiment is an isolated peptide antagonist of Kv1.3 comprising
the sequence shown in SEQ ID NO: 1 having a substitution of glycine to isoleucine at position 10 (G10I), and optionally having 1, 2, 3, 4, 5, 6 or 7 additional substitutions; or
an amino acid sequence which is at least 80% identical to SEQ ID NO: 1, further comprising a G10I substitution; and the peptide antagonist of Kv1.3 optionally comprises a C-terminal extension of four amino acids.

Another embodiment is an isolated peptide antagonist of Kv1.3 comprising the sequence GVPXaa$_1$Xaa$_2$VKCXaa$_3$ISRQCXaa$_4$Xaa$_5$PCKDAGMR-FGKCMNGKCHCTPK (SEQ ID NO: 426); wherein
Xaa$_1$ is I or T, Q or E;
Xaa$_2$ is N or D;
Xaa$_3$ is K or R, E, A or Q;
Xaa$_4$ is I, E, L, D, Q, H, V, K or A;
Xaa$_5$ is E K, L, Q, D, V or H; and
the peptide antagonist of Kv1.3 has an optional C-terminal extension of four amino acids.

Another embodiment of the invention is an isolated peptide antagonist of Kv1.3 comprising the sequence GVPXaa$_1$Xaa$_2$VKCXaa$_3$ISRQCXaa$_4$Xaa$_5$PCKDAGM-RFGKCMNGKCHCTPK (SEQ ID NO: 427); wherein
Xaa$_1$ is I or T;
Xaa$_2$ is N or D;
Xaa$_3$ is K or R;
Xaa$_4$ is I or E; and
Xaa$_5$ is E or K; and
the peptide antagonist of Kv1.3 has an optional C-terminal extension of four amino acids.

Another embodiment of the invention is an isolated peptide antagonist of Kv1.3 comprising the sequence of SEQ ID NOs: 3-110.

The OdK2 variant polypeptides and their fusion proteins of the invention may be produced by chemical synthesis, such as solid phase peptide synthesis, on an automated peptide synthesizer. Alternatively, the polypeptides of the invention can be obtained from polynucleotides encoding the polypeptides by the use of cell-free expression systems such as reticulocyte lysate based expression systems, or by standard recombinant expression systems. Those skilled in the art will recognize other techniques for obtaining the polypeptides of the invention.

Generation of the OdK2 variants is typically achieved at the nucleic acid level. The polynucleotides can be synthesized using chemical gene synthesis according to methods described in U.S. Pat. Nos. 6,521,427 and 6,670,127, utilizing degenerate oligonucleotides to generate the desired variants, or by standard PCR cloning and mutagenesis. Libraries of variants can be generated by standard cloning techniques to clone the polynucleotides encoding the OdK2 variants into the vector for expression.

The OdK2 variant fusion proteins are typically made by standard molecular biology approaches.

The OdK2 variants and their fusion proteins are tested for their ability to inhibit Kv1.3 using methods described herein. An exemplary assay is an assay measuring inhibition of thallium influx into the cells in cells overexpressing Kv1.3 using FLIPR® Tetra instrument (Molecular Devices). Another exemplary assay employs electrophysiological recordings to measure ionic flux across the cell membrane using well known patch clamp techniques and described herein.

Another embodiment of the invention is an isolated polynucleotide comprising a polynucleotide encoding the OdK2 variant and OdK2 variant fusion protein of the invention.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or well known tag sequences such as a hexa-histidine or a HA tag which facilitate the purification of fused polypeptides. Certain exemplary polynucleotides are disclosed herein, however, other polynucleotides which, given the degeneracy of the genetic code or codon preferences in a given expression system, encode the antagonists of the invention are also within the scope of the invention. Exemplary polynucleotides are polynucleotides comprising a sequence shown in SEQ ID NOs: 429-430.

Another embodiment of the invention is a vector comprising an isolated polynucleotide encoding the OdK2 variants and their fusion proteins of the invention. The vectors of the invention are useful for maintaining polynucleotides, duplicating polynucleotides, or driving expression of a polypeptide encoded by a vector of the invention in biological systems, including reconstituted biological systems. Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picornaviruses and retroviruses and vectors derived from combinations thereof, such as cosmids and phagemids.

In one embodiment of the invention the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known. An exemplary plasmid-derived expression vector useful for expression of the polypeptides of the invention comprises an *E. coli* origin of replication, an ampicillin resistance (Amp) gene, a CMV promoter, a signal sequence, and a SV40 polyadenlyation site.

Another embodiment of the invention is an isolated host cell comprising a vector of the invention. Exemplary host cells include Archaea cells; bacterial cells such as *Streptococci, Staphylococci, Enterococci, E. coli, Streptomyces*, cyanobacteria, *B. subtilis* and *S. aureus*; fungal cells such as *Kluveromyces, Saccharomyces, Basidomycete, Candida albicans* or *Aspergillus*; insect cells such as *Drosophila* S2 and *Spodoptera* Sf9; animal cells such as CHO, COS, HeLa, C127, 3T3, BHK, HEK293, CV-1, Bowes melanoma and myeloma; and plant cells, such as gymnosperm or angiosperm cells. The host cells in the methods of the invention may be provided as individual cells, or populations of cells. Populations of cells may comprise an isolated or cultured population of cells or cells present in a matrix such as a tissue.

Introduction of a polynucleotide, such as a vector, into a host cell can be effected by methods well known to those skilled in the art. These methods include calcium phosphate transfection, DEAE-Dextran mediated transfection, microinjection, cationic lipid-mediated transfection and electroporation.

Another embodiment of the invention is a method of producing the isolated fusion protein of the invention comprising the steps of culturing the host cell under conditions sufficient for the expression of at least one odK2 variant fusion protein, and recovering the fusion protein expressed by the host cell.

Host cells can be cultured under any conditions suitable for maintaining or propagating a given type of host cell and sufficient for expressing a polypeptide. Culture conditions, media, and related methods sufficient for the expression of polypeptides are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention the expression of the OdK2 variant can be confirmed using a variety of well known methods. For example, expression of a polypeptide can be confirmed using detection reagents, such as antibodies using for example FACS or immunofluorescent techniques, or using SDS-PAGE or HPLC.

Methods of Treatment

Another aspect of the invention is a method of modulating the activity of Kv1.3 in a biological tissue, the method comprising contacting a biological tissue expressing Kv1.3 with a Kv1.3 modulating amount of an OdK2 variant or its fusion protein of the invention, or a pharmaceutically acceptable salt thereof.

OdK2 variants and OdK2 variant fusion proteins of the invention may be utilized in any therapy where it is desired to treat, reduce or alleviate symptoms of Kv1.3-mediated diseases such as inflammatory and autoimmune diseases, diabetes, obesity or cancers.

The methods of the invention may be used to treat an animal patient belonging to any classification. Examples of such animals include mammals such as humans, rodents, dogs, cats zoo animals and farm animals.

The OdK2 variants and/or the OdK2 variant fusion proteins of the invention may be useful for the prophylaxis and treatment of Kv1.3 mediated conditions, such as inflammatory conditions, allergies and allergic conditions, hypersensitivity reactions, autoimmune diseases, severe infections, and organ or tissue transplant rejection. The OdK2 variants and/or the OdK2 variant fusion proteins of the invention are also useful in the preparation of a medicament for such treatment, wherein the medicament is prepared for administration in dosages defined herein.

One embodiment of the invention is method of suppressing T cell activation in a subject having a condition associated with undesired T cell activation, comprising administering to the subject an effective amount of the isolated fusion protein of the invention to suppress T cell activation.

T cell activation can be measured by well known methods, such as measuring reduction of IL-2 production by T cells. "Suppressing T cell activation" as used herein refers to the ability of the OdK2 variants and OdK2 fusion proteins of the invention to inhibit and reduce T cell activation by at least 20%, 30%, 40%, 50%, 60%, 70%, 80%, 90%, or 100%.

In another embodiment, the condition associated with undesired T cell activation is an inflammatory condition, an immune and proliferative disorder, rheumatoid arthritis (RA), ankylosing spondylitis, psoriatic arthritis, osteoarthritis, osteoporosis, uveitis, inflammatory fibrosis, scleroderma, lung fibrosis, cirrhosis, inflammatory bowel disease, Crohn's disease, ulcerative colitis, asthma, allergic asthma, allergies, Chronic Obstructive Pulmonary Diseases (COPD), multiple sclerosis, psoriasis, contact-mediated dermatitis, systemic lupus erythematosus (SLE) and other forms of lupus, diabetes, type I diabetes, obesity, cancer, lupus, restenosis, systemic sclerosis, scleroderma, glomerulonephritis, Sjogren syndrome, inflammatory bone resorption, transplant rejection, or graft-versus-host disease.

The Kv1.3 channel is expressed on all subsets of T cells and B cells, but effector memory T cells and class-switched memory B cells are particularly dependent on Kv1.3 (Wulff et al., J Immunol 173:776, 2004). Kv1.3 is overexpressed in Gad5/insulin-specific T cells from patients with new onset type 1 diabetes, in myelin-specific T cells from MS patients and in T cells from the synovium of rheumatoid arthritis patients (Beeton et al., Proc Natl Acad Sci USA 103:17414-9, 2006), in breast cancer specimens (Abdul et al., Anticancer Res 23:3347, 2003) and prostate cancer cell lines (Fraser et al., Pflugers Arch 446:559, 2003). Positive outcomes in animal models with Kv1.3 blockers have been described in hypersensitivity models to ovalbumin and tetanus toxoid (Beeton et al., Mol Pharmacol 67:1369, 2005; Koo et al., Clin Immunol 197:99, 1999), models for multiple sclerosis such as rat adoptive-transfer experimental autoimmune encephalomyelitis (AT-EAE) model (Beeton et al., Proc Natl Acad Sci USA 103:17414-9, 2006), inflammatory bone resorption model (Valverde et al., J Bone Mineral Res 19:155, 2004), models for arthritis (Beeton et al., Proc Natl Acad Sci 103: 17414, 2006; Tarcha et al., J Pharmacol Exper Therap 342: 642, 2012) and obesity, diabetes and metabolic diseases (Xu et al., Hum Mol Genet 12:551, 2003; Xu et al., Proc Natl Acad Sci 101: 3112, 2004).

Exemplary Kv1.3 mediated conditions that may be treated with the OdK2 variants and/or OdK2 variant fusion proteins of the invention are inflammatory conditions, immune and proliferative disorders, including rheumatoid arthritis (RA), ankylosing spondylitis, psoriatic arthritis, osteoarthritis, osteoporosis, uveitis, inflammatory fibrosis (e.g., scleroderma, lung fibrosis, and cirrhosis), inflammatory bowel disorders (e.g., Crohn's disease, ulcerative colitis and inflammatory bowel disease), asthma (including allergic asthma), allergies, COPD, multiple sclerosis, psoriasis, contact-mediated dermatitis, systemic lupus erythematosus (SLE) and other forms of lupus, diabetes, type I diabetes, obesity and cancer, lupus, restenosis, systemic sclerosis, scleroderma, glomerulonephritis, Sjogren syndrome, inflammatory bone resorption, transplant rejection, and graft-versus-host disease.

Administration of the OdK2 variants and/or OdK2 variant fusion proteins of the invention to the animal models of a particular disease can be used to evaluate the use of the OdK2 variants and/or OdK2 variant fusion proteins to ameliorate symptoms and alter the course of diseases. Animal models that can be used are well known, and include models described above and models such as collagen-induced arthritis (CIA) model, diet-induced obesity model, the 2,4,6-trinitrobenesulfonic acid/ethanol (TNBS)-induced colitis model or the oxazalone model, which induce chronic inflammation and ulceration in the colon (Neurath et al., Intern Rev Immunol 19:51-62, 2000), the adoptive transfer model of naïve CD45RB$^{high}$ CD4 T cells to RAG or SCID mice, the donor naïve T cells attack the recipient gut causing chronic bowel inflammation and symptoms similar to human inflammatory bowel diseases (Read and Powrie, Curr Protoc Immunol Chapter 15 unit 15.13, 2001), ovalbumin challenge model and methacholine sensitization models (Hessel et al., Eur J Pharmacol 293:401-12, 1995).

Pharmaceutical Compositions

The "therapeutically effective amount" of the OdK2 variant and/or OdK2 variant fusion protein effective in the treatment of conditions where suppression of Kv1.3 activity is desirable can be determined by standard research techniques. For example, the dosage of the agent that will be effective in the treatment of an inflammatory condition or autoimmune disease such as lupus, multiple sclerosis or psoriasis can be determined by administering the agent to relevant animal models, such as the models described herein.

In addition, in vitro assays can optionally be employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

The mode of administration for therapeutic use of the OdK2 peptide variants and/or OdK2 variant fusion proteins of the invention may be any suitable route that delivers the variant to the host. Pharmaceutical compositions of these variants are particularly useful for parenteral administration, e.g., intradermal, intramuscular, intraperitoneal, intravenous, subcutaneous or intranasal.

The OdK2 variants and/or OdK2 variant fusion proteins of the invention may be prepared as pharmaceutical compositions containing an effective amount of the variant as an active ingredient in a pharmaceutically acceptable carrier. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the OdK2 variants and/or OdK2 variant fusion proteins of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected.

Thus, a pharmaceutical composition of the invention for intramuscular injection could be prepared to contain 1 ml sterile buffered water, and between about 1 ng to about 100 mg, e.g. about 50 ng to about 30 mg or more preferably, about 5 mg to about 25 mg, of the OdK2 variants and/or their fusion proteins of the invention. Similarly, a pharmaceutical composition of the invention for intravenous infusion could be made up to contain about 250 ml of sterile Ringer's solution, and about 1 mg to about 30 mg and preferably 5 mg to about 25 mg of an antagonist of the invention. Actual methods for preparing parenterally administrable compositions are well known and are described in more detail in, for example, "Remington's Pharmaceutical Science", 15th ed., Mack Publishing Company, Easton, Pa.

The OdK2 variants and/or the OdK2 variant fusion proteins of the invention can be lyophilized for storage and reconstituted in a suitable carrier prior to use. This technique has been shown to be effective with conventional protein preparations and art-known lyophilization and reconstitution techniques can be employed.

The present invention will now be described with reference to the following specific, non-limiting examples.

Materials and Methods

Kv Channel Expression Constructs and Cell Lines.

cDNAs encoding the various Kv channels and chimeric constructs were cloned using routine methods into mammalian expression vectors. cDNAs cloned and expressed were those encoding human Kv1.3 (hKv1.3) (SEQ ID NO: 418), human Kv1.1 (hKv1.1) (SEQ ID NO: 420), human Kv1.2 (hKv1.2) (SEQ ID NO: 419), human Kv1.5 (hKv1.5) (SEQ ID NO: 421), hKv1.3 E3 loop/hKv1.5 chimera (having human Kv1.5 amino acids 1-455 and 496-613, and Kv1.3 E3 loop amino acids 456-495) (Kv1.3 EC3 loop chimera), hKv1.1 E3 loop/hKv1.5 chimera with N terminal His tag (having His tag amino acids 1-9, hKv1.5 amino acids 10-472 and 513-63, and hKv1.1 E3 loop amino acids 473-512) (Kv1.1 EC3 loop chimera), rat Kv1.3 (rKv1.3) (SEQ ID NO: 422), rat Kv1.1 (rKv1.1) (SEQ ID NO: 423), cynomolgus monkey (*Macaca fascicularis*) channel cynoKv1.3 (SEQ ID NO: 424), hKv1.3/hKv1.5 tail chimera (having human Kv1.5 amino acids 1-250 and 497-593, and Kv1.3 amino acid sequences 251-496 (Kv1.3 tail chimera), and hKv1.1/hKv1.5 tail chimera (having human Kv1.5 amino acids 1-250 and 492-588, and Kv1.1 amino acid sequences 251-491 (Kv1.1 tail chimera). For channel expression in HEK cells, Kv genes were cloned into a CMV promoter driven expression vector encoding the neomycin resistance marker. HEK 293-F (Invitrogen, Carlsbad, Calif.) cells were stably transfected and cultured in DMEM 10% FBS and 600 μg/ml Geneticin selection media to generate clonal cell lines that expressed Kv channels using standard techniques. For CHO stable expression, CHO-TREx cells (Invitrogen) were stably transfected with pcDNA4/TO-Kv1.x using standard techniques to generate clonal cell lines that expressed each potassium channel in a tetracycline-inducible manner. The culture medium was Ham's F-12 supplemented with 10% fetal bovine serum, 2 mM L-glutamine, 5 μg/ml blasticidin and 200 μg/ml zeocin. In some experiments, transient transfection using Lipofectamine 2000 in CHO cells were used. For electrophysiological experiments, cells was co-transfected with an expression vector expressing a truncated CD4 for expression control (pMACs4.1, Milteni Biotech). Assays were performed 24-48 hours after transfection.

Protein Expression and Purification.

The chimera library was expressed as peptide-Fc fusions or a peptide-HSA fusion. The library was initially transfected and expressed in HEK 293-E cells in 48-well or 96-well format. The cells were cultured in DMEM, 10% FBS and 250 μg/ml of Geneticin for selection. For 48-well expression 0.5 ml/well of 3.0×10⁵ cells/ml were plated in the 48-well plates. The library was transfected using Lipofectamine 2000 using routine methods utilizing 300 ng of plasmid DNA, 25 μl OptiPRO™ SFM media, and 2.4 μl Lipofectamine 2000 (Invitrogen, Carlsbad, Calif.). The next day, the transfection media was aspirated and 0.5 ml of 293 FreeStyle™ media (Invitrogen, Carlsbad, Calif.) was added to each well. The cells were then incubated for an additional 96 hours before the supernatant was collected and filtered through a 0.2 μm filter (Varian).

For 96-well transfection the cells were spun down at 500×g for 5 min, the supernatant was removed and the cells were re-suspended in 293 FreeStyle™ media and plated into a 96-well plate at 0.6×10⁶ cells/ml in 0.2 ml/well. The library was transfected with the same method as the 48-well transfection.

HEK 293-F cells were used for all small and pilot scale transfections.

Small scale expressions of peptide-Fc fusions were batch purified using Protein A Sepharose 4FF resin using routine methods. Briefly, 20 ml of clarified expression supernatant was mixed with about 0.5 ml of resin equilibrated in DPBS, pH 7.2, and mixed at room temperature for no less than 1 hour. The Protein A resins were washed with 1 ml DPBS, pH 7.2, and the bound protein was eluted with 450 μl of 0.1 M sodium acetate, pH 3.0, neutralized with 50 μl of 2M tris, pH 7.0 and dialyzed against 1×DPBS, pH 7.2 overnight at 4° C.

Pilot scale expressions were affinity purified on the AKTA Xpress™ chromatography system (GE Healthcare). Expression supernatants from transiently transfected HEK293-F cells were harvested 4 days after transfection, clarified by centrifugation at 6000 rpm and filtered (0.2 μm PES membrane, Corning, Acton, Mass.). The relative amount of peptide-Fc fusion was determined with the Octet instrument (ForteBio) using a control toxin-Fc fusion protein spiked into spent medium to generate the standard curve. Samples were then diluted with 10×PBS, pH 7.0 to a final concentration of 1×PBS, pH 7.0 and again filtered (0.2 μm PES membrane). Diluted supernatants were loaded onto a HiTrap MabSelect Sure Protein A column (GE Healthcare) pre-equilibrated with PBS, pH 7.0, at a relative concentration of ~10 mg protein per ml of resin. After loading, the column was washed with PBS, pH7.0 and protein eluted with 10 column volumes of 0.1 M Na-Acetate, pH 3. The protein fractions were neutralized immediately by elution into tubes containing 2.0 M Tris, pH 7 at 20% fraction volume. Peak fractions were pooled and concentrated using centrifugal ultrafiltration devices (Millipore) with 10k MWCO membranes. Concentrated samples were passed over a Superdex 200 (16/60) column (GE Healthcare) equilibrated and run in PBS, pH7.0 using an AKTA FPLC. Peak fractions were analyzed by non-reducing SDS-PAGE and fractions containing monomeric protein were pooled. Protein concentrations were determined by absorbance at 280 nm and 310 nm on a BioTek SynergyHT™ spectrophotometer. If necessary, the purified proteins were concentrated with a 10K MWCO centrifugal concentrator (Millipore). The quality of the purified proteins was assessed by SDS-PAGE, analytical size exclusion HPLC (Dionex HPLC system), and endotoxin levels measured (LAL assay). Purified proteins were stored at 4° C.

For peptide-HSA fusions, the supernatants were harvested, clarified and filtered through a 0.2 μm filter. Before loading onto a pre-equilibrated 1 mL HisTrap column, 10×DPBS was added to a final concentration of 1×. Protein was eluted using a step gradient of imidazole. Fractions containing fusions were collected and analyzed by SDS-PAGE. Fractions containing the protein of interest were pooled and concentrated and run on a Superdex 200 26/60 column. Again, fractions were collected and analyzed by SDS-PAGE. Fractions containing the monomer and dimer of peptide-HSA fusions were pooled separately for the final product. The purified protein was analyzed as described above and stored at 4° C.

Peptide Fusion Protein Direct Binding Assay ("Binding Assay").

Peptide-Fc Fusion Proteins.

All cell culture reagents were obtained from Invitrogen. Adherent HEK 293F cells stably transfected with plasmids expressing various Kv channels were cultured in DMEM supplemented with 10% FBS and 600 µg/ml Geneticin. Single cell suspensions of Kv channel HEK cells were prepared by rinsing adherent cultures with 1×PBS, then rinsing cultures with 0.25% trypsin EDTA and resuspending cells in cold 1×PBS supplemented with 2% FBS (FACS buffer) to a final density of $2\times10^6$ cells/ml, and dispensing 100 µl/well into 96 well V bottom polypropylene plates (Costar). From this point on the procedure was performed on ice or at 4° C. Cells were centrifuged at 450×g for 2 minutes and supernatants were decanted. 100 µl of peptide-Fc samples in spent Freestyle 293 media or in FACS buffer normalized to 16 nM were added to the cell pellets in designated wells and mixed. To differentiate specific binding and non-specific background, a 10-fold molar excess of synthetic ShK peptide (Bachem) was added to negative control reactions to compete binding of the peptide-Fc fusion protein. Reactions were incubated for 60-90 minutes at 4° C. Cells were washed in 200 µl FACS buffer, and then incubated for 1 hour at 4° C. with 100 µl of Goat Fab'2 anti human Fc Cy5 conjugated antibody (Jackson ImmunoResearch Inc.) diluted 1:200 in FACS buffer. Cells were washed in 200 µl FACS buffer, and then resuspended with 100 µl of BD Cytofix™ fixation buffer (BD Biosciences) and stored over night at 4° C. Reactions were read on the FACSArray 96 well auto-sampler flow cytometer (BD Biosciences). Data was analyzed in FlowJo software (Treestar) to obtain geometric mean fluorescence intensities (Geo. MFI) for each reaction. For primary screening binding assays Geo. MFIs for each variant were compared directly to the transiently transfected wild type Odk2-Fc fusion (KV1C2) control and reported as % parent.

Peptide-HSA Fusion Proteins.

The assays were performed identically to the direct binding assay for the peptide-Fc fusions except for following: cells were suspended to a final density of $1\times10^6$ cells/ml before dispensing 100 µl/well into 96 well V bottom polypropylene plates (Costar), and 50 µl of peptide-HSA fusion samples were added to the cell. The HSA fusions were detected using 50 µl of goat anti-human HSA biotin conjugate (AbCam cat #ab40378) diluted to 2 µg/ml and premixed with streptavidin-PE conjugate ( ) 1:200 in FACS buffer. Cells were washed in 150 µl FACS buffer, resuspended in 50 µl of BD Cytofix™ fixation buffer (BD Biosciences) and incubated at 4° C. for 30 minutes. Reactions were read and data analyzed as described above. For primary screening binding assays Geo. MFIs for each variant were compared directly to the control KV1D261_26 fusion protein (peptide 261 conjugated to HSA via $GS(G_4S)_8$ linker (SEQ ID NO: 120) and reported as % Binding.

Competitive Binding Assay ("Competitive Binding").

All cell culture reagents were obtained from Invitrogen. Adherent HEK 293F cells stably transfected with Kv channel expression constructs were cultured in DMEM supplemented with 10% FBS and 600 µg/ml Geneticin. Single cell suspensions of Kv channel HEK cells were prepared by rinsing adherent cultures with 1×PBS, then rinsing cultures with 0.25% trypsin EDTA, then resuspending cells in cold 1×PBS supplemented with 2% FBS (FACS buffer) to a final density of $1\times10^6$ cells/ml, and dispensing 100 µl/well into 96 well V bottom polypropylene plates (Costar). From this point on the procedure was performed on ice or at 4° C. Cells were centrifuged at 450×g for 2 minutes and supernatants were decanted. 45 µl of peptides or peptide fusion protein samples in spent Freestyle 293 media or in FACS buffer were added to the cell pellets in designated wells and mixed. Reactions were incubated for 30 minutes at 4° C. 5 µl of 100 nM Agitoxin-2-Cys-TAMRA (Alomone labs) in cell culture media or FACS buffer were added to each well followed by mixing, and reactions were incubated for 60 minutes at 4° C. 200 µl of FACS buffer was added to each well as a wash step, and cells were centrifuged at 450×g for 2 minutes and supernatants were decanted. Cells were resuspended with 50 µl of FACS buffer and reactions were read on the FACSArray 96 well auto-sampler flow cytometer (BD Biosciences). Data was analyzed in FlowJo software (Treestar) to obtain geometric mean fluorescence intensities (Geo. MFI or GMFI) for each reaction. For concentration response curves, the change in Geo. MFI values across a range of concentrations for each compound were plotted in Graphpad Prism and $IC_{50}$ and Ki values derived using nonlinear regression with a sigmoidal dose-response (variable slope) curve. For calculating Ki, an Agitoxin-2-Cys-TAMRA Kv1.3 KD value of 0.20 nM was assigned (David Triggle (eds). Voltage-Gated Ion Channels as Drug Targets, Volume 29, Page 216, Tab. 7.2.2).

Thallium Flux Assay.

The Kv constructs were stably expressed in HEK293F under G418 selection. Culture medium was HyQ DME/high glucose supplemented with 10% FBS and 600 µg/mL G418. Cells were plated at 10K cells per well into poly-lysine coated 384-well microtiter plates then incubated for 12-36 hours at 37° C. Cell plates were washed with assay buffer using a Biotek EL405 (4 cycles, aspirate to 25 µL/well, then add 100 µL/well). The assay buffer contained (in mM): 130 mM NaCl, 4 mM KCl, 2 mM $CaCl_2$, 1 mM $MgCl_2$, 10 mM HEPES, 5 mM glucose. FluxOR dye (Invitrogen) was dissolved per manufacturers' instructions in assay buffer plus 2 mM probenecid, and then added to the cells. Cells were stained for 30 minutes at room temperature in the dark. The dye was then washed off with assay buffer. Test compounds were prepared at 2× the test concentration in assay buffer plus 0.2% bovine serum albumin (BSA) and 2 mM probenicid. After adding 25 µL/well of the test compound solution, the cells were incubated for 30 minutes at room temperature in the dark. Thallium dye fluorescence was monitored in Tetra (Molecular Devices) as the cells were challenged by adding 20 µL/well of stimulus buffer. The stimulus buffer contained 180 mM HEPES, 90 mM KOH, 2 mM $CaCl_2$, 1 mM $MgCl_2$, 5 mM glucose, 1 mM $Tl_2SO_4$. The fluorescence change was measured 20 seconds after adding the agonist. Data were normalized to the average responses of control wells (N=16 each of 10 nM ShK for full inhibition controls, and buffer-only for zero inhibition controls).

T Cell Inhibition Assay ("T Cell Inhibition Assay").

Inhibition of IL-2 secretion was used as an indicator for T cell inhibition. Cryopreserved purified primary normal human $CD4^+$ and $CD8^+$ T cells (AllCells LLC) were thawed and suspended in RPMI 1640 (Invitrogen) supplemented with 1% normal human A/B serum (Valley Biomedical Prod & Srv Inc.) at a final density of $2\times10^6$ cells/ml, and 100 µl of cells were dispensed into 96 well flat bottom tissue culture plates (NUNC). For peptide-HSA fusion proteins, purified normal human serum albumin (SIGMA) was added to the cell culture media at a final concentration of 3% in order to maintain a constant HSA concentration throughout the concentration-response experiments. Peptide fusion proteins and controls were diluted in cell culture media, and 50 µl/well were added to T cell cultures and incubated for 30 minutes at 37° C./5% $CO_2$. T cells were activated using anti-human CD3/CD28 T cell expansion beads (Miltenyi Biotec) diluted in cell culture media at a 1:1 bead to cell ratio. Cultures were incubated for ~16 hours at 37° C./5% $CO_2$, and the supernatants were harvested into 96 well V bottom polypropylene plates (Costar) and clarified by centrifugation. Clarified supernatants were analyzed for IL-2 levels by a chemiluminescent immunoassay derived from the human IL-2 Quantikine Kit (RnD Sytems). Final IL-2 levels were plotted in Graphpad Prism, and $IC_{50}$ values were derived using nonlinear regression with a sigmoidal dose-response (variable slope) curve fit. Some experiments were done at single point 5 nM, 100 nM or 250 nM peptide fusion protein concentration.

Tetanus Toxoid (TTX) T cell Assay.

Human PBMC were purified from tetanus toxoid vaccinated healthy donor blood by step gradient centrifugation using Ficoll Pague (GE Healthcare Life Science). PBMC at $10^6$ cells/well were stimulated for 3 days in 96 well flat bottom culture plate with 3 ug/ml tetanus toxoid (Univ. of Massachusetts Biologic) in RPMI medium supplemented with 2% human serum, 2 mM glutamine, 1 mM sodium pyruvate, 10 mM HEPES, 1 mM MEM nonessential amino acid solution, and 100 U/ml each of penicillin G and streptomycin (Life Technologies). Culture supernatants were collected on day 2 culture and cell proliferation was measured by overnight pulse with 1 uCi/well of $^3$H-thymidine (Perkin Elmer). Proliferating cells with incorporated radioactive thymidine were harvested onto glass fiber filter plates (Perkin Elmer) and soaked in scintillant (Perkin Elmer) for counting of radioactivity using a Topcount (Packard). Cytokines in supernatants were measured with the MSD detection technology (Meso Scale Discovery).

Electrophysiology.

Transfected CHO or HEK cells, $CD4^+$ or $CD8^+$ T cells were used in electrophysiology. Cells were plated at low density onto glass coverslips. On the day of the experiment, glass cover slips were placed in a bath on the stage of an inverted microscope and perfused (approximately 1 ml/min) with extracellular solution of the following composition: 137 mM NaCl, 2 mM $CaCl_2$, 5.4 mM KCl, 1 mM $MgCl_2$, 5 mM glucose, and 10 mM HEPES, 0.1% bovine serum albumin, pH 7.4. Pipettes were filled with an intracellular solution of the following composition: 40 mM KCl, 100 mM KF, 2 mM $MgCl_2$, 10 mM EGTA, 10 mM HEPES, pH 7.3 to 7.4, and had a resistance of 2 to 4 MΩ. All recordings were made at room temperature (22-24° C.) using a Multiclamp 700A amplifier and pClamp 9 software (Axon Instruments). Transiently transfected CHO cells were identified using anti-CD4 coated beads (Dynabeads, InVitrogen). Outward potassium currents were measured using the whole-cell configuration of the patch-clamp technique at a test potential of 20-40 mV from a holding potential of −80 mV. The liquid junction potential was calculated to be 7.1 mV at 20° C. and voltage commands were not corrected. Current records were acquired at 2-5 KHz and filtered at 1-2 KHz. Currents were elicited once every 20 s and were allowed to stabilize for 5-10 mins prior to recording. Compounds were applied using an SF-77B Fast-Step Perfusion device (Warner Instruments). 1-4 concentrations of compound were tested per cell.

Data Analysis:

Concentration- or dose-response data were fitted by non-linear regression (Graph Pad Prism, version 4.0) using the following four parameter general logistic equation:

Response=Basal+(Max−Basal)/[1+ $10^{(log\ EC_{50}-Log\ Agonist)Hill\ slope}$]

Potency was expressed as the −log 10 of the concentration producing 50% maximal effect ($pIC_{50}$ or $pEC_{50}$).

Peptide Synthesis.

Fmoc-Lys(Boc)-Wang resin (0.47 mmol/g substitution) was obtained from Peptide International and pseudoproline dipeptide, Fmoc-Ile-Ser(ΨMeMe pro)-OH was obtained from Novabiochem. All other amino acids were obtained from Applied Biosystems (ABI) or Anaspec. Reagents for automated solid phase peptide synthesis (SPPS) were obtained from ABI. Other reagents required for chemical synthesis were purchased from Sigma/Aldrich. Peptide synthesis was performed on Fmoc-Lys(Boc)-Wang resin (222 mg, 0.104 mmol) via SPPS using an ABI Model 433A automated peptide synthesizer. The standard 0.1-mmole-scale FastMoc MonPrevPeak protocols for HBTU/HOBt/DIEA activation were used according to the manufacturer's protocol. Pseudoproline dipeptide, Fmoc-Ile-Ser($\Psi^{MeMe}$pro)-OH, was incorporated at the position shown in bold and underlined in the sequence GVPINVKCKIS-RQCIEPCKDAGMRFGKCMNGKCHCTPK-resin (SEQ ID NO: 42). The amino-acid side-chain functionality was protected as follows: Arg(Pmc), Asn(Trt), Asp(OtBu), Cys (Trt), Glu(OtBu), Gln(Trt), Lys(Boc), Ser(tBu) and Thr (tBu).

Peptide was cleaved from the resin in (TFA (20 mL), phenol (1.5 g), 1,2 Ethanedithiol (4.0 mL) thioanisole (1.0 mL), water (1.0 mL) and triisopropylsilane (1.0 mL)) for six hours at ambient temperature. The resin was removed via filtration and rinsed with additional TFA (2 mL). The filtrates were combined and the peptide was precipitated with precooled ethyl ether (400 mL). The peptide isolated by filtration, washed with diethyl ether, and dried in vacuo gave 370.0 mg of crude, linear product: (GVPINVKCKIS-RQCIEPCKDAGMRFGKCMNGKCHCTPK; SEQ ID NO: 42). The crude linear peptide was oxidized at a peptide concentration 100 µg/mL in 0.1 M Tris-HCL, 1.0 M Guanidine-HCL, 1.0 mM EDTA, 3.0 m; M glutathione-reduced and 0.3 mM Glutathione-oxidized at ambient temperature. The reaction was stopped after 25 h by drop wise addition of glacial acetic acid to reduce the pH to 3.9 and the peptide was frozen and lyophilized. The crude peptide was purified by Vydac C-18 RP-HPLC. Analytical RP-HPLC, capillary electrophoresis and LC/MC confirmed the purity and molecular mass.

Example 1

Characterization of Wild Type OdK2 and OsK1 Peptides and their Fusion Proteins

Wild type OdK2 (SEQ ID NO: 1) and OsK1 (SEQ ID NO: 2) peptides were cloned and expressed as IgG4 Fc fusion proteins using the linker $GS(G_4S)_4$ (SEQ ID NO: 119) using routine methods and as described above. The resulting fusion proteins were named KV1C2 (OdK2-Fc fusion) and KV1N2 (OsK1-Fc fusion), respectively. Native OdK2 peptide was isolated and purified from the venom of the Iranian scorpion Odonthobuthus was obtained from Professor Jan Tytgat at the University of Leuven, and recombinant OsK1 peptide from Alomone labs. The native peptides and their fusion proteins were characterized for their binding to Kv1.3, Kv1.3 potency and selectivity using electrophysiology, ability to inhibit T cell activation, and in pharmacokinetic studies.

Binding to Kv1.3 Expressing Cells

Figure 2B:
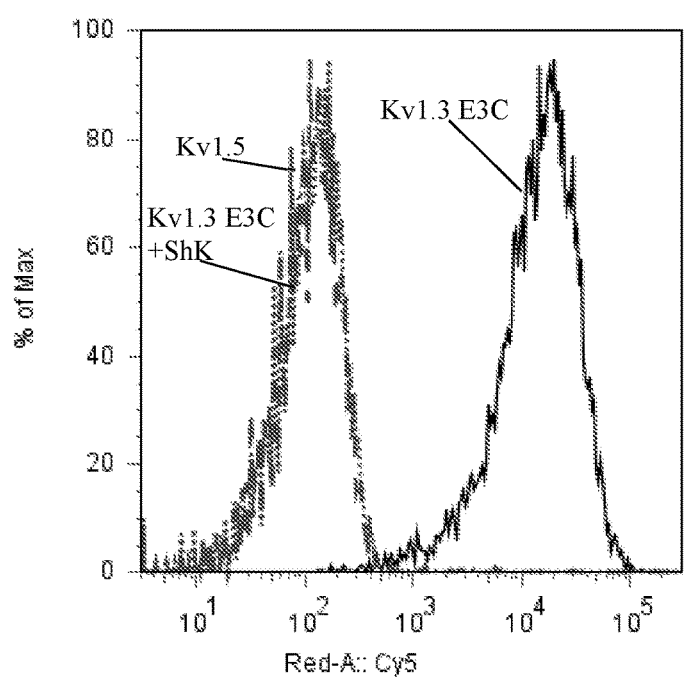

Binding assays were conducted as described above in stable cells expressing the hKv1.3 EC3 loop chimera. KV1C2 (OdK2-Fc fusion) produced a signal in the FACS assay that was 12.8-fold over background and KV1N2 (OsK1-Fc fusion) produced signal 133.0-fold over background (FIG. 2), suggesting a high level of binding to the expressed Kv1.3 channel. The binding appeared specific since no binding to human Kv1.3 EC3 loop chimera expressing cells was observed in the presence of a 10-fold excess ShK. The binding was also selective, since KV1C2 (OdK2-Fc fusion) and KV1N2 (OsK1-Fc fusion) did not bind to human Kv1.5 expressing cells.

Electrophysiology

Whole-cell patch clamp studies were performed on CHO cells transfected with human Kv1.3, Kv1.1, Kv1.2 and Kv1.5 ion channels. Osk1 and Odk2 both potently inhibited Kv1.3 currents. OsK1 peptide was significantly more potent than OdK2 against Kv1.3, but the fold selectivity over Kv1.1 was similar for the two peptides. KV1C2 (OdK2-Fc fusion) and KV1N2 (OsK1-Fc fusion) were about 30-100-fold less potent towards Kv1.3 when compared to the native peptides. However, KV1C2 selectivity (calculated as Kv1.1 $IC_{50}$ divided by Kv1.3 $IC_{50}$) was improved about 3-4 fold relative to the native peptide. The $IC_{50}$ values and selectivity ratios determined in by electrophysiology are shown in Table 1.

TABLE 1

| | Electrophysiology | | | CD4+ | CD8+ |
| --- | --- | --- | --- | --- | --- |
| Protein | Kv1.3 $IC_{50}$ (nM) | Kv1.1 $IC_{50}$ (nM) | Fold selectivity** | T cell inhibition $IC_{50}$ (nM) | T cell inhibition $IC_{50}$ (nM) |
| OdK2 | 0.10 | 1.90 | 19 | NA | NA |
| OsK1 | 0.01 | 0.21 | 15 | 0.03 | 0.03 |
| OdK2-linker-Fc* | 13.00 | 865.00 | 67 | 69.92 | 69.54 |
| OsK1-linker-Fc* | 0.30 | 2.00 | 7 | 2.79 | NA |

Figure 3:
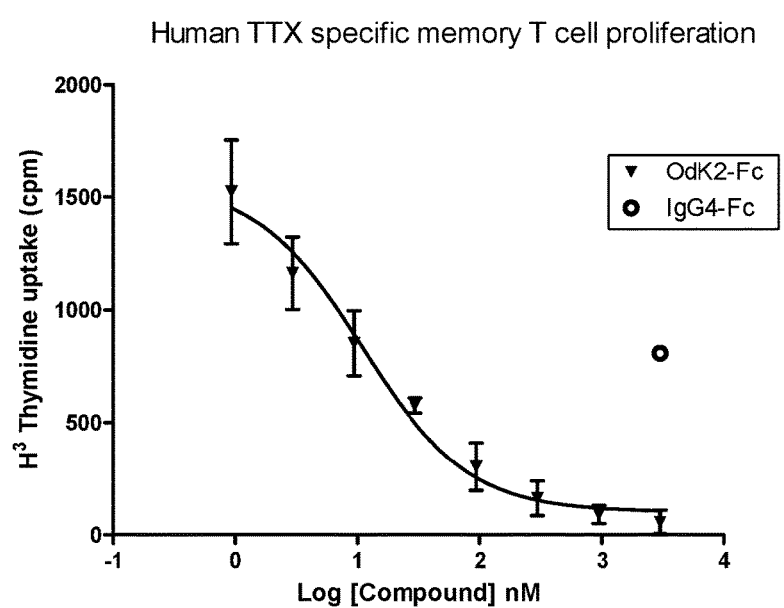
FIG. 3. Inhibition of memory T cell proliferation by KV1C2 (OdK2-Fc fusion) (▼). Each data point is the mean±SD of triplicate reactions. Negative control IgG4 Fc (○) did not inhibit T-cell proliferation.
Figure 5A:
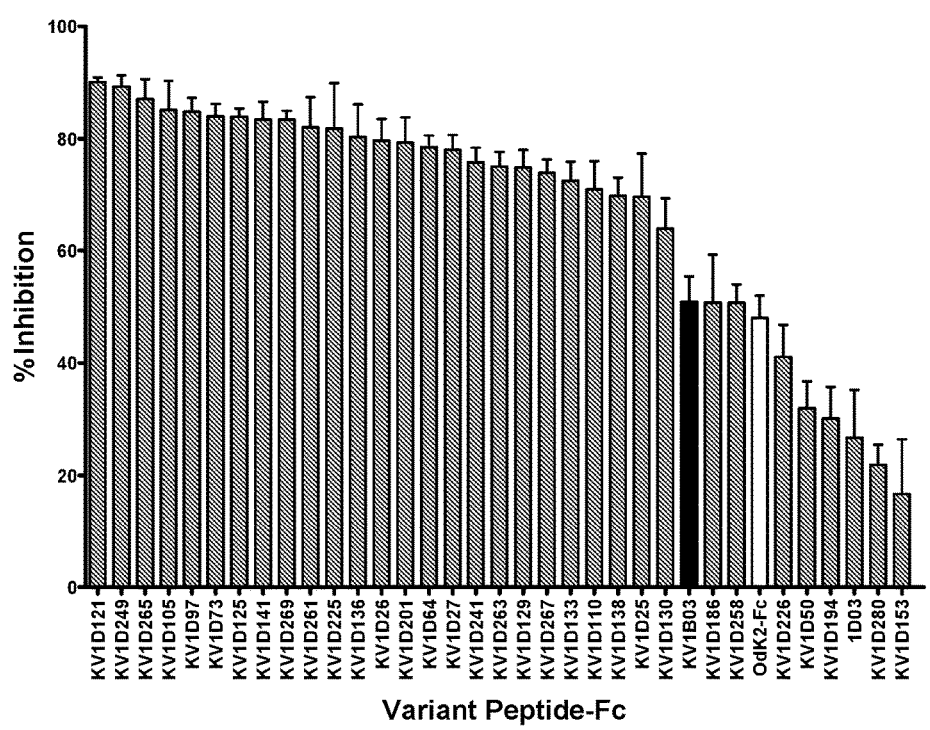
FIG. 5. A) Inhibition of T cell activation by purified Odk2 chimera Fc fusion proteins at single 100 nM concentration. KV1B03 (■) is identical to KV1C2 (OdK2 Fc fusion) (□). B) Concentration dependent inhibition of T cell activation by KV1D261. Negative control IgG4 Fc did not inhibit T-cell IL-2 production. C) Correlation between binding to Kv1.3 E3C cells and T-cell inhibition for select variants.
Figure 5B:
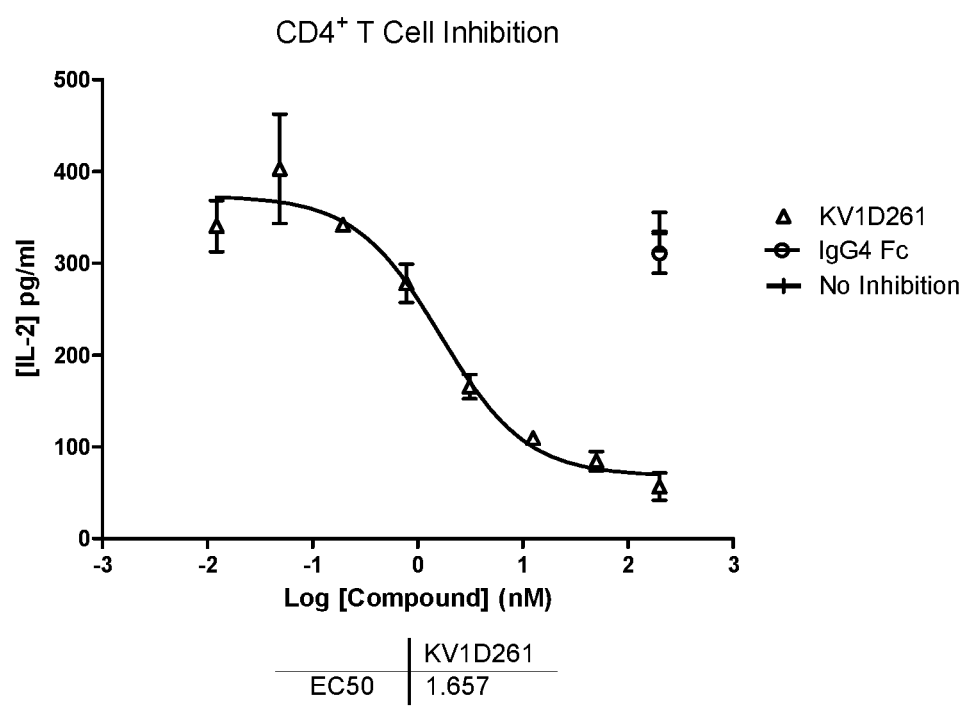
Figure 5C:
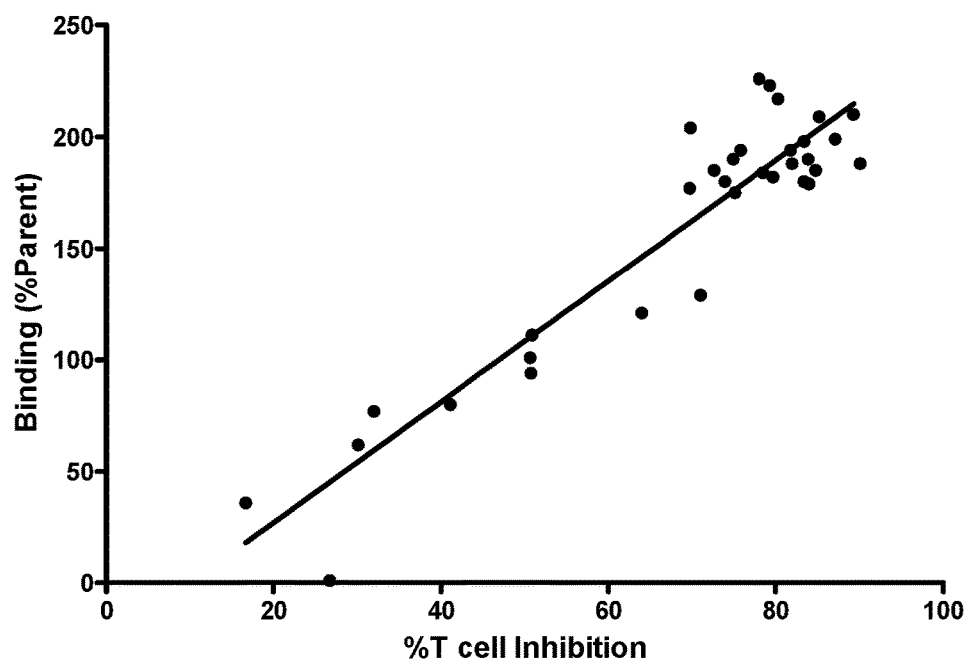

*Linker = GS(G4S)4, SEQ ID NO: 119
**$IC_{50}$(Kv1.1)/$IC_{50}$(Kv1.3)
NA = not done Inhibition of T-Cell Activation KV1C2 (OdK2-Fc fusion) blocked Kv1.3 cellular currents in the Jurkat T cell line, primary CD4+ human T cells (isolated from normal human donors), and Kv1.3 transfected HEK and CHO cells. KV1C2 (OdK2-Fc fusion) also blocked cytokine production from primary human CD4+ and CD8+ T cells activated with anti-CD3/CD28. KV1N2 (OsK1-Fc fusion) blocked Kv1.3 cellular currents in the Jurkat T cell line, competed agitoxin2-cys-TAMRA binding to cells expressing the hKv1.3 EC3 loop chimera, inhibited thallium flux from cells expressing the hKv1.3 EC3 loop chimera, and was tested for its ability to inhibit CD4+ T cell activation. Table 1 shows the obtained $IC_{50}$ values from manual patch-clamp electrophysiology. KV1C2 (OdK2-Fc fusion) also inhibited T cell proliferation upon activation with mitomycin C treated autologous antigen presenting cells displaying tetanus toxoid antigen in an assay described above (FIG. 3).

Half Life of OdK2-Fc Fusion Protein

Sparague Dawley Rats were dosed with KV1C2 (OdK2-Fc fusion) through intravenous bolus administration of a 2 mg/ml stock in 1xPBS pH7.0 at 5 ml/kg for a final dose of 10 mg/kg. The plasma concentrations were determined by an anti-Fc ELISA or by FACS as described above. The KV1C2 half-life ($T_{1/2}$) in rats was 60 hours.

Example 2

Generation of OdK2 Chimera Peptide Fc Fusions ("OdK2/Osk1 Chimera Library" or "KV1C2L1")

The native OdK2 and OsK1 toxin peptide sequences have a high degree of sequence similarity, with divergence at 9 amino acid residues (FIG. 1). In order to create peptide variants having enhanced Kv1.3 potency and Kv1.x subtype selectivity, a combinatorial library of peptide-linker-Fc variants using a GS(G4S)4 linker (SEQ ID NO: 119) was generated in which the OdK2 peptide amino acid sequence was variegated at 8 of 9 positions the OdK2 sequence diverged from OsK1 (positions 3, 4, 5, 9, 10, 12, 16 and 20) in OdK2, SEQ ID NO:1). Position 15 was not included in the library diversification, because of the similarity between isoleucine and leucine at this position. The positions were diversified using OdK2 and OsK1 amino acid residues present at each position. Thus, position 3 was diversified with PI, and positions 4, 5, 9, 10, 12, 16 and 20 with TI, DN, RK, GI, RP, EQ, and KD, respectively. The library design also incorporated six variants with a lysine substitution at position 16, based on previous reports that this mutation increased the potency of the OsK1 peptide (Mouhat et al., Biochem J 385:95-104, 2005), and a glutamine substitution at position 38 as a result of an initial discrepancy in the correct OdK2 amino acid sequence. Thus, the OdK2/Osk1 chimera library consisted of 264 total members including the lysine substitution variants, the OdK2 K38Q variant, and both parent molecules KV1C2 (Odk2 fusion) and (OsK1 fusion). Position numbering is according to the native OdK2 peptide sequence of SEQ ID NO: 1.

The library was generated and expressed using routine molecular biology methods and as described above.

The library was screened using crude supernatants for binding to hKv1.3 using a HEK cell line transfected with the hKv1.3 EC3 loop chimera, and for selectivity by binding to a HEK cell line transfected with the hKv1.1 EC3 loop chimera channel as described above. In the primary screen, binding was measured as % binding of control KV1C2 (% Binding) and selectivity as a ratio of % Binding to Kv1.3 to % Binding to Kv1.1. FIG. 4 shows the amino acid sequences, % Binding, selectivity, and $IC_{50}$ values from thallium flux assays for select variants obtained from the OdK2/Osk1 chimera library (KV1C2L1 library) as well as from the amino acid scan library (KV126L1 library) described in Example 4.

Select fusion proteins demonstrating ≥80% binding to Kv1.3 and ≥1.3 fold selectivity over Kv1.1 when compared to the parent KV1C2 (OdK2-Fc fusion) were characterized further.

Example 3

Characterization of OdK2 Chimera Peptide Fc Fusions

Select OdK2 chimera peptide Fc fusion proteins identified in Example 2 were purified as described above and characterized in secondary binding assays, electrophysiology and T cell inhibition assays.

Electrophysiology

Select variants were assessed for their potency and selectivity in whole cell patch-clamp studies using stably transfected CHO as described above. Inhibition of human Kv1.3 or human Kv1.1 was assessed at a single concentration (1 nM for Kv1.3 or 100 nM for Kv1.1) of purified variant (Table 2). Selected variants had significantly increased activity against Kv1.3 but similar activity against Kv1.1 relative to the parent KV1C2.

$IC_{50}$ values were derived from manual patch-clamp electrophysiology studies for select OdK2 chimera peptide Fc fusions using CHO cells stably transfected with either human Kv1.3 or Kv1.1 as described in materials and methods. Fold selectivity was calculated as a ratio of $IC_{50}$ (Kv1.1) to $IC_{50}$ (Kv1.3). Table 3 shows $IC_{50}$ values for select variants and the parent OdK2 and OsK1 fusions KV1C2 and KV1N2, respectively.

TABLE 2

| Fusion protein | Kv1.3 % Inhibition @ 1 nM | Kv1.1 % Inhibition @ 100 nM |
|---|---|---|
| KV1D197 | 83 | 37 |
| KV1D37 | 67 | 40 |
| KV1D267 | 64 | 49 |
| KV1D229 | 85 | 54 |
| KV1D261 | 85 | 61 |
| KV1D161 | 76 | 63 |
| KV1D69 | 86 | 64 |
| KV1C2* | 36 | 40 |
| KV1D280 | — | 97 ** |

*parent (OdK2-Fc fusion)
** fusion protein at 10 nM

TABLE 3

| Fusion protein | Kv1.3 $IC_{50}$ (nM)* | Kv1.1 $IC_{50}$ (nM)* | Selectivity** |
|---|---|---|---|
| KV1D261 | 0.15 | 85 | 582 |
| KV1D197 | 0.3 | 145 | 483 |
| KV1D229 | 0.25 | 70 | 280 |
| KV1D267 | 0.47 | 103 | 219 |
| KV1C2 | 13 | 865 | 67 |
| KV1N2 | 0.3 | 2 | 7 |

*$IC_{50}$ values from patch clamp epectrophysiology

**selectivity = $IC_{50(Kv1.1)}/IC_{50(Kv1.3)}$

Based on the patch-clamp studies, the OdK2 chimera peptide Fc fusion proteins had about from 28 to about 87 fold improved Kv1.3 potency and about 3 to 9-fold improved selectivity when compared to the parent KV1C2 (OdK2-Fc fusion), and about ~85-fold improved selectivity when compared to the parent KV1N2 (OsK1-Fc fusion).

Inhibition of T Cell Activation

Select OdK2 chimera peptide Fc fusions were characterized for their ability to inhibit T cell activation measured as inhibition of IL-2 secretion from anti-CD3/C28-induced T cells as described in materials and methods. Inhibition was measured at a single concentration (100 nM) of OdK2 chimera peptide Fc fusions and results are presented as % inhibition of maximum IL-2 production in FIG. 5A. KV1B03 is identical to the parent KV1C2 (OdK2 fusion) and was incidentally recreated during library construction. FIG. 5B shows concentration-dependent inhibition of IL-2 production by activated T-cells by KV1D261. The $IC_{50}$ value for $CD4^+$ T cell inhibition for the KV1D261 fusion protein was 1.66 nM.

Correlation of inhibition of T cell activation and the binding to Kv1.3 using crude supernatants conducted during primary screen of the library was evaluated to assess ability to identify functional Kv1.3 blockers with the binding assay (FIG. 5C). Significant correlation was identified between the two assays (Pearson's correlation r 0.9339, $p<0.0001$).

Antagonistic Effects of Fusion Proteins are Attributable to the Peptide Portion

To determine whether the inhibitory characteristics as well as the selectivity of the OdK2 chimera peptide Fc fusions were retained by the peptide portion, select OdK2 chimera fusions were compared in their characteristics with the corresponding synthetic peptides.

KV1D261 and the corresponding synthetic peptide p261 (SEQ ID NO: 42) were characterized for Kv1.3 potency and selectivity, cross-reactivity to rat Kv1.3 channels, and inhibition of T cell activation. hERG was assayed using routine methods such as those referenced in Dubin et al., J Biomol Screen. 10:168-81, 2005. All cell lines used stably expressed the channel of interest except for rat Kv1.3 and hKCa3.1. Results of the experiments for KV1D261 and the corresponding synthetic peptide p261 are shown in Table 4. The synthetic peptide was ~10-fold more potent than the Fc fusion by both electrophysiology and T cell inhibition, and retained selectivity when compared to the corresponding fusion protein, demonstrating that the engineered peptide region is responsible for conveying the properties of potency and selectivity. The loss of potency when fused with the Fc was expected due to increased entropy with increased molecular weight.

TABLE 4

| | | KV1D261 | | synthetic p261 | |
|---|---|---|---|---|---|
| Channel/ cell line | Assay | $IC_{50}$ (nM) | Fold selec-tivity* | $IC_{50}$ (nM) | Fold selec-tivity* |
| human CD4+ T-cell | IL-2 Inhibition | ~2 | — | 0.02 | — |
| human hKv1.3/ CHO | ephys | 0.15 | — | 0.02 | — |
| rat Kv1.3/ CHO | ephys | <0.3 | — | — | |
| Kv1.3/human CD4+ T-cell | ephys | <1 | — | 0.016 | — |
| Kv1.3/rat CD4+ T-cell | ephys | 0.29 | — | — | |
| hKv1.1/CHO | ephys | 85 | 567x | 3.3 | 165 |
| hKv1.2/CHO | ephys | >300 | >2000 | 68 | 3400 |
| hKv1.5/CHO | ephys | >1000 | >6000 | — | — |
| hERG/CHO | ephys | >1000 | >6000 | — | — |
| KCa3.1/human CD4+ T-cell | ephys | >100 | >600 | — | — |
| KCa3.1/CHO | ephys | — | — | >100 | >5000 | ephys: electrophysiology manual patch-clamp

*Ratio $IC_{50(hKv1.x)}/IC_{50(hKv1.3)}$ in CHO cells

Pharmacokinetic Properties of KV1D261

Sprague Dawley Rats were dosed with KV1D261 (261-Fc fusion) through intravenous bolus administration of a 8.3 mg/ml stock in 1×PBS pH7.0 at 1.2 ml/kg for a final dose of 10 mg/kg. The protein was measured using both ELISA and FACS assay. The half life was assessed to be about 72 hours.

Example 4

Generation of an Amino Acid Scanning Library (KV1D26L1 Library)

To further improve selectivity of Kv1.3 blocking peptides, a scanning library was designed by single substitutions of 9 amino acids (A, R, Q, E, H, L, K, V, D) at each non-cysteine residue of the peptide region of KV1D26 (corresponding peptide p26, SEQ ID NO: 111), a potent but non-selective variant identified from the OdK2/Osk1 chimera library described in Example 2. This amino acid scanning library consisted of 270 variants.

The library was generated and expressed using routine molecular biology methods and as described above. Briefly, the genes encoding for the variant peptides were synthesized using synthetic gene assembly (U.S. Pat. No. 6,521,427 and U.S. Pat. No. 6,670,127) and cloned in frame with the GS $(G_4S)_4$ (SEQ ID NO: 119) linker IgG4 Fc fusion partner in a mammalian expression vector.

The library was expressed as above and screened as crude supernatants for binding to an HEK cell line transfected with the human Kv1.3 EC3 loop chimera channel, and for selectivity by binding to an HEK cell line transfected with the human Kv1.1 EC3 loop chimera channel as described above. Activity was normalized following quantitation of each variant. % Binding for Kv1.3 and Kv1.1 was expressed as a percentage of parent KV1C2 (OdK2-Fc fusion) as described in materials and methods. The library was also screened in the thallium flux assay using the two cell lines as described in materials and methods.

FIG. 4A shows the sequences of select variants. Binding and thallium flux data are summarized in FIG. 4B.

Multiple variants from the amino acid scanning library demonstrated increased binding and selectivity for Kv1.3 over Kv1.1. From the binding assay screen, lysine to glutamine substitutions consistently resulted in increased selectivity for Kv1.3 over Kv1.1. Select variants demonstrating ≥80% binding to Kv1.3 and ≥1.3 fold selectivity over Kv1.1 were purified and characterized further.

Example 5

Characterization of Variants Obtained from the Amino Acid Scanning Library (KV1D26L1 Library)

Competition with Kv Toxin Inhibitors

Select variants were purified and assessed for their potential to compete with the known Kv1.3 inhibitor, agitoxin-2-CysTAMRA, in single point and concentration-response assays as described above. Inhibition was assessed in stable HEK293 cells expressing the human Kv1.3 EC3 loop chimera using 10 nM Agitoxin-2-CysTAMRA and each variant at either 40 nM for single point readings or from 0.015 nM to 4 μM for the concentration-response studies.

% inhibition of agitoxin-2-CysTAMRA binding and $IC_{50}$ values for select variants are shown in Table 5. Select variants inhibited binding of agitoxin-2-CysTAMRA to Kv1.3 at levels similar to KV1D261, and $IC_{50}$ values ranged from 5 nM to 1.3 μM, also with several of the variants in the low nanomolar range of KV1D261.

TABLE 5

| Protein ID | Competitive binding % inhibition Single Concentration (40 nM) | Competitive Binding $IC_{50}$ (nM) | % T cell Inhibition Single Concentration (5 nM) | % T cell Inhibition Single Concentration (250 nM) | T cell Inhibition $IC_{50}$ (nM) |
|---|---|---|---|---|---|
| KV1D664 | 65.1 | 5.7 | 0 | 71.1 | NA |
| KV1D625 | 21.3 | NA | 0 | 70.1 | NA |
| KV1D581 | 61.2 | NA | 13.4 | 78 | NA |
| KV1D603 | 64.2 | NA | 33.7 | 77.5 | 7.5 |
| KV1D342 | 47.6 | NA | 7.5 | 78.2 | NA |
| KV1D576 | 76.2 | NA | 16.3 | 76.2 | NA |
| KV1D291 | 49.6 | NA | 0 | NA | NA |
| KV1D579 | 31.1 | 94.4 | 0 | NA | 26.8 |
| KV1D294 | 46.8 | NA | 0 | NA | NA |
| KV1D662 | 45.4 | NA | 0 | NA | NA |
| KV1D665 | 5.6 | 1394 | 0 | NA | NA |
| KV1D656 | 30.4 | 91.1 | 0 | NA | NA |
| KV1D414 | 32.2 | NA | 0 | NA | NA |
| KV1D356 | 69.7 | NA | 22.2 | NA | NA |
| KV1D437 | 69.8 | 5 | 16.8 | NA | NA |
| KV1D604 | 26.5 | NA | 22.4 | NA | 26.9 |
| KV1D261 | 69.7 | 7.5 | 67.9 | NA | 2.3 |
| No inhibition | 0 | 0 | NA | NA | 0 |
| Fc Control | NA | NA | 0 | NA | 0 |

NA: not done
0: no measurable inhibition

Inhibition of T Cell Activation

The ability of select variants to inhibit T cell activation was assessed as described above using IL-2 secretion as a marker for activation.

Assays were performed at single variant concentration of either 5 nM or 250 nM or using a range from 0.015 nM to 250 nM for a concentration response. % Inhibition from maximal signal for select variants are shown in Table 5.

KV1D579 is a Potent and Selective Kv1.3 Inhibitor

KV1D579 was studied in whole cell patch clamp studies and thallium flux using HEK cells transfected with human Kv1.3, Kv1.1, or Kv1.6 as described above. $IC_{50}$ values for KV1D579 are listed in Table 6 together with the parent KV1D26, an OdK chimera-Fc fusion variant isolated in Example 2. Values in parenthesis are derived from thallium flux assays and values not in parenthesis are derived from the patch clamp study.

TABLE 6

| Protein | hKv1.3 IC$_{50}$ (nM) | hKv1.1 IC$_{50}$ (nM) | Selectivity* | hKv1.6 IC50 (nM) | hKv1.6 Selectivity* |
|---|---|---|---|---|---|
| KV1D26 | ~0.21/(0.32) | ~2/(5.8) | ~10/(18) | 0.6 | 3 |
| KV1D579 | 0.14/(0.14) | >1000/(>380) | >7143/(>2714) | 93.7 | 669 |

Values in parenthesis are derived from thallium flux inhibition assays
*ratio of IC$_{50(Kv1.x)}$/IC$_{50(Kv1.3)}$ Example 6

Generation of C-Terminal Extension Library
(KV1D819L1 Library)

Several peptide-Fc fusion proteins conjugated using the linker GS(G$_4$S)$_4$ (SEQ ID NO: 119) were found to induce undesired inflammatory cytokine release from cultures of resting human peripheral blood mononuclear cells in vitro, while the corresponding synthetic peptides themselves did not. Therefore the undesired cytokine release was attributable to the format of the bivalent peptide-Fc fusion or the Fc itself.

To prevent unwanted cytokine release, peptide 261 (p261) (SEQ ID NO: 42) was synthesized as a human serum albumin fusion protein using linker GS(G$_4$S)$_4$ (SEQ ID NO: 119).

The potency of the resulting fusion protein (KV1D261_23) was further optimized by generating a fusion protein library based on KV1D261_23, where the peptide p261 was extended at its C-terminus by four amino acids. It was hypothesized that extending the C terminus of the peptide region of KV1D261_23 fusion protein would allow for increased binding interactions of the peptide with the extracellular loops of the Kv1.3 channel and thereby increasing potency.

The KV1D261_23 fusion protein was modified by inserting 4 additional amino acids between the C terminus of the peptide and the intervening GS(G$_4$S)$_4$ linker (SEQ ID NO: 119), with the following 12 residues per position in full combination (Q, R, P, H, K, T, N, S, E, G, A, and D) at new positions 39, 40, 41 and 42 in the 261 peptide. The ratio for each residue was 1, except R was 1.5, and S was 0.5, and the resulting theoretical number of possible variants of this library was 12$^4$ (20,736). Genes coding for the peptides with variant C terminal extensions were synthesized as previously described and cloned in frame with the GS(G$_4$S)$_4$ linker (SEQ ID NO: 119) and human serum albumin fusion partner in a mammalian expression vector using routine molecular biology methods.

The library was expressed recombinantly in transiently transfected HEK293 cells. Crude supernatants were screened using direct binding assays and functional thallium flux assays using an HEK cell line transfected with the human Kv1.3 tail chimera channel for Kv1.3 potency, and an HEK cell line transfected with the human Kv1.1 tail chimera channel. Hits from this library were high in basic (R, H, and K), acidic (T, N and G), and non-polar (A and P) residues. FIG. 6 shows the results of the binding and thallium flux assays for select fusion proteins.

Example 7

Characterization of C-Terminal Extension Library
(KV1D819L1 Library)

Select candidates identified from the C-terminal extension library were purified and binding to Kv1.3 confirmed. Concentration-response curves were generated for the thallium flux assays. Table 7 shows the IC$_{50}$ values determined in the thallium flux assay and the amino acid sequence of the C-terminal extension for each variant. KV1D261_26 (p261-HSA fusion using GS(G$_4$S)$_8$ linker (SEQ ID NO: 120)) was used as a control in the assay. Most p261 C-terminal extension peptide fusions demonstrated similar or increased potency in the thallium flux when compared to the control with a non-extended peptide moieties. KV1D261_26 fusion having longer linker than KV1D261_23 consistently tested ~5 fold more potent than KV1D261_23 (p261-HSA fusion protein using Gs(G$_4$S)$_4$ linker (SEQ ID NO: 119).

TABLE 7

| Protein ID | Half-life extending moiety | Linker | Peptide portion | C-terminal extension Amino acid sequence | C-terminal extension SEQ ID NO: | % Binidng (of KV1D261_26) | Thallium Flux IC$_{50}$ (nM) |
|---|---|---|---|---|---|---|---|
| KV1D826 | HSA* | GS(G$_4$S)$_4$** | p261 extended | TRRP | 156 | 109.8% | 3.4 |
| KV1D829 | HSA | GS(G$_4$S)$_4$ | p261 extended | AHRH | 209 | 96.6% | 3.3 |
| KV1D830 | HSA | GS(G$_4$S)$_4$ | p261 extended | AQRP | 210 | 76.2% | 7.6 |
| KV1D831 | HSA | GS(G$_4$S)$_4$ | p261 extended | ARRN | 234 | 117.2% | 2.7 |
| KV1D832 | HSA | GS(G$_4$S)$_4$ | p261 extended | ASDN | 236 | 15.1% | 37.2 |
| KV1D834 | HSA | GS(G$_4$S)$_4$ | p261 extended | ATRP | 206 | 95.2% | 5.9 |
| KV1D841 | HSA | GS(G$_4$S)$_4$ | p261 extended | NHRT | 222 | 88.4% | 5.9 |
| KV1D848 | HSA | GS(G$_4$S)$_4$ | p261 extended | PNRT | 223 | 66.2% | 6.7 |
| KV1D853 | HSA | GS(G$_4$S)$_4$ | p261 extended | PTTR | 241 | 55.0% | 9.1 |
| KV1D856 | HSA | GS(G$_4$S)$_4$ | p261 extended | RHNT | 226 | 34.5% | 6.7 |
| KV1D858 | HSA | GS(G$_4$S)$_4$ | p261 extended | RKKP | 173 | 73.7% | 6.0 |
| KV1D860 | HSA | GS(G$_4$S)$_4$ | p261 extended | RQTR | 253 | 52.6% | 6.7 |
| KV1D863 | HSA | GS(G$_4$S)$_4$ | p261 extended | RRRP | 208 | 100.0% | 2.8 |
| KV1D864 | HSA | GS(G$_4$S)$_4$ | p261 extended | RTRQ | 248 | 57.9% | 5.3 |
| KV1D865 | HSA | GS(G$_4$S)$_4$ | p261 extended | SHRP | 139 | 127.6% | 2.8 |

TABLE 7-continued

| Protein ID | Half-life extending moiety | Linker | Peptide portion | C-terminal extension Amino acid sequence | SEQ ID NO: | % Binidng (of KV1D261_26) | Thallium Flux IC$_{50}$ (nM) |
|---|---|---|---|---|---|---|---|
| KV1D869 | HSA | GS(G$_4$S)$_4$ | p261 extended | TTRT | 233 | 77.4% | 5.9 |
| KV1D261_26 | HSA | GS(G$_4$S)$_4$ | p261 extended | none | | 99.8% | 1.0 |

*human serum albumin
**SEQ ID NO: 119

Example 8

Peptide HSA Fusion Protein Engineering

Peptide 261 was engineered as fusion protein with human serum albumin (HSA) using various linkers and the resulting fusion proteins tested for their Kv1.3 potency and selectivity, and inhibition of T cell activation. Results of T cell inhibition measured as inhibition of IL-2 secretion as well as thallium flux inhibition with peptide 261 conjugated to HSA via various linkers is shown in Table 8.

TABLE 8

| Protein | Linker name | Linker SEQ ID NO: | Tcell Inhibition IC$_{50}$ (nM) | Thallium Flux KV1.3 IC$_{50}$ (nM) |
|---|---|---|---|---|
| KV1D261_23 | GS(G$_4$S)$_4$ | 119 | 80.1 | 20.0 |
| KV1D261_32 | (EAAAK)$_4$ | 117 | 129.1 | 10.2 |
| KV1D261_33 | AS(AP)$_{10}$GS | 115 | 10.8 | 1.1 |
| KV1D261_34 | AS(AP)$_{20}$GS | 116 | 4.5 | 0.4 |
| KV1D261_35 | 1DC1(13AA)$_2$ | 113 | 20.3 | 3.6 |
| KV1D261_36 | 1DC1(13AA)$_3$ | 114 | 10.4 | 1.8 |
| KV1D261_37 | 1FU1 | 112 | 151.1 | 9.2 |
| KV1D261_38 | (EAAAK)$_8$ | 118 | 10.3 | 0.7 |

The linker engineering indicated that inserting the more structured alanine proline (AP) repeat linker into the fusion protein instead of the more flexible glycine serine (GS) linker significantly improved potency, and that increasing the linker length further enhanced potency. The IDC1 (13AA)$_2$ (SEQ ID NO: 113) and IDC1(13AA)$_3$ (SEQ ID NO: 114) and (EAAAK)$_8$ (SEQ ID NO: 118) linkers also improved potency, but appeared less stable during protein production with fusion protein fragments present following purification. The fusion protein KV1D261_34 with peptide 261 conjugated to HSA via the AS(AP)$_{20}$GS linker (SEQ ID NO: 116) had an IC$_{50}$ for Kv1.3 of about 4 nM in T cell inhibition assay and IC$_{50}$ of about 0.4 nM in the thallium flux assay.

Characterization of p261 and p579 HSA Fusions

Fusion protein KV1D261_34 and the corresponding synthetic peptide p261 as well as peptide p579 conjugated to human HSA via the AS(AP)$_{20}$GS linker (SEQ ID NO: 116) to generate a fusion protein KV1G49.KV1W720 were further tested in various functional assays and for their selectivity against human Kv channels as shown in Table 9.

TABLE 9

| Channel/cell line | Assay | KV1D261_34 IC$_{50}$ (nM) | KV1D261_34 Fold selectivity# | p261 synthetic peptide IC$_{50}$ (nM) | p261 synthetic peptide Fold selectivity# | KV1G49.KV1W720 IC$_{50}$ (nM) | KV1G49.KV1W720 Fold selectivity |
|---|---|---|---|---|---|---|---|
| hKv1.3/HEK | competitive binding | 54 | — | 1.53 | — | 342.0 | — |
| hKv1.3/CHO | thallium flux | 0.3 | — | 0.03-0.04 | — | 9.0 | — |
| hKv1.3/CHO | ephys | 1.2 | — | 0.02* | — | 3.0 | — |
| primary human CD4$^+$ T cell | ephys | NA | — | 0.016 | — | — | |
| primary human CD4$^+$ T cell | T cell inhibition | 2.1 | — | 0.02 | — | 15.8 | — |
| hKv1.1/CHO | thallium flux | 79 | 247 | 2.0-8.0 | 5-266 | >251** | |
| hKv1.1/CHO | ephys | >1000 | >1000 | 3.3 | 165 | | |
| hKv1.2/CHO | ephys | >100 | >100 | 68 | 3400 | | |
| hKv1.4/CHO | ephys | >100 | >100 | >300 | >15000 | | |
| hKv1.5/CHO | ephys | >100 | >100 | — | — | | |
| hKv1.6/CHO | ephys | 10 | 8 | 0.32 | 12 | | |
| hKv1.7/CHO | ephys | >100 | >100 | >100 | >5000 | | |
| hKCa3.1/CHO | ephys | — | — | >100 | >5000 | | | ephys: patch clamp electrohpysiology
*IC$_{50}$ 20 pM in 1% BSA and 13 pM in 5% FCS
**incomplete concentration response due to low potency. IC$_{50}$ is reported as greater than the highest concentration tested
ratio of IC$_{50(KV1.1)}$/IC$_{50(Kv1.3)}$ in CHO cells KV1D261_34 was also tested for its ability to inhibit thapsigargin-induced IL-17A production from human and porcine (Yucatan minipig) whole blood. The $IC_{50}$ value for the inhibition in both humans and minipig was 0.5 nM. KV1D261_34 also inhibited minipig $CD4^+$ T cell activation (IL-2 secretion) with an $IC_{50}$ value of 1.6 nM.

Example 9

Generation and Characterization of Additional C-Terminal Extension Peptide Fusions Peptides p261 (SEQ ID NO: 42) and p579 (SEQ ID NO: 3) were extended using several C-terminal extensions and conjugated to HSA via the $AS(AP)_{20}GS$ (SEQ ID NO: 116) or the $GS(AP)_{20}AS$ linker (SEQ ID NO: 428). Select fusion proteins were expressed, purified and characterized in assays including competitive binding, thallium flux, inhibition of in vitro human $CD4^+$ T cell activation, and electrophysiology assays.

FIG. 7A shows characteristics of fusion proteins having various C-terminal extensions on peptide p261. For assessing T cell inhibition, select variants were tested either for % inhibition of anti CD3/CD28 stimulated human $CD4^+$ T cell IL-2 production at a single concentration of 1 nM (T cell % Inhibition @1 nM), or $IC_{50}$ values were derived from concentration-response curves using the same assay (T cell Inhibition $IC_{50}$ nM). Fold selectivity was measured as a ratio of $IC_{50}$(Kv1.1)/$IC_{50}$(Kv1.3) using the values from the thallium flux assay.

The competitive binding Ki values for the C-terminally extended peptide fusion proteins ranged from about 0.15 nM to about 18.0 nM, compared to the Ki of about 1 nM for the parent KV1D261_34 non-extended peptide fusion. Several of the variants had improved potency and selectivity compared to the parent KV1D261_34, with the thallium flux $IC_{50}$ values ranging from about 10 pM to about 1 nM and fold selectivity over Kv1.1 from about 30 to about 800.

Manual patch-clamp studies were conducted for select peptide fusion proteins in Kv1.3 transfected CHO cell lines as described above. The $IC_{50}$ values for KV1G15.KV1W686 (C-terminal extension of peptide p261 using AHRH (SEQ ID NO: 209) fused to HSA via $AS(AP)_{20}GS$ linker (SEQ ID NO: 116) was 199 pM. Some of the C-terminal insertions resulted in a ~5-10-fold increase in potency over the parent KV1D261_34.

Fusion proteins of p579 with and without select C-terminal extension conjugated to HSA with an intervening $GS(AP)_{20}AS$ (SEQ ID NO: 116) were characterized in competitive binding (competition with 10 nM agitoxin-cys-TAMRA binding to HEK cells) and T-cell inhibition (IL-2 secretion) and the results are shown in FIG. 7B. Some of the C-terminal insertions resulted in a ~3-5-fold increase in potency over the parent, KV1G49.KV1W720.

Several HSA fusion proteins conjugated to peptide variants using the $AS(AP)_{20}GS$ linker (SEQ ID NO: 116) were tested for their ability to induce the secretion of cytokines and chemokines (IFNγ, IL-1β, TNF-α, IL-2, IL-4, IL-5, IL12p70 and IL-13) from PBMCs. No induction was seen for these HSA fusions.

Example 10

KV1D261_34 Pharmacokinetics and Pharmacodynamics in Minipigs

Figure 9:
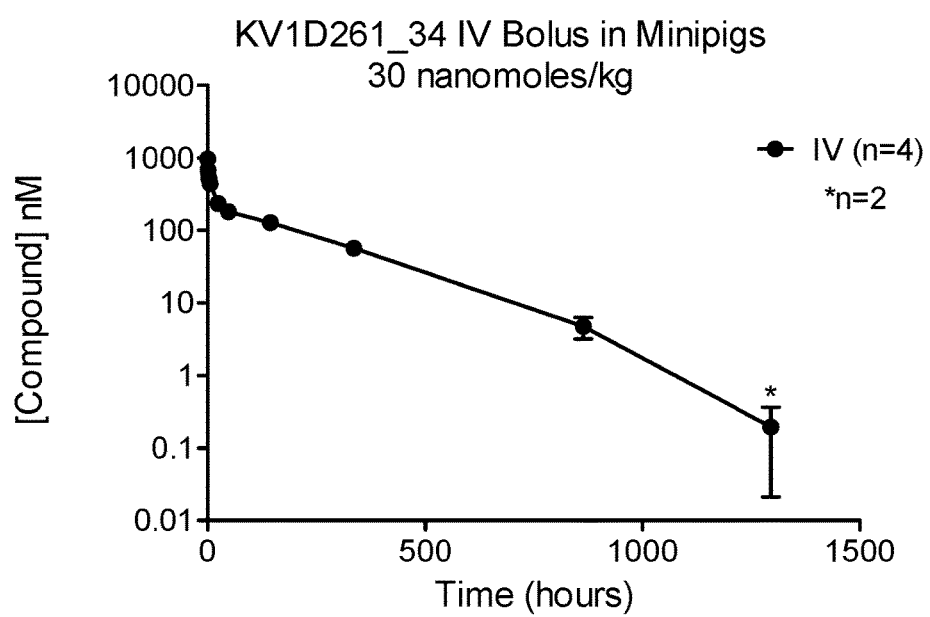
FIG. 9. Pharmacokinetics of KV1D261_34 in minipigs.

KV1D261_34, (261 peptide HSA fusion protein with intervening $AS(AP)_{20}GS$ linker (SEQ ID NO: 116)) was administered to mini-pigs as a single intravenous injection (30 nmoles/Kg). Heparinized plasma samples were collected at various time points post administration and plasma levels were determined using anti-261 capture/anti-penta His-HRP ELISA. FIG. 9 shows results as the mean±SD of 4 animals through day 36, and of 2 animals at the final 54 day time point. Half-life (T1/2) of the fusion protein was 5-7 days, with clearance (CL) 0.008-0.01 ml/min/Kg and volume of distribution (Vss)=90-120 ml/Kg.

Target engagement was assessed by measuring IL-17A secretion from lymphocytes in whole blood ex-vivo. Whole blood samples were collected from each study animal at times −48, −24, −1 hour pre administration, and at time points between 0.017-1296 hours (54 days) post administration of KV1D261_34 (30 nmoles/Kg). Whole blood samples were treated with thapsigargin in the absence or presence of 1 µM exogenous 261 peptide, with each condition in triplicate per sample. IL-17 cytokine levels were measured in an anti-porcine IL-17A ELISA, and % Inhibition by exogenous peptide 261 calculated as follows:

100−(Average IL-17 pg/ml concentrations in the +thapsigargin+1 µM exogenous 261 reactions/Average IL-17 pg/ml concentrations in the +thapsigargin reactions)×100.

Figure 10:
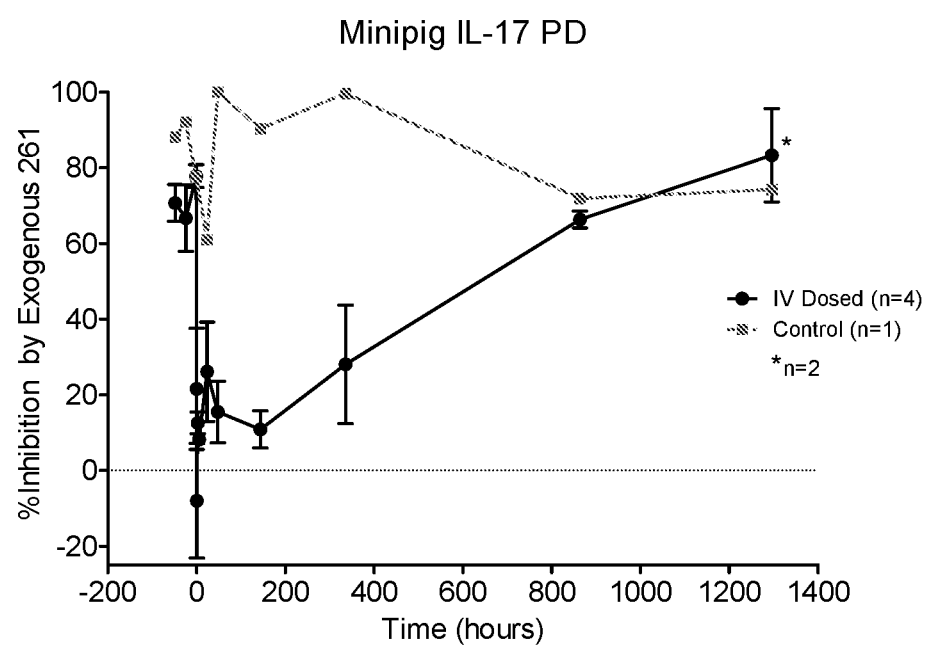
FIG. 10. Ex-vivo inhibition of IL-17A secretion from lymphocytes following in vivo administration of KV1D261_34 in minipigs.

The results of experiment, expressed as the % inhibition of thapsigargin-induced IL-17 secretion by exogenous 261 peptide (mean±SD of 4 animals except at 54 days, where 2 animals were analyzed) are shown in FIG. 10. The average % Inhibition of thapsigargin-induced IL-17 secretion by exogenous 261 for all of the predosed samples and the non-dosed control animal (all time points) was 75.3±14.1%. The mean % Inhibition of thapsigargin-induced IL-17 secretion by exogenous 261 in whole blood ex-vivo was ≤25% for approximately 14 days following IV administration of KV1D261-34, indicating a high level of target engagement by circulating KV1D261_34. Plasma concentrations at these time points were >10 nM. At later time points the % Inhibition of thapsigargin-induced IL-17 secretion by exogenous 261 increased to >65% on day 36 and reached baseline levels of ≥80% by day 54, indicating gradual reduction of target engagement as plasma levels declined. The findings of this study show that KV1D261_34 is stable in plasma in vivo and has a long plasma half-life in minipigs. Circulating KV1D261_34 is bioavailable and inhibits thapsigargin-induced IL-17 secretion on lymphocytes following intravenous dosing. Inhibition of thapsigargin-induced IL-17 secretion appeared to be well correlated with plasma concentration and effective plasma concentrations were consistent with the proposed mechanism of action (Kv1.3 block) of KV1D261_34.

Example 11

Minipig Keyhole Limpet Hemocyanin (KLH)-Induced Delayed Type Hypersensitivity (DTH) Model Minipig Delayed Type Hypersensitivity (DTH) model was used as an in vivo model to assess ability of KV1D261_34 to inhibit T cell function. Minipigs were dosed IV with either vehicle (PBS, n=6) or KV1D261_34 (30 nmoles/kg, n=6). As a positive control, Cyclosporine A was administered subcutaneously twice daily with 1 ml/kg at a concentration of 10 mg/ml from day −1 until necropsy (n=6). Dosing commenced one day prior (Day −1) to immunization with KLH antigen. Minipigs were immunized with KLH on day 0 by 1 ml subcutaneous injections of either 5 mg/ml KLH in Incomplete Freund Adjuvant (IFA), or PBS in IFA for the control group. Injections were made at ~5 locations on the caudal aspect of the hind legs. Animals were then challenged on day 7 with intradermal injections of 0.1 ml/spot with KLH at 10, 5, 2.5, 1.25 mg/ml, or PBS, with one spot per challenge dose on the left flank, and a duplicate challenge spot on the right flank. The level of induration was measured on days 9 and 10, one and two days post challenge, and on day 10 tissue and blood samples were collected for additional measurements of draining lymph node cellularity, anti antigen antibody titers, and challenge site histology.

Figure 11:
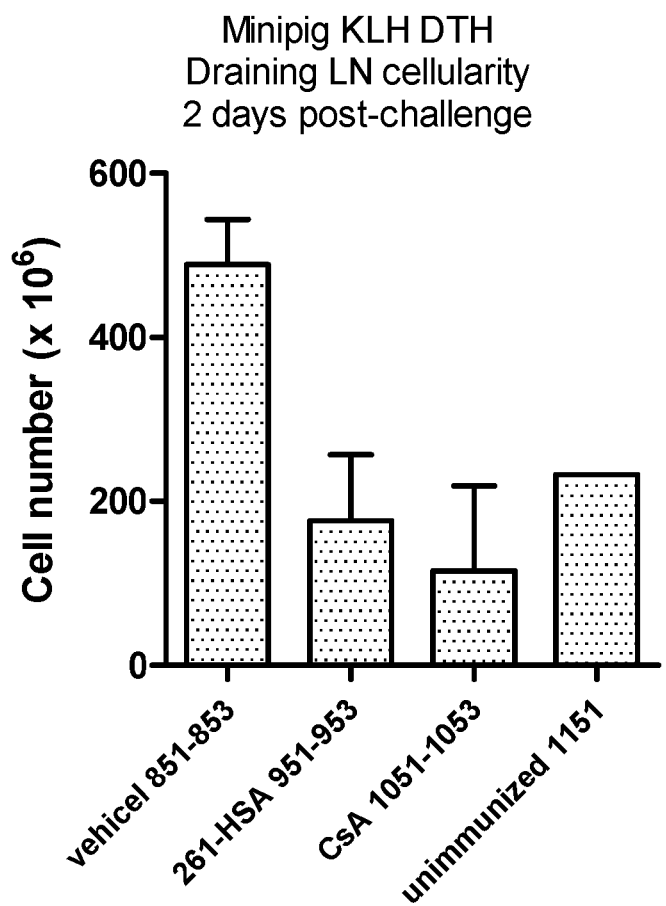
FIG. 11. Cell numbers from draining lymph nodes at day 10 following antigen challenge in the delayed type hypersensitivity (DTH) minipig model.

Draining lymph nodes were collected on day 10, two days after the challenge, for the determination of lymph node cellularity. The results are shown in FIG. 11. KV1D261_34 treated animals had significantly reduced cellularity when compared to the vehicle treated challenged animals. Cellularity was reduced to a level that was comparable to that observed in the unimmunized control animals.

No significant reduction in anti-KLH antibody titers or induration was detected in KV1D261_34 administered animals at days 9 and 10 (1 and 2 days post-challenge).

The invention claimed is:

1. An isolated fusion protein comprising a peptide antagonist of Kv1.3 conjugated to a half-life extending moiety, wherein the peptide antagonist of Kv1.3 comprises the amino acid sequence GVPX$aa_1$X$aa_2$VKCX$aa_3$ISRQCX$aa_4$X$aa_5$PCKDAG-MRFGKCMNGKCHCTPK (SEQ ID NO: 427); wherein
   a) $Xaa_1$ is I or T;
   b) $Xaa_2$ is N or D;
   c) $Xaa_3$ is K or R;
   d) $Xaa_4$ is I or E; and
   e) $Xaa_5$ is E or K, and has an $IC_{50}$ value of about $1 \times 10^{-8}$ M or less towards Kv1.3 in a whole cell patch clamp assay on Chinese hamster ovary (CHO) cells transfected with Kv1.3, and is at least 100-fold more selective towards Kv1.3 when compared to a fusion protein comprising a wild-type Odk2 peptide of SEQ ID NO: 1 conjugated to the half-life extending moiety, when selectivity is calculated as a ratio of Kv1.1 $IC_{50}$ value to Kv1.3 $IC_{50}$ value in the whole cell patch clamp assay on CHO cells transfected with Kv1.3 or Kv1.1.

2. The fusion protein of claim 1, wherein the peptide antagonist of Kv1.3 comprises the amino acid sequence of SEQ ID NOs: 3, 22, 34 or 42.

3. The fusion protein of claim 2, wherein the half-life extending moiety is human serum albumin (HSA), albumin binding domain (ADB), or polyethylene glycol (PEG).

4. The fusion protein of claim 3, wherein the half-life extending moiety is human serum albumin.

5. The fusion protein of claim 3, wherein the half-life extending moiety is conjugated to the peptide antagonist of Kv1.3 via a linker.

6. The fusion protein of claim 5, wherein the linker comprises the amino sequence of SEQ ID NOs: 112-122 or 428.

7. The fusion protein of claim 6, wherein
   a) the peptide antagonist of Kv1.3 comprises the amino acid sequence of SEQ ID NOs: 3, 22, 34 or 42;
   b) the linker comprises the amino acid sequence of SEQ ID NO: 116 or SEQ ID NO:119; and
   c) the half-life extending moiety is human serum albumin.

8. The fusion protein of claim 6, wherein
   a) the peptide antagonist of Kv1.3 comprises the amino acid sequence of SEQ ID NO: 42;
   b) the linker comprises the amino acid sequence of SEQ ID NO: 116; and
   c) the half-life extending moiety is human serum albumin.

9. The fusion protein of claim 6, wherein
   a) The peptide antagonist of Kv1.3 comprises the amino acid sequence of SEQ ID NO: 42;
   b) the C-terminal extension comprises the amino acid sequence of SEQ ID NO: 209;
   c) the linker comprises the amino acid sequence of SEQ ID NO: 116; and
   d) the half-life extending moiety is human serum albumin.

10. A pharmaceutical composition comprising the fusion protein of claim 2 and a pharmaceutically acceptable carrier.

11. An isolated peptide antagonist of Kv1.3 comprising the amino acid sequence GVPX$aa_1$X$aa_2$VKCX$aa_3$ISRQCX$aa_4$X$aa_5$PCKDAG-MRFGKCMNGKCHCTPK (SEQ ID NO: 427);
   wherein
   a) $Xaa_1$ is I or T;
   b) $Xaa_2$ is N or D;
   c) $Xaa_3$ is K or R;
   d) $Xaa_4$ is I or E; and
   e) $Xaa_5$ is E or K, wherein the peptide antagonist of Kv1.3 has an $IC_{50}$ value of about $1 \times 10^{-8}$ M or less towards Kv1.3 in a whole cell patch clamp assay on Chinese hamster ovary (CHO) cells transfected with Kv1.3, and is at least 100-fold more selective towards Kv1.3 when compared to a fusion protein comprising a wild-type Odk2 peptide of SEQ ID NO: 1 conjugated to the half-life extending moiety, when selectivity is calculated as a ratio of Kv1.1 $IC_{50}$ value to Kv1.3 $IC_{50}$ value in the whole cell patch clamp assay on CHO cells transfected with Kv1.3 or Kv1.1.

12. The peptide antagonist of Kv1.3 of claim 11, comprising the amino acid sequence of SEQ ID NOs: 3 or 42.

* * * * *

SEQUENCE LISTING

```
<160> NUMBER OF SEQ ID NOS: 433

<210> SEQ ID NO 1
<211> LENGTH: 38
<212> TYPE: PRT
<213> ORGANISM: Odontobuthus doriae

<400> SEQUENCE: 1

Gly Val Pro Thr Asp Val Lys Cys Arg Gly Ser Pro Gln Cys Ile Gln
1               5                  10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 2
<211> LENGTH: 38
<212> TYPE: PRT
<213> ORGANISM: Orthochirus scrobiculosus

<400> SEQUENCE: 2

Gly Val Ile Ile Asn Val Lys Cys Lys Ile Ser Arg Gln Cys Leu Glu
1               5                  10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 3
<211> LENGTH: 38
<212> TYPE: PRT
<213> ORGANISM: Artificial sequence
<220> FEATURE:
<223> OTHER INFORMATION: Odk2 variant

<400> SEQUENCE: 3

Gly Val Pro Thr Asp Val Lys Cys Arg Ile Ser Arg Gln Cys Glu Lys
1               5                  10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 4
<211> LENGTH: 38
<212> TYPE: PRT
<213> ORGANISM: Artificial sequence
<220> FEATURE:
<223> OTHER INFORMATION: Odk2 variant
```

```
<400> SEQUENCE: 4

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys Asp Cys Thr Pro Lys
        35

<210> SEQ ID NO 5
<211> LENGTH: 38
<212> TYPE: PRT
<213> ORGANISM: Artificial sequence
<220> FEATURE:
<223> OTHER INFORMATION: Odk2  variant

<400> SEQUENCE: 5

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Val Gly Lys
            20                  25                  30

Cys His Cys Thr Pro Lys
        35

<210> SEQ ID NO 6
<211> LENGTH: 38
<212> TYPE: PRT
<213> ORGANISM: Artificial sequence
<220> FEATURE:
<223> OTHER INFORMATION: Odk2  variant

<400> SEQUENCE: 6

Gly Val Pro Thr Asp Val Lys Cys Arg Ile Ser Ala Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 7
<211> LENGTH: 38
<212> TYPE: PRT
<213> ORGANISM: Artificial sequence
<220> FEATURE:
<223> OTHER INFORMATION: Odk2  variant

<400> SEQUENCE: 7

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Glu
        35

<210> SEQ ID NO 8
<211> LENGTH: 38
<212> TYPE: PRT
<213> ORGANISM: Artificial sequence
<220> FEATURE:
<223> OTHER INFORMATION: Odk2  variant

<400> SEQUENCE: 8

Gly Val Pro Thr Asp Val Lys Cys Arg Ile Ser Arg Gln Cys Leu Lys
```

```
                1               5                  10                 15
Pro Cys Lys Asp Ala Gly Met Arg Phe Gly Lys Cys Leu Asn Gly Lys
                20                 25                 30

Cys His Cys Thr Pro Lys
        35

<210> SEQ ID NO 9
<211> LENGTH: 38
<212> TYPE: PRT
<213> ORGANISM: Artificial sequence
<220> FEATURE:
<223> OTHER INFORMATION: Odk2 variant

<400> SEQUENCE: 9

Gly Val Pro Thr Asp Val Lys Cys Arg Ile Ala Arg Gln Cys Leu Lys
1               5                  10                 15

Pro Cys Lys Asp Ala Gly Met Arg Phe Gly Lys Cys Met Asn Gly Lys
                20                 25                 30

Cys His Cys Thr Pro Lys
        35

<210> SEQ ID NO 10
<211> LENGTH: 38
<212> TYPE: PRT
<213> ORGANISM: Artificial sequence
<220> FEATURE:
<223> OTHER INFORMATION: Odk2 variant

<400> SEQUENCE: 10

Gly Val Pro Thr Asp Val Lys Cys Arg Ile Ser Arg Gln Cys Leu Lys
1               5                  10                 15

Pro Cys Lys Asp Ala Gly Met His Phe Gly Lys Cys Met Asn Gly Lys
                20                 25                 30

Cys His Cys Thr Pro Lys
        35

<210> SEQ ID NO 11
<211> LENGTH: 38
<212> TYPE: PRT
<213> ORGANISM: Artificial sequence
<220> FEATURE:
<223> OTHER INFORMATION: Odk2 variant

<400> SEQUENCE: 11

Gly Val Pro Thr Asp Val Lys Cys Arg Ile Ser Arg Gln Cys Asp Lys
1               5                  10                 15

Pro Cys Lys Asp Ala Gly Met Arg Phe Gly Lys Cys Met Asn Gly Lys
                20                 25                 30

Cys His Cys Thr Pro Lys
        35

<210> SEQ ID NO 12
<211> LENGTH: 38
<212> TYPE: PRT
<213> ORGANISM: Artificial sequence
<220> FEATURE:
<223> OTHER INFORMATION: Odk2 variant

<400> SEQUENCE: 12

Gly Val Pro Thr Asp Val Lys Cys Arg Ile Ser Arg Gln Cys Leu Lys
1               5                  10                 15

Pro Cys Glu Asp Ala Gly Met Arg Phe Gly Lys Cys Met Asn Gly Lys
```

```
                    20                  25                  30

Cys His Cys Thr Pro Lys
        35

<210> SEQ ID NO 13
<211> LENGTH: 38
<212> TYPE: PRT
<213> ORGANISM: Artificial sequence
<220> FEATURE:
<223> OTHER INFORMATION: Odk2 variant

<400> SEQUENCE: 13

Gly Val Pro Thr Asp Val Lys Cys Glu Ile Ser Arg Gln Cys Leu Lys
1               5                   10                  15

Pro Cys Lys Asp Ala Gly Met Arg Phe Gly Lys Cys Met Asn Gly Lys
                20                  25                  30

Cys His Cys Thr Pro Lys
        35

<210> SEQ ID NO 14
<211> LENGTH: 38
<212> TYPE: PRT
<213> ORGANISM: Artificial sequence
<220> FEATURE:
<223> OTHER INFORMATION: Odk2 variant

<400> SEQUENCE: 14

Leu Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
                20                  25                  30

Cys His Cys Thr Pro Lys
        35

<210> SEQ ID NO 15
<211> LENGTH: 38
<212> TYPE: PRT
<213> ORGANISM: Artificial sequence
<220> FEATURE:
<223> OTHER INFORMATION: Odk2 variant

<400> SEQUENCE: 15

Gly Val Pro Thr Asp Val Lys Cys Arg Ile Ser Arg Asp Cys Leu Lys
1               5                   10                  15

Pro Cys Lys Asp Ala Gly Met Arg Phe Gly Lys Cys Met Asn Gly Lys
                20                  25                  30

Cys His Cys Thr Pro Lys
        35

<210> SEQ ID NO 16
<211> LENGTH: 38
<212> TYPE: PRT
<213> ORGANISM: Artificial sequence
<220> FEATURE:
<223> OTHER INFORMATION: Odk2 variant

<400> SEQUENCE: 16

Gly Val Pro Thr Asp Val Lys Cys Arg Ile Ser Arg Gln Cys Leu Lys
1               5                   10                  15

Pro Cys Asp Asp Ala Gly Met Arg Phe Gly Lys Cys Met Asn Gly Lys
                20                  25                  30

Cys His Cys Thr Pro Lys
```

<210> SEQ ID NO 17
<211> LENGTH: 38
<212> TYPE: PRT
<213> ORGANISM: Artificial sequence
<220> FEATURE:
<223> OTHER INFORMATION: Odk2 variant

<400> SEQUENCE: 17

Gly Val Pro Thr Asp Val Lys Cys Arg Ile Ser Arg Glu Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 18
<211> LENGTH: 38
<212> TYPE: PRT
<213> ORGANISM: Artificial sequence
<220> FEATURE:
<223> OTHER INFORMATION: Odk2 variant

<400> SEQUENCE: 18

Gly Val Pro Thr Asp Val Lys Cys Arg Ile Ser Arg Gln Cys Leu Lys
1               5                   10                  15

Pro Cys Lys Asp Ala Gly Met Arg Phe Gly Arg Cys Met Asn Gly Lys
            20                  25                  30

Cys His Cys Thr Pro Lys
        35

<210> SEQ ID NO 19
<211> LENGTH: 38
<212> TYPE: PRT
<213> ORGANISM: Artificial sequence
<220> FEATURE:
<223> OTHER INFORMATION: Odk2 variant

<400> SEQUENCE: 19

Gly Val Pro Thr Asp Val Lys Cys Arg Ile Ser Arg Gln Cys Leu Lys
1               5                   10                  15

Pro Cys Lys Asp Ala Gly Met Lys Phe Gly Lys Cys Met Asn Gly Lys
            20                  25                  30

Cys His Cys Thr Pro Lys
        35

<210> SEQ ID NO 20
<211> LENGTH: 38
<212> TYPE: PRT
<213> ORGANISM: Artificial sequence
<220> FEATURE:
<223> OTHER INFORMATION: Odk2 variant

<400> SEQUENCE: 20

Gly Val Pro Thr Asp Val Lys Cys Arg Ile Ser Leu Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 21
<211> LENGTH: 38
<212> TYPE: PRT
<213> ORGANISM: Artificial sequence
<220> FEATURE:
<223> OTHER INFORMATION: Odk2 variant

<400> SEQUENCE: 21

Gly Val Pro Thr Asp Val Lys Cys Ala Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 22
<211> LENGTH: 38
<212> TYPE: PRT
<213> ORGANISM: Artificial sequence
<220> FEATURE:
<223> OTHER INFORMATION: Odk2 variant

<400> SEQUENCE: 22

Gly Val Pro Ile Asp Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 23
<211> LENGTH: 38
<212> TYPE: PRT
<213> ORGANISM: Artificial sequence
<220> FEATURE:
<223> OTHER INFORMATION: Odk2 variant

<400> SEQUENCE: 23

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Glu
            20                  25                  30

Cys His Cys Thr Pro Lys
        35

<210> SEQ ID NO 24
<211> LENGTH: 38
<212> TYPE: PRT
<213> ORGANISM: Artificial sequence
<220> FEATURE:
<223> OTHER INFORMATION: Odk2 variant

<400> SEQUENCE: 24

Gly Val Pro Thr Asp Val Lys Cys Lys Ile Ser Pro Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 25
<211> LENGTH: 38
<212> TYPE: PRT

```
<213> ORGANISM: Artificial sequence
<220> FEATURE:
<223> OTHER INFORMATION: Odk2 variant

<400> SEQUENCE: 25

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys Val Cys Thr Pro Lys
        35

<210> SEQ ID NO 26
<211> LENGTH: 38
<212> TYPE: PRT
<213> ORGANISM: Artificial sequence
<220> FEATURE:
<223> OTHER INFORMATION: Odk2 variant

<400> SEQUENCE: 26

Gly Val Pro Ile Asp Val Lys Cys Arg Ile Ser Pro Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 27
<211> LENGTH: 38
<212> TYPE: PRT
<213> ORGANISM: Artificial sequence
<220> FEATURE:
<223> OTHER INFORMATION: Odk2 variant

<400> SEQUENCE: 27

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Ala Asn Gly Lys
            20                  25                  30

Cys His Cys Thr Pro Lys
        35

<210> SEQ ID NO 28
<211> LENGTH: 38
<212> TYPE: PRT
<213> ORGANISM: Artificial sequence
<220> FEATURE:
<223> OTHER INFORMATION: Odk2 variant

<400> SEQUENCE: 28

His Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 29
<211> LENGTH: 38
<212> TYPE: PRT
<213> ORGANISM: Artificial sequence
<220> FEATURE:
<223> OTHER INFORMATION: Odk2 variant
```

<400> SEQUENCE: 29

Gly Val Pro Thr Asp Val Lys Cys Arg Ile Ser Arg Gln Cys Gln Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 30
<211> LENGTH: 38
<212> TYPE: PRT
<213> ORGANISM: Artificial sequence
<220> FEATURE:
<223> OTHER INFORMATION: Odk2 variant

<400> SEQUENCE: 30

Gly Val Pro Thr Asp Val Lys Cys Arg Ile Ser Glu Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 31
<211> LENGTH: 38
<212> TYPE: PRT
<213> ORGANISM: Artificial sequence
<220> FEATURE:
<223> OTHER INFORMATION: Odk2 variant

<400> SEQUENCE: 31

Gly Val Pro Thr Asp Val Lys Cys Arg Ile Ser Arg Gln Cys Leu Lys
1               5                   10                  15

Pro Cys Val Asp Ala Gly Met Arg Phe Gly Lys Cys Met Asn Gly Lys
            20                  25                  30

Cys His Cys Thr Pro Lys
        35

<210> SEQ ID NO 32
<211> LENGTH: 38
<212> TYPE: PRT
<213> ORGANISM: Artificial sequence
<220> FEATURE:
<223> OTHER INFORMATION: Odk2 variant

<400> SEQUENCE: 32

Gly Val Pro Thr Asp Val Lys Cys Arg Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 33
<211> LENGTH: 38
<212> TYPE: PRT
<213> ORGANISM: Artificial sequence
<220> FEATURE:
<223> OTHER INFORMATION: Odk2 variant

<400> SEQUENCE: 33

```
Gly Val Pro Thr Asp Val Glu Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35
```

<210> SEQ ID NO 34
<211> LENGTH: 38
<212> TYPE: PRT
<213> ORGANISM: Artificial sequence
<220> FEATURE:
<223> OTHER INFORMATION: Odk2 variant

<400> SEQUENCE: 34

```
Gly Val Pro Thr Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35
```

<210> SEQ ID NO 35
<211> LENGTH: 38
<212> TYPE: PRT
<213> ORGANISM: Artificial sequence
<220> FEATURE:
<223> OTHER INFORMATION: Odk2 variant

<400> SEQUENCE: 35

```
Gly Val Pro Ile Asp Val Lys Cys Lys Ile Ser Pro Gln Cys Ile Glu
1               5                   10                  15

Pro Cys Lys Lys Ala Gly Met Arg Phe Gly Lys Cys Met Asn Gly Lys
            20                  25                  30

Cys His Cys Thr Pro Lys
        35
```

<210> SEQ ID NO 36
<211> LENGTH: 38
<212> TYPE: PRT
<213> ORGANISM: Artificial sequence
<220> FEATURE:
<223> OTHER INFORMATION: Odk2 variant

<400> SEQUENCE: 36

```
Gly Val Ile Thr Asp Val Lys Cys Lys Ile Ser Pro Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35
```

<210> SEQ ID NO 37
<211> LENGTH: 38
<212> TYPE: PRT
<213> ORGANISM: Artificial sequence
<220> FEATURE:
<223> OTHER INFORMATION: Odk2 variant

<400> SEQUENCE: 37

```
Gly Val Pro Thr Asp Val Lys Cys Arg Ile Ser Arg Gln Cys Leu Lys
1               5                   10                  15
```

Pro Cys Lys Asp Ala Gly Met Arg Phe Gly Lys Cys Met Asn Gly Lys
            20                  25                  30

Cys His Cys Thr Pro Leu
            35

<210> SEQ ID NO 38
<211> LENGTH: 38
<212> TYPE: PRT
<213> ORGANISM: Artificial sequence
<220> FEATURE:
<223> OTHER INFORMATION: Odk2 variant

<400> SEQUENCE: 38

Gly Val Pro Thr Asp Val Lys Cys Arg Ile Ser Arg Gln Cys His Lys
1               5                   10                  15

Pro Cys Lys Asp Ala Gly Met Arg Phe Gly Lys Cys Met Asn Gly Lys
            20                  25                  30

Cys His Cys Thr Pro Lys
            35

<210> SEQ ID NO 39
<211> LENGTH: 38
<212> TYPE: PRT
<213> ORGANISM: Artificial sequence
<220> FEATURE:
<223> OTHER INFORMATION: Odk2 variant

<400> SEQUENCE: 39

Gly Val Pro Thr Asp Val Lys Cys Arg Ile Ser Arg Gln Cys Leu Leu
1               5                   10                  15

Pro Cys Lys Asp Ala Gly Met Arg Phe Gly Lys Cys Met Asn Gly Lys
            20                  25                  30

Cys His Cys Thr Pro Lys
            35

<210> SEQ ID NO 40
<211> LENGTH: 38
<212> TYPE: PRT
<213> ORGANISM: Artificial sequence
<220> FEATURE:
<223> OTHER INFORMATION: Odk2 variant

<400> SEQUENCE: 40

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys Gln Cys Thr Pro Lys
            35

<210> SEQ ID NO 41
<211> LENGTH: 38
<212> TYPE: PRT
<213> ORGANISM: Artificial sequence
<220> FEATURE:
<223> OTHER INFORMATION: Odk2 variant

<400> SEQUENCE: 41

Val Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 42
<211> LENGTH: 38
<212> TYPE: PRT
<213> ORGANISM: Artificial sequence
<220> FEATURE:
<223> OTHER INFORMATION: Odk2 variant

<400> SEQUENCE: 42

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 43
<211> LENGTH: 38
<212> TYPE: PRT
<213> ORGANISM: Artificial sequence
<220> FEATURE:
<223> OTHER INFORMATION: Odk2 variant

<400> SEQUENCE: 43

Gly Val Pro Thr Asp Val Lys Cys Lys Ile Ser Pro Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 44
<211> LENGTH: 38
<212> TYPE: PRT
<213> ORGANISM: Artificial sequence
<220> FEATURE:
<223> OTHER INFORMATION: Odk2 variant

<400> SEQUENCE: 44

Gly Val Pro Ile Asn Val Lys Cys Arg Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 45
<211> LENGTH: 38
<212> TYPE: PRT
<213> ORGANISM: Artificial sequence
<220> FEATURE:
<223> OTHER INFORMATION: Odk2 variant

<400> SEQUENCE: 45

Gly Val Pro Thr Asp Val Lys Cys Lys Ile Ser Arg Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 46
<211> LENGTH: 38
<212> TYPE: PRT
<213> ORGANISM: Artificial sequence
<220> FEATURE:
<223> OTHER INFORMATION: Odk2 variant

<400> SEQUENCE: 46

Gly Val Pro Ile Asp Val Lys Cys Arg Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 47
<211> LENGTH: 38
<212> TYPE: PRT
<213> ORGANISM: Artificial sequence
<220> FEATURE:
<223> OTHER INFORMATION: Odk2 variant

<400> SEQUENCE: 47

Gly Val Pro Thr Asp Val Lys Cys Arg Ile Ser Arg Gln Cys Leu Lys
1               5                   10                  15

Pro Cys Gln Asp Ala Gly Met Arg Phe Gly Lys Cys Met Asn Gly Lys
            20                  25                  30

Cys His Cys Thr Pro Lys
        35

<210> SEQ ID NO 48
<211> LENGTH: 38
<212> TYPE: PRT
<213> ORGANISM: Artificial sequence
<220> FEATURE:
<223> OTHER INFORMATION: Odk2 variant

<400> SEQUENCE: 48

Gly Val Pro Thr Asp Val Asp Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 49
<211> LENGTH: 38
<212> TYPE: PRT
<213> ORGANISM: Artificial sequence
<220> FEATURE:
<223> OTHER INFORMATION: Odk2 variant

<400> SEQUENCE: 49

Gly Val Pro Thr Asp Val Lys Cys Arg Ile Ser Arg Gln Cys Leu Asp
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 50
<211> LENGTH: 38

```
<212> TYPE: PRT
<213> ORGANISM: Artificial sequence
<220> FEATURE:
<223> OTHER INFORMATION: Odk2 variant

<400> SEQUENCE: 50

Gly Val Pro Thr Asp Val Lys Cys Arg Ile Ser Arg Gln Cys Leu Lys
1               5                   10                  15

Leu Cys Lys Asp Ala Gly Met Arg Phe Gly Lys Cys Met Asn Gly Lys
            20                  25                  30

Cys His Cys Thr Pro Lys
        35

<210> SEQ ID NO 51
<211> LENGTH: 38
<212> TYPE: PRT
<213> ORGANISM: Artificial sequence
<220> FEATURE:
<223> OTHER INFORMATION: Odk2 variant

<400> SEQUENCE: 51

Gly Val Pro Thr Asp Val Lys Cys Arg Ile Ser Arg Gln Cys Leu Val
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 52
<211> LENGTH: 38
<212> TYPE: PRT
<213> ORGANISM: Artificial sequence
<220> FEATURE:
<223> OTHER INFORMATION: Odk2 variant

<400> SEQUENCE: 52

Asp Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 53
<211> LENGTH: 38
<212> TYPE: PRT
<213> ORGANISM: Artificial sequence
<220> FEATURE:
<223> OTHER INFORMATION: Odk2 variant

<400> SEQUENCE: 53

Gly Val Pro Thr Asp Val Lys Cys Arg Ile Ser Arg Gln Cys Leu Lys
1               5                   10                  15

Pro Cys Lys Asp Ala Gly Asp Arg Phe Gly Lys Cys Met Asn Gly Lys
            20                  25                  30

Cys His Cys Thr Pro Lys
        35

<210> SEQ ID NO 54
<211> LENGTH: 38
<212> TYPE: PRT
<213> ORGANISM: Artificial sequence
<220> FEATURE:
```

<223> OTHER INFORMATION: Odk2 variant

<400> SEQUENCE: 54

Gln Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 55
<211> LENGTH: 38
<212> TYPE: PRT
<213> ORGANISM: Artificial sequence
<220> FEATURE:
<223> OTHER INFORMATION: Odk2 variant

<400> SEQUENCE: 55

Gly Val Pro Ile Asn Val Lys Cys Lys Gly Ser Pro Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 56
<211> LENGTH: 38
<212> TYPE: PRT
<213> ORGANISM: Artificial sequence
<220> FEATURE:
<223> OTHER INFORMATION: Odk2 variant

<400> SEQUENCE: 56

Gly Val Pro Thr Asp Val Lys Cys Arg Ile Ser Arg Gln Cys Leu Lys
1               5                   10                  15

Pro Cys Lys Asp Ala Asp Met Arg Phe Gly Lys Cys Met Asn Gly Lys
            20                  25                  30

Cys His Cys Thr Pro Lys
        35

<210> SEQ ID NO 57
<211> LENGTH: 38
<212> TYPE: PRT
<213> ORGANISM: Artificial sequence
<220> FEATURE:
<223> OTHER INFORMATION: Odk2 variant

<400> SEQUENCE: 57

Gly Val Pro Thr Asp Val Gln Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 58
<211> LENGTH: 38
<212> TYPE: PRT
<213> ORGANISM: Artificial sequence
<220> FEATURE:
<223> OTHER INFORMATION: Odk2 variant

<400> SEQUENCE: 58

```
Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr His Lys
        35
```

<210> SEQ ID NO 59
<211> LENGTH: 38
<212> TYPE: PRT
<213> ORGANISM: Artificial sequence
<220> FEATURE:
<223> OTHER INFORMATION: Odk2 variant

<400> SEQUENCE: 59

```
Gly Val Pro Thr Asp Val Lys Cys Gln Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35
```

<210> SEQ ID NO 60
<211> LENGTH: 38
<212> TYPE: PRT
<213> ORGANISM: Artificial sequence
<220> FEATURE:
<223> OTHER INFORMATION: Odk2 variant

<400> SEQUENCE: 60

```
Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Asp Lys
            20                  25                  30

Cys His Cys Thr Pro Lys
        35
```

<210> SEQ ID NO 61
<211> LENGTH: 38
<212> TYPE: PRT
<213> ORGANISM: Artificial sequence
<220> FEATURE:
<223> OTHER INFORMATION: Odk2 variant

<400> SEQUENCE: 61

```
Gly Val Pro Thr Asp Val Ala Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35
```

<210> SEQ ID NO 62
<211> LENGTH: 38
<212> TYPE: PRT
<213> ORGANISM: Artificial sequence
<220> FEATURE:
<223> OTHER INFORMATION: Odk2 variant

<400> SEQUENCE: 62

```
Gly Val Pro Thr Asp Val Lys Cys Arg Ile Ser Arg Gln Cys Leu Lys
1               5                   10                  15
```

```
Pro Cys Lys Asp Ala Gly Met Arg Phe Gly Lys Cys Met Asn Gly Lys
            20                  25                  30

Cys His Cys Thr Pro His
        35

<210> SEQ ID NO 63
<211> LENGTH: 38
<212> TYPE: PRT
<213> ORGANISM: Artificial sequence
<220> FEATURE:
<223> OTHER INFORMATION: Odk2  variant

<400> SEQUENCE: 63

Gly Val Pro Thr Asn Val Lys Cys Lys Ile Ser Arg Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 64
<211> LENGTH: 38
<212> TYPE: PRT
<213> ORGANISM: Artificial sequence
<220> FEATURE:
<223> OTHER INFORMATION: Odk2  variant

<400> SEQUENCE: 64

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Asp
            20                  25                  30

Cys His Cys Thr Pro Lys
        35

<210> SEQ ID NO 65
<211> LENGTH: 38
<212> TYPE: PRT
<213> ORGANISM: Artificial sequence
<220> FEATURE:
<223> OTHER INFORMATION: Odk2  variant

<400> SEQUENCE: 65

Gly Val Pro Thr Asp Val Lys Cys Arg Ile Ser Arg Gln Cys Val Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 66
<211> LENGTH: 38
<212> TYPE: PRT
<213> ORGANISM: Artificial sequence
<220> FEATURE:
<223> OTHER INFORMATION: Odk2  variant

<400> SEQUENCE: 66

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Gln
            20                  25                  30
```

Cys His Cys Thr Pro Lys
        35

<210> SEQ ID NO 67
<211> LENGTH: 38
<212> TYPE: PRT
<213> ORGANISM: Artificial sequence
<220> FEATURE:
<223> OTHER INFORMATION: Odk2 variant

<400> SEQUENCE: 67

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly His
            20                  25                  30

Cys His Cys Thr Pro Lys
        35

<210> SEQ ID NO 68
<211> LENGTH: 38
<212> TYPE: PRT
<213> ORGANISM: Artificial sequence
<220> FEATURE:
<223> OTHER INFORMATION: Odk2 variant

<400> SEQUENCE: 68

Gly Val Pro Thr Asp Ala Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 69
<211> LENGTH: 38
<212> TYPE: PRT
<213> ORGANISM: Artificial sequence
<220> FEATURE:
<223> OTHER INFORMATION: Odk2 variant

<400> SEQUENCE: 69

Gly Val Pro Ile Asp Val Lys Cys Lys Ile Ser Arg Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 70
<211> LENGTH: 38
<212> TYPE: PRT
<213> ORGANISM: Artificial sequence
<220> FEATURE:
<223> OTHER INFORMATION: Odk2 variant

<400> SEQUENCE: 70

Gly Val Pro Thr Asp Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 71
<211> LENGTH: 38
<212> TYPE: PRT
<213> ORGANISM: Artificial sequence
<220> FEATURE:
<223> OTHER INFORMATION: Odk2 variant

<400> SEQUENCE: 71

Gly Val Pro Ile Asn Val Lys Cys Lys Ile Ser Pro Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 72
<211> LENGTH: 38
<212> TYPE: PRT
<213> ORGANISM: Artificial sequence
<220> FEATURE:
<223> OTHER INFORMATION: Odk2 variant

<400> SEQUENCE: 72

Gly Val Ile Thr Asp Val Lys Cys Arg Ile Ser Pro Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 73
<211> LENGTH: 38
<212> TYPE: PRT
<213> ORGANISM: Artificial sequence
<220> FEATURE:
<223> OTHER INFORMATION: Odk2 variant

<400> SEQUENCE: 73

Gly Val Pro Ile Asn Val Lys Cys Lys Ile Ser Pro Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 74
<211> LENGTH: 38
<212> TYPE: PRT
<213> ORGANISM: Artificial sequence
<220> FEATURE:
<223> OTHER INFORMATION: Odk2 variant

<400> SEQUENCE: 74

Gly Val Pro Thr Asp Val Leu Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 75

<211> LENGTH: 38
<212> TYPE: PRT
<213> ORGANISM: Artificial sequence
<220> FEATURE:
<223> OTHER INFORMATION: Odk2 variant

<400> SEQUENCE: 75

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Val Lys
        35

<210> SEQ ID NO 76
<211> LENGTH: 38
<212> TYPE: PRT
<213> ORGANISM: Artificial sequence
<220> FEATURE:
<223> OTHER INFORMATION: Odk2 variant

<400> SEQUENCE: 76

Gly Val Pro Thr Asp Val Lys Cys Arg Ile Ser Arg Gln Cys Lys Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 77
<211> LENGTH: 38
<212> TYPE: PRT
<213> ORGANISM: Artificial sequence
<220> FEATURE:
<223> OTHER INFORMATION: Odk2 variant

<400> SEQUENCE: 77

Gly Val Pro Thr Asp Val Lys Cys Arg Ile Ser Arg Gln Cys Leu Lys
1               5                   10                  15

Pro Cys Lys Asp Ala Arg Met Arg Phe Gly Lys Cys Met Asn Gly Lys
            20                  25                  30

Cys His Cys Thr Pro Lys
        35

<210> SEQ ID NO 78
<211> LENGTH: 38
<212> TYPE: PRT
<213> ORGANISM: Artificial sequence
<220> FEATURE:
<223> OTHER INFORMATION: Odk2 variant

<400> SEQUENCE: 78

Gly Val Pro Gln Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 79
<211> LENGTH: 38
<212> TYPE: PRT
<213> ORGANISM: Artificial sequence
<220> FEATURE:
<223> OTHER INFORMATION: Odk2 variant

<400> SEQUENCE: 79

Gly Val Pro Thr Asp Val Lys Cys Arg Ile Ser Arg Gln Cys Leu Lys
1               5                   10                  15

Pro Cys Lys Asp Ala Glu Met Arg Phe Gly Lys Cys Met Asn Gly Lys
            20                  25                  30

Cys His Cys Thr Pro Lys
        35

<210> SEQ ID NO 80
<211> LENGTH: 38
<212> TYPE: PRT
<213> ORGANISM: Artificial sequence
<220> FEATURE:
<223> OTHER INFORMATION: Odk2 variant

<400> SEQUENCE: 80

Gly Val Pro Thr Asp Val Lys Cys Arg Ile Ser Arg Gln Cys Leu Lys
1               5                   10                  15

Pro Cys Lys Asp Ala His Met Arg Phe Gly Lys Cys Met Asn Gly Lys
            20                  25                  30

Cys His Cys Thr Pro Lys
        35

<210> SEQ ID NO 81
<211> LENGTH: 38
<212> TYPE: PRT
<213> ORGANISM: Artificial sequence
<220> FEATURE:
<223> OTHER INFORMATION: Odk2 variant

<400> SEQUENCE: 81

Gly Val Pro Thr Asp Val Lys Cys Arg Ile Ser Arg Gln Cys Ala Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 82
<211> LENGTH: 38
<212> TYPE: PRT
<213> ORGANISM: Artificial sequence
<220> FEATURE:
<223> OTHER INFORMATION: Odk2 variant

<400> SEQUENCE: 82

Gly Val Pro Thr Asp Val Lys Cys Arg Ile Ser Arg Gln Cys Leu Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 83
<211> LENGTH: 38
<212> TYPE: PRT
<213> ORGANISM: Artificial sequence
<220> FEATURE:
<223> OTHER INFORMATION: Odk2 variant -continued

<400> SEQUENCE: 83

Gly Val Pro Thr Asp Val Lys Cys Arg Ile Ser Arg Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 84
<211> LENGTH: 38
<212> TYPE: PRT
<213> ORGANISM: Artificial sequence
<220> FEATURE:
<223> OTHER INFORMATION: Odk2 variant

<400> SEQUENCE: 84

Gly Val Pro Ile Asn Val Lys Cys Lys Ile Ser Arg Gln Cys Ile Glu
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 85
<211> LENGTH: 38
<212> TYPE: PRT
<213> ORGANISM: Artificial sequence
<220> FEATURE:
<223> OTHER INFORMATION: Odk2 variant

<400> SEQUENCE: 85

Gly Val Pro Thr Asn Val Lys Cys Arg Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 86
<211> LENGTH: 38
<212> TYPE: PRT
<213> ORGANISM: Artificial sequence
<220> FEATURE:
<223> OTHER INFORMATION: Odk2 variant

<400> SEQUENCE: 86

Gly Val Ile Ile Asp Val Lys Cys Arg Gly Ser Arg Gln Cys Ile Glu
1               5                   10                  15

Pro Cys Lys Asp Ala Gly Met Arg Phe Gly Lys Cys Met Asn Gly Lys
            20                  25                  30

Cys Asn Cys Thr Pro Lys
        35

<210> SEQ ID NO 87
<211> LENGTH: 38
<212> TYPE: PRT
<213> ORGANISM: Artificial sequence
<220> FEATURE:
<223> OTHER INFORMATION: Odk2 variant

<400> SEQUENCE: 87

Gly Val Pro Thr Asn Val Lys Cys Arg Ile Ser Pro Gln Cys Ile Glu

```
                1               5                  10                  15
Pro Cys Lys Asp Ala Gly Met Arg Phe Gly Lys Cys Met Asn Gly Lys
            20                  25                  30

Cys His Cys Thr Pro Lys
            35

<210> SEQ ID NO 88
<211> LENGTH: 38
<212> TYPE: PRT
<213> ORGANISM: Artificial sequence
<220> FEATURE:
<223> OTHER INFORMATION: Odk2 variant

<400> SEQUENCE: 88

Gly Val Pro Thr Asn Val Lys Cys Lys Ile Ser Pro Gln Cys Ile Glu
1               5                  10                  15

Pro Cys Lys Lys Ala Gly Met Arg Phe Gly Lys Cys Met Asn Gly Lys
            20                  25                  30

Cys His Cys Thr Pro Lys
            35

<210> SEQ ID NO 89
<211> LENGTH: 38
<212> TYPE: PRT
<213> ORGANISM: Artificial sequence
<220> FEATURE:
<223> OTHER INFORMATION: Odk2 variant

<400> SEQUENCE: 89

Gly Val Pro Thr Asp Val Lys Cys Arg Ile Ser Pro Gln Cys Ile Gln
1               5                  10                  15

Pro Cys Lys Asp Ala Gly Met Arg Phe Gly Lys Cys Met Asn Gly Lys
            20                  25                  30

Cys His Cys Thr Pro Lys
            35

<210> SEQ ID NO 90
<211> LENGTH: 38
<212> TYPE: PRT
<213> ORGANISM: Artificial sequence
<220> FEATURE:
<223> OTHER INFORMATION: Odk2 variant

<400> SEQUENCE: 90

Gly Val Pro Ile Asn Val Lys Cys Arg Ile Ser Pro Gln Cys Ile Glu
1               5                  10                  15

Pro Cys Lys Asp Ala Gly Met Arg Phe Gly Lys Cys Met Asn Gly Lys
            20                  25                  30

Cys His Cys Thr Pro Lys
            35

<210> SEQ ID NO 91
<211> LENGTH: 38
<212> TYPE: PRT
<213> ORGANISM: Artificial sequence
<220> FEATURE:
<223> OTHER INFORMATION: Odk2 variant

<400> SEQUENCE: 91

Ala Val Pro Thr Asp Val Lys Cys Arg Ile Ser Arg Gln Cys Leu Lys
1               5                  10                  15

Pro Cys Lys Asp Ala Gly Met Arg Phe Gly Lys Cys Met Asn Gly Lys
```

```
                        20                  25                  30

Cys His Cys Thr Pro Lys
        35

<210> SEQ ID NO 92
<211> LENGTH: 38
<212> TYPE: PRT
<213> ORGANISM: Artificial sequence
<220> FEATURE:
<223> OTHER INFORMATION: Odk2 variant

<400> SEQUENCE: 92

Gly Val Pro Thr Asp Val Lys Cys Arg Ile Ser Arg Gln Cys Leu Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 93
<211> LENGTH: 38
<212> TYPE: PRT
<213> ORGANISM: Artificial sequence
<220> FEATURE:
<223> OTHER INFORMATION: Odk2 variant

<400> SEQUENCE: 93

Gly Val Val Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 94
<211> LENGTH: 38
<212> TYPE: PRT
<213> ORGANISM: Artificial sequence
<220> FEATURE:
<223> OTHER INFORMATION: Odk2 variant

<400> SEQUENCE: 94

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Gln
        35

<210> SEQ ID NO 95
<211> LENGTH: 38
<212> TYPE: PRT
<213> ORGANISM: Artificial sequence
<220> FEATURE:
<223> OTHER INFORMATION: Odk2 variant

<400> SEQUENCE: 95

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Glu Lys
            20                  25                  30

Cys His Cys Thr Pro Lys
```

-continued

```
        35

<210> SEQ ID NO 96
<211> LENGTH: 38
<212> TYPE: PRT
<213> ORGANISM: Artificial sequence
<220> FEATURE:
<223> OTHER INFORMATION: Odk2 variant

<400> SEQUENCE: 96

Gly Val Pro Glu Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 97
<211> LENGTH: 38
<212> TYPE: PRT
<213> ORGANISM: Artificial sequence
<220> FEATURE:
<223> OTHER INFORMATION: Odk2 variant

<400> SEQUENCE: 97

Gly Val Pro Ile Asn Val Lys Cys Lys Ile Ser Arg Gln Cys Ile Gln
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 98
<211> LENGTH: 38
<212> TYPE: PRT
<213> ORGANISM: Artificial sequence
<220> FEATURE:
<223> OTHER INFORMATION: Odk2 variant

<400> SEQUENCE: 98

Gly Val Pro Thr Asn Val Lys Cys Lys Ile Ser Arg Gln Cys Ile Gln
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 99
<211> LENGTH: 38
<212> TYPE: PRT
<213> ORGANISM: Artificial sequence
<220> FEATURE:
<223> OTHER INFORMATION: Odk2 variant

<400> SEQUENCE: 99

Gly Val Pro Thr Asn Val Lys Cys Lys Ile Ser Arg Gln Cys Ile Glu
1               5                   10                  15

Pro Cys Lys Lys Ala Gly Met Arg Phe Gly Lys Cys Met Asn Gly Lys
            20                  25                  30

Cys His Cys Thr Pro Lys
        35
```

```
<210> SEQ ID NO 100
<211> LENGTH: 38
<212> TYPE: PRT
<213> ORGANISM: Artificial sequence
<220> FEATURE:
<223> OTHER INFORMATION: Odk2 variant

<400> SEQUENCE: 100

Gly Val Pro Ile Asn Val Lys Cys Arg Ile Ser Arg Gln Cys Ile Glu
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 101
<211> LENGTH: 38
<212> TYPE: PRT
<213> ORGANISM: Artificial sequence
<220> FEATURE:
<223> OTHER INFORMATION: Odk2 variant

<400> SEQUENCE: 101

Gly Val Pro Ile Asn Val Lys Cys Arg Ile Ser Arg Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 102
<211> LENGTH: 38
<212> TYPE: PRT
<213> ORGANISM: Artificial sequence
<220> FEATURE:
<223> OTHER INFORMATION: Odk2 variant

<400> SEQUENCE: 102

Gly Val Pro Ile Asp Val Lys Cys Arg Ile Ser Arg Gln Cys Ile Glu
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 103
<211> LENGTH: 38
<212> TYPE: PRT
<213> ORGANISM: Artificial sequence
<220> FEATURE:
<223> OTHER INFORMATION: Odk2 variant

<400> SEQUENCE: 103

Gly Val Pro Thr Asn Val Lys Cys Arg Ile Ser Arg Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 104
<211> LENGTH: 38
<212> TYPE: PRT
```

```
<213> ORGANISM: Artificial sequence
<220> FEATURE:
<223> OTHER INFORMATION: Odk2 variant

<400> SEQUENCE: 104

Gly Val Pro Ile Asn Val Lys Cys Lys Ile Ser Arg Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 105
<211> LENGTH: 38
<212> TYPE: PRT
<213> ORGANISM: Artificial sequence
<220> FEATURE:
<223> OTHER INFORMATION: Odk2 variant

<400> SEQUENCE: 105

Gly Val Ile Thr Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 106
<211> LENGTH: 38
<212> TYPE: PRT
<213> ORGANISM: Artificial sequence
<220> FEATURE:
<223> OTHER INFORMATION: Odk2 variant

<400> SEQUENCE: 106

Gly Val Pro Thr Asp Val Lys Cys Lys Ile Ser Arg Gln Cys Ile Glu
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 107
<211> LENGTH: 38
<212> TYPE: PRT
<213> ORGANISM: Artificial sequence
<220> FEATURE:
<223> OTHER INFORMATION: Odk2 variant

<400> SEQUENCE: 107

Gly Val Pro Ile Asp Val Lys Cys Arg Ile Ser Pro Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 108
<211> LENGTH: 38
<212> TYPE: PRT
<213> ORGANISM: Artificial sequence
<220> FEATURE:
<223> OTHER INFORMATION: Odk2 variant
```

-continued

```
<400> SEQUENCE: 108

Gly Val Pro Thr Asp Val Lys Cys Arg Ile Ser Arg Gln Cys Leu His
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 109
<211> LENGTH: 38
<212> TYPE: PRT
<213> ORGANISM: Artificial sequence
<220> FEATURE:
<223> OTHER INFORMATION: Odk2 variant

<400> SEQUENCE: 109

Gly Val Pro Thr Asp Val Lys Cys Arg Ile Ser Arg Gln Cys Leu Lys
1               5                   10                  15

Pro Cys Lys Asp Gln Gly Met Arg Phe Gly Lys Cys Met Asn Gly Lys
            20                  25                  30

Cys His Cys Thr Pro Lys
        35

<210> SEQ ID NO 110
<211> LENGTH: 38
<212> TYPE: PRT
<213> ORGANISM: Artificial sequence
<220> FEATURE:
<223> OTHER INFORMATION: Odk2 variant

<400> SEQUENCE: 110

Gly Val Pro Thr Asp Val Lys Cys Arg Ile Ser Arg Gln Cys Leu Lys
1               5                   10                  15

Pro Cys Lys Asp Ala Gly Leu Arg Phe Gly Lys Cys Met Asn Gly Lys
            20                  25                  30

Cys His Cys Thr Pro Lys
        35

<210> SEQ ID NO 111
<211> LENGTH: 38
<212> TYPE: PRT
<213> ORGANISM: Artificial sequence
<220> FEATURE:
<223> OTHER INFORMATION: Odk2 variant

<400> SEQUENCE: 111

Gly Val Pro Thr Asp Val Lys Cys Arg Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 112
<211> LENGTH: 38
<212> TYPE: PRT
<213> ORGANISM: Artificial sequence
<220> FEATURE:
<223> OTHER INFORMATION: Linker

<400> SEQUENCE: 112
```

```
Ala Ser Leu Asp Thr Thr Ala Glu Asn Gln Ala Lys Asn Glu His Leu
1               5                  10                  15

Gln Lys Glu Asn Glu Arg Leu Leu Arg Asp Trp Asn Asp Val Gln Gly
            20                  25                  30

Arg Phe Glu Lys Gly Ser
            35

<210> SEQ ID NO 113
<211> LENGTH: 30
<212> TYPE: PRT
<213> ORGANISM: Artificial sequence
<220> FEATURE:
<223> OTHER INFORMATION: Linker

<400> SEQUENCE: 113

Ala Ser Glu Lys Asn Lys Arg Ser Thr Pro Tyr Ile Glu Arg Ala Glu
1               5                  10                  15

Lys Asn Lys Arg Ser Thr Pro Tyr Ile Glu Arg Ala Gly Ser
            20                  25                  30

<210> SEQ ID NO 114
<211> LENGTH: 43
<212> TYPE: PRT
<213> ORGANISM: Artificial sequence
<220> FEATURE:
<223> OTHER INFORMATION: Linker

<400> SEQUENCE: 114

Ala Ser Glu Lys Asn Lys Arg Ser Thr Pro Tyr Ile Glu Arg Ala Glu
1               5                  10                  15

Lys Asn Lys Arg Ser Thr Pro Tyr Ile Glu Arg Ala Glu Lys Asn Lys
            20                  25                  30

Arg Ser Thr Pro Tyr Ile Glu Arg Ala Gly Ser
            35                  40

<210> SEQ ID NO 115
<211> LENGTH: 24
<212> TYPE: PRT
<213> ORGANISM: Artificial sequence
<220> FEATURE:
<223> OTHER INFORMATION: Linker

<400> SEQUENCE: 115

Ala Ser Ala Pro Ala Pro Ala Pro Ala Pro Ala Pro Ala Pro Ala Pro
1               5                  10                  15

Ala Pro Ala Pro Ala Pro Gly Ser
            20

<210> SEQ ID NO 116
<211> LENGTH: 44
<212> TYPE: PRT
<213> ORGANISM: Artificial sequence
<220> FEATURE:
<223> OTHER INFORMATION: Linker

<400> SEQUENCE: 116

Ala Ser Ala Pro Ala Pro Ala Pro Ala Pro Ala Pro Ala Pro Ala Pro
1               5                  10                  15

Ala Pro Ala Pro Ala Pro Ala Pro Ala Pro Ala Pro Ala Pro Ala Pro
            20                  25                  30

Ala Pro Ala Pro Ala Pro Ala Pro Ala Pro Gly Ser
            35                  40
```

<210> SEQ ID NO 117
<211> LENGTH: 26
<212> TYPE: PRT
<213> ORGANISM: Artificial sequence
<220> FEATURE:
<223> OTHER INFORMATION: Linker

<400> SEQUENCE: 117

Ala Ser Ala Glu Ala Ala Ala Lys Glu Ala Ala Ala Lys Glu Ala Ala
1               5                   10                  15

Ala Lys Glu Ala Ala Ala Lys Ala Gly Ser
            20                  25

<210> SEQ ID NO 118
<211> LENGTH: 46
<212> TYPE: PRT
<213> ORGANISM: Artificial sequence
<220> FEATURE:
<223> OTHER INFORMATION: Linker

<400> SEQUENCE: 118

Ala Ser Ala Glu Ala Ala Ala Lys Glu Ala Ala Ala Lys Glu Ala Ala
1               5                   10                  15

Ala Lys Glu Ala Ala Ala Lys Glu Ala Ala Ala Lys Glu Ala Ala Ala
            20                  25                  30

Lys Glu Ala Ala Ala Lys Glu Ala Ala Lys Ala Gly Ser
        35                  40                  45

<210> SEQ ID NO 119
<211> LENGTH: 22
<212> TYPE: PRT
<213> ORGANISM: Artificial sequence
<220> FEATURE:
<223> OTHER INFORMATION: Linker

<400> SEQUENCE: 119

Gly Ser Gly Gly Gly Gly Ser Gly Gly Gly Ser Gly Gly Gly Gly
1               5                   10                  15

Ser Gly Gly Gly Gly Ser
            20

<210> SEQ ID NO 120
<211> LENGTH: 42
<212> TYPE: PRT
<213> ORGANISM: Artificial sequence
<220> FEATURE:
<223> OTHER INFORMATION: Linker

<400> SEQUENCE: 120

Gly Ser Gly Gly Gly Gly Ser Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser
        35                  40

<210> SEQ ID NO 121
<211> LENGTH: 62
<212> TYPE: PRT
<213> ORGANISM: Artificial sequence
<220> FEATURE:
<223> OTHER INFORMATION: Linker

<400> SEQUENCE: 121

```
Gly Ser Gly Gly Gly Ser Gly Gly Gly Ser Gly Gly Gly Gly
1               5                   10                  15

Ser Gly Gly Gly Gly Ser Gly Gly Gly Ser Gly Gly Gly Ser
                20                  25                  30

Gly Gly Gly Gly Ser Gly Gly Gly Ser Gly Gly Gly Ser Gly
        35                  40                  45

Gly Gly Gly Ser Gly Gly Gly Ser Gly Gly Gly Ser
    50                  55                  60

<210> SEQ ID NO 122
<211> LENGTH: 82
<212> TYPE: PRT
<213> ORGANISM: Artificial sequence
<220> FEATURE:
<223> OTHER INFORMATION: Linker

<400> SEQUENCE: 122

Gly Ser Gly Gly Gly Gly Ser Gly Gly Gly Ser Gly Gly Gly Gly
1               5                   10                  15

Ser Gly Gly Gly Gly Ser Gly Gly Gly Ser Gly Gly Gly Gly Ser
                20                  25                  30

Gly Gly Gly Gly Ser Gly Gly Gly Ser Gly Gly Gly Ser Gly
        35                  40                  45

Gly Gly Gly Ser Gly Gly Gly Ser Gly Gly Gly Ser Gly Gly
    50                  55                  60

Gly Gly Ser Gly Gly Gly Ser Gly Gly Gly Ser Gly Gly Gly
65                  70                  75                  80

Gly Ser

<210> SEQ ID NO 123
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 123

His Ala Ala Gly
1

<210> SEQ ID NO 124
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 124

Arg Arg Pro Thr
1

<210> SEQ ID NO 125
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 125

Ala Ser Lys Pro
1
```

```
<210> SEQ ID NO 126
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 126

Pro Lys Pro Gln
1

<210> SEQ ID NO 127
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 127

Gln Asp Gln Thr
1

<210> SEQ ID NO 128
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 128

Ala His Arg Pro
1

<210> SEQ ID NO 129
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 129

Gln Pro Thr His
1

<210> SEQ ID NO 130
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 130

Arg Glu Gln Thr
1

<210> SEQ ID NO 131
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 131

Pro Pro Lys Pro
1
```

```
<210> SEQ ID NO 132
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 132

Lys Gln Gly Ala
1

<210> SEQ ID NO 133
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 133

Thr Arg Pro Ala
1

<210> SEQ ID NO 134
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 134

Ala Pro His Lys
1

<210> SEQ ID NO 135
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 135

Arg Thr Glu His
1

<210> SEQ ID NO 136
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 136

Pro Thr His Thr
1

<210> SEQ ID NO 137
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 137

Arg Ala Glu Lys
1

<210> SEQ ID NO 138
```

```
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 138

Pro Ala Pro Ala
1

<210> SEQ ID NO 139
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 139

Ser His Arg Pro
1

<210> SEQ ID NO 140
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 140

Ser His Arg Pro
1

<210> SEQ ID NO 141
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 141

Pro Pro Thr Arg
1

<210> SEQ ID NO 142
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 142

His His Thr Thr
1

<210> SEQ ID NO 143
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 143

His Arg Pro Ala
1

<210> SEQ ID NO 144
<211> LENGTH: 4
```

```
<212> TYPE: PRT
<213> ORGANISM: Artificial sequence
<220> FEATURE:
<223> OTHER INFORMATION: C-terminal peptide extension

<400> SEQUENCE: 144

Lys Ala His Pro
1

<210> SEQ ID NO 145
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 145

Gln Thr Thr Gln
1

<210> SEQ ID NO 146
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 146

Pro Thr Pro Thr
1

<210> SEQ ID NO 147
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 147

Thr Gln Ala Pro
1

<210> SEQ ID NO 148
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 148

Arg Lys Pro His
1

<210> SEQ ID NO 149
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 149

His Thr Pro Pro
1

<210> SEQ ID NO 150
<211> LENGTH: 4
<212> TYPE: PRT
```

```
<213> ORGANISM: Artificial sequence
<220> FEATURE:
<223> OTHER INFORMATION: C-terminal peptide extension

<400> SEQUENCE: 150

Thr Lys Pro Pro
1

<210> SEQ ID NO 151
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 151

Pro Arg Pro Thr
1

<210> SEQ ID NO 152
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 152

Lys Gln Thr Ala
1

<210> SEQ ID NO 153
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 153

Pro His Thr Pro
1

<210> SEQ ID NO 154
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 154

His Thr Pro Pro
1

<210> SEQ ID NO 155
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 155

His Ala Lys Pro
1

<210> SEQ ID NO 156
<211> LENGTH: 4
<212> TYPE: PRT
<213> ORGANISM: Artificial sequence
```

```
<220> FEATURE:
<223> OTHER INFORMATION: C-terminal peptide extension

<400> SEQUENCE: 156

Thr Arg Arg Pro
1

<210> SEQ ID NO 157
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 157

Pro Thr Thr Pro
1

<210> SEQ ID NO 158
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 158

Arg Gln His Ala
1

<210> SEQ ID NO 159
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 159

Pro Thr Arg Pro
1

<210> SEQ ID NO 160
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 160

Pro Ala Pro His
1

<210> SEQ ID NO 161
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 161

Ala Asp Lys Pro
1

<210> SEQ ID NO 162
<211> LENGTH: 4
<212> TYPE: PRT
<213> ORGANISM: Artificial sequence
<220> FEATURE:
```

```
<223> OTHER INFORMATION: C-terminal peptide extension

<400> SEQUENCE: 162

Pro His His Gln
1

<210> SEQ ID NO 163
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 163

Gly Arg Arg Thr
1

<210> SEQ ID NO 164
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 164

Arg Pro Asp Ala
1

<210> SEQ ID NO 165
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 165

Asn His Arg Pro
1

<210> SEQ ID NO 166
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 166

Asn His Gln Gly
1

<210> SEQ ID NO 167
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 167

Thr Ala Pro Pro
1

<210> SEQ ID NO 168
<211> LENGTH: 4
<212> TYPE: PRT
<213> ORGANISM: Artificial sequence
<220> FEATURE:
<223> OTHER INFORMATION: C-terminal peptide extension
```

<400> SEQUENCE: 168

Arg His Pro His
1

<210> SEQ ID NO 169
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 169

Pro Ser Arg Pro
1

<210> SEQ ID NO 170
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 170

Pro Gln His Gln
1

<210> SEQ ID NO 171
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 171

Pro Thr Gln His
1

<210> SEQ ID NO 172
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 172

His Thr Lys Pro
1

<210> SEQ ID NO 173
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 173

Arg Lys Lys Pro
1

<210> SEQ ID NO 174
<211> LENGTH: 4
<212> TYPE: PRT
<213> ORGANISM: Artificial sequence
<220> FEATURE:
<223> OTHER INFORMATION: C-terminal peptide extension

```
<400> SEQUENCE: 174

His Asn Arg Pro
1

<210> SEQ ID NO 175
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 175

Pro Glu Lys Pro
1

<210> SEQ ID NO 176
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 176

Arg Ala Gln Thr
1

<210> SEQ ID NO 177
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 177

Pro Ala Ala Thr
1

<210> SEQ ID NO 178
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 178

Arg Thr Glu Gln
1

<210> SEQ ID NO 179
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 179

Pro Pro Ala Lys
1

<210> SEQ ID NO 180
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 180
```

Glu Pro Arg Pro
1

<210> SEQ ID NO 181
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 181

Thr Ala Thr His
1

<210> SEQ ID NO 182
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 182

Ala Arg Pro Asp
1

<210> SEQ ID NO 183
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 183

Ala His Pro His
1

<210> SEQ ID NO 184
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 184

Ala Ala Pro Ser
1

<210> SEQ ID NO 185
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 185

Arg Pro Arg Pro
1

<210> SEQ ID NO 186
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 186

Pro Asp Lys Pro
1

<210> SEQ ID NO 187
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 187

Thr Pro His Pro
1

<210> SEQ ID NO 188
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 188

Arg Thr Arg Pro
1

<210> SEQ ID NO 189
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 189

Ala Gln Gln His
1

<210> SEQ ID NO 190
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 190

Thr Arg Arg Pro
1

<210> SEQ ID NO 191
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 191

Thr Arg Arg Pro
1

<210> SEQ ID NO 192
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 192

Arg Gln Pro Pro

<210> SEQ ID NO 193
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 193

Arg Thr Pro Pro
1

<210> SEQ ID NO 194
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 194

Glu Lys Pro Thr
1

<210> SEQ ID NO 195
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 195

Gly His Thr Ala
1

<210> SEQ ID NO 196
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 196

Pro Thr Lys Pro
1

<210> SEQ ID NO 197
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 197

Pro Thr Thr Pro
1

<210> SEQ ID NO 198
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 198

Thr Gly His Thr
1

```
<210> SEQ ID NO 199
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 199

Gly Gly Pro Gln
1

<210> SEQ ID NO 200
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 200

His Arg Arg Gln
1

<210> SEQ ID NO 201
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 201

His Asn Ala Pro
1

<210> SEQ ID NO 202
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 202

Pro Gln Pro Gln
1

<210> SEQ ID NO 203
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 203

Asn Arg Arg Pro
1

<210> SEQ ID NO 204
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 204

Gln Ala Ala Pro
1
```

<210> SEQ ID NO 205
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 205

Gln Pro Gln Asp
1

<210> SEQ ID NO 206
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 206

Ala Thr Arg Pro
1

<210> SEQ ID NO 207
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 207

Asn Arg Pro Pro
1

<210> SEQ ID NO 208
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 208

Arg Arg Arg Pro
1

<210> SEQ ID NO 209
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 209

Ala His Arg His
1

<210> SEQ ID NO 210
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 210

Ala Gln Arg Pro
1

```
<210> SEQ ID NO 211
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 211

Thr Ser Asp Thr
1

<210> SEQ ID NO 212
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 212

Arg Arg Pro Gly
1

<210> SEQ ID NO 213
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 213

Gln Ser Lys Ala
1

<210> SEQ ID NO 214
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 214

Ala Gly Pro Arg
1

<210> SEQ ID NO 215
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 215

Arg Ser Arg Thr
1

<210> SEQ ID NO 216
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 216

Arg His Lys Arg
1

<210> SEQ ID NO 217
```

```
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 217

Asn Ala Ala Lys
1

<210> SEQ ID NO 218
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 218

Ala Pro His Thr
1

<210> SEQ ID NO 219
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 219

Gly Gly Lys Arg
1

<210> SEQ ID NO 220
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 220

Arg Arg Glu Pro
1

<210> SEQ ID NO 221
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 221

His Thr Arg Thr
1

<210> SEQ ID NO 222
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 222

Asn His Arg Thr
1

<210> SEQ ID NO 223
<211> LENGTH: 4
```

```
<212> TYPE: PRT
<213> ORGANISM: Artificial sequence
<220> FEATURE:
<223> OTHER INFORMATION: C-terminal peptide extension

<400> SEQUENCE: 223

Pro Asn Arg Thr
1

<210> SEQ ID NO 224
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 224

Pro Lys Thr Ala
1

<210> SEQ ID NO 225
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 225

Thr Arg Arg Pro
1

<210> SEQ ID NO 226
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 226

Arg His Asn Thr
1

<210> SEQ ID NO 227
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 227

Thr Asp Ala Arg
1

<210> SEQ ID NO 228
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 228

His Arg Gln Gln
1

<210> SEQ ID NO 229
<211> LENGTH: 4
<212> TYPE: PRT
```

```
<213> ORGANISM: Artificial sequence
<220> FEATURE:
<223> OTHER INFORMATION: C-terminal peptide extension

<400> SEQUENCE: 229

Asn Gln Arg Thr
1

<210> SEQ ID NO 230
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 230

Arg Pro Arg His
1

<210> SEQ ID NO 231
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 231

His Asn Glu Thr
1

<210> SEQ ID NO 232
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 232

Ala Arg Asn Ala
1

<210> SEQ ID NO 233
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 233

Thr Thr Arg Thr
1

<210> SEQ ID NO 234
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 234

Ala Arg Arg Asn
1

<210> SEQ ID NO 235
<211> LENGTH: 4
<212> TYPE: PRT
<213> ORGANISM: Artificial sequence
```

```
<220> FEATURE:
<223> OTHER INFORMATION: C-terminal peptide extension

<400> SEQUENCE: 235

Thr Gly Arg Lys
1

<210> SEQ ID NO 236
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 236

Ala Ser Asp Asn
1

<210> SEQ ID NO 237
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 237

His Glu Arg Thr
1

<210> SEQ ID NO 238
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 238

Thr Pro His Arg
1

<210> SEQ ID NO 239
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 239

Arg Arg Thr Ala
1

<210> SEQ ID NO 240
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 240

Asn Thr Arg Thr
1

<210> SEQ ID NO 241
<211> LENGTH: 4
<212> TYPE: PRT
<213> ORGANISM: Artificial sequence
<220> FEATURE:
```

<223> OTHER INFORMATION: C-terminal peptide extension

<400> SEQUENCE: 241

Pro Thr Thr Arg
1

<210> SEQ ID NO 242
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 242

Gln Arg Asn Gly
1

<210> SEQ ID NO 243
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 243

Ala His Arg Asn
1

<210> SEQ ID NO 244
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 244

Pro Arg Ser Ala
1

<210> SEQ ID NO 245
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 245

Gln Arg Gln Ser
1

<210> SEQ ID NO 246
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 246

Gln Arg Arg Lys
1

<210> SEQ ID NO 247
<211> LENGTH: 4
<212> TYPE: PRT
<213> ORGANISM: Artificial sequence
<220> FEATURE:
<223> OTHER INFORMATION: C-terminal peptide extension

```
<400> SEQUENCE: 247

Ala Arg Ala Lys
1

<210> SEQ ID NO 248
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 248

Arg Thr Arg Gln
1

<210> SEQ ID NO 249
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 249

Ala Lys Arg Asp
1

<210> SEQ ID NO 250
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 250

Asp Asp Gly Ala
1

<210> SEQ ID NO 251
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 251

Arg Asp Lys Thr
1

<210> SEQ ID NO 252
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 252

His Arg Arg Lys
1

<210> SEQ ID NO 253
<211> LENGTH: 4
<212> TYPE: PRT
<213> ORGANISM: Artificial sequence
<220> FEATURE:
<223> OTHER INFORMATION: C-terminal peptide extension
```

```
<400> SEQUENCE: 253

Arg Gln Thr Arg
1

<210> SEQ ID NO 254
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 254

Pro Asn Arg Asp
1

<210> SEQ ID NO 255
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 255

His Arg His Lys
1

<210> SEQ ID NO 256
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 256

His Arg Asn Arg
1

<210> SEQ ID NO 257
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 257

Arg Ala Lys Arg
1

<210> SEQ ID NO 258
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 258

Gln Arg Thr Arg
1

<210> SEQ ID NO 259
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 259
```

Ala Thr Arg His
1

<210> SEQ ID NO 260
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 260

Ala Arg Arg Ser
1

<210> SEQ ID NO 261
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 261

Ala Lys Thr Arg
1

<210> SEQ ID NO 262
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 262

Asn Ala Arg Gln
1

<210> SEQ ID NO 263
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 263

Asn Arg Gln Arg
1

<210> SEQ ID NO 264
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 264

Pro Thr Asn Ala
1

<210> SEQ ID NO 265
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 265

Thr Arg Thr Asp
1

<210> SEQ ID NO 266
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 266

Ala Asp Thr Arg
1

<210> SEQ ID NO 267
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 267

Thr Ser Arg Gln
1

<210> SEQ ID NO 268
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 268

Pro Arg Asn Thr
1

<210> SEQ ID NO 269
<211> LENGTH: 42
<212> TYPE: PRT
<213> ORGANISM: Artificial sequence
<220> FEATURE:
<223> OTHER INFORMATION: Odk2 variant

<400> SEQUENCE: 269

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Ala Ala Gly
        35                  40

<210> SEQ ID NO 270
<211> LENGTH: 42
<212> TYPE: PRT
<213> ORGANISM: Artificial sequence
<220> FEATURE:
<223> OTHER INFORMATION: Odk2 variant

<400> SEQUENCE: 270

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Arg Pro Thr
        35                  40

<210> SEQ ID NO 271
<211> LENGTH: 42
<212> TYPE: PRT
<213> ORGANISM: Artificial sequence
<220> FEATURE:
<223> OTHER INFORMATION: Odk2 variant

<400> SEQUENCE: 271

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Ser Lys Pro
        35                  40

<210> SEQ ID NO 272
<211> LENGTH: 42
<212> TYPE: PRT
<213> ORGANISM: Artificial sequence
<220> FEATURE:
<223> OTHER INFORMATION: Odk2 variant

<400> SEQUENCE: 272

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Lys Pro Gln
        35                  40

<210> SEQ ID NO 273
<211> LENGTH: 42
<212> TYPE: PRT
<213> ORGANISM: Artificial sequence
<220> FEATURE:
<223> OTHER INFORMATION: Odk2 variant

<400> SEQUENCE: 273

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gln Asp Gln Thr
        35                  40

<210> SEQ ID NO 274
<211> LENGTH: 42
<212> TYPE: PRT
<213> ORGANISM: Artificial sequence
<220> FEATURE:
<223> OTHER INFORMATION: Odk2 variant

<400> SEQUENCE: 274

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala His Arg Pro
        35                  40

<210> SEQ ID NO 275

```
<211> LENGTH: 42
<212> TYPE: PRT
<213> ORGANISM: Artificial sequence
<220> FEATURE:
<223> OTHER INFORMATION: Odk2 variant

<400> SEQUENCE: 275

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gln Pro Thr His
        35                  40

<210> SEQ ID NO 276
<211> LENGTH: 42
<212> TYPE: PRT
<213> ORGANISM: Artificial sequence
<220> FEATURE:
<223> OTHER INFORMATION: Odk2 variant

<400> SEQUENCE: 276

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Glu Gln Thr
        35                  40

<210> SEQ ID NO 277
<211> LENGTH: 42
<212> TYPE: PRT
<213> ORGANISM: Artificial sequence
<220> FEATURE:
<223> OTHER INFORMATION: Odk2 variant

<400> SEQUENCE: 277

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Pro Lys Pro
        35                  40

<210> SEQ ID NO 278
<211> LENGTH: 42
<212> TYPE: PRT
<213> ORGANISM: Artificial sequence
<220> FEATURE:
<223> OTHER INFORMATION: Odk2 variant

<400> SEQUENCE: 278

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Lys Gln Gly Ala
        35                  40

<210> SEQ ID NO 279
<211> LENGTH: 42
<212> TYPE: PRT
<213> ORGANISM: Artificial sequence
```

<220> FEATURE:
<223> OTHER INFORMATION: Odk2 variant

<400> SEQUENCE: 279

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Arg Pro Ala
        35                  40

<210> SEQ ID NO 280
<211> LENGTH: 42
<212> TYPE: PRT
<213> ORGANISM: Artificial sequence
<220> FEATURE:
<223> OTHER INFORMATION: Odk2 variant

<400> SEQUENCE: 280

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Pro His Lys
        35                  40

<210> SEQ ID NO 281
<211> LENGTH: 42
<212> TYPE: PRT
<213> ORGANISM: Artificial sequence
<220> FEATURE:
<223> OTHER INFORMATION: Odk2 variant

<400> SEQUENCE: 281

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Thr Glu His
        35                  40

<210> SEQ ID NO 282
<211> LENGTH: 42
<212> TYPE: PRT
<213> ORGANISM: Artificial sequence
<220> FEATURE:
<223> OTHER INFORMATION: Odk2 variant

<400> SEQUENCE: 282

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Thr His Thr
        35                  40

<210> SEQ ID NO 283
<211> LENGTH: 42
<212> TYPE: PRT
<213> ORGANISM: Artificial sequence
<220> FEATURE:
<223> OTHER INFORMATION: Odk2 variant

<400> SEQUENCE: 283

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Ala Glu Lys
        35                  40

<210> SEQ ID NO 284
<211> LENGTH: 42
<212> TYPE: PRT
<213> ORGANISM: Artificial sequence
<220> FEATURE:
<223> OTHER INFORMATION: Odk2 variant

<400> SEQUENCE: 284

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Ala Pro Ala
        35                  40

<210> SEQ ID NO 285
<211> LENGTH: 42
<212> TYPE: PRT
<213> ORGANISM: Artificial sequence
<220> FEATURE:
<223> OTHER INFORMATION: Odk2 variant

<400> SEQUENCE: 285

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ser His Arg Pro
        35                  40

<210> SEQ ID NO 286
<211> LENGTH: 42
<212> TYPE: PRT
<213> ORGANISM: Artificial sequence
<220> FEATURE:
<223> OTHER INFORMATION: Odk2 variant

<400> SEQUENCE: 286

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ser His Arg Pro
        35                  40

<210> SEQ ID NO 287
<211> LENGTH: 42
<212> TYPE: PRT
<213> ORGANISM: Artificial sequence
<220> FEATURE:
<223> OTHER INFORMATION: Odk2 variant

<400> SEQUENCE: 287

Gly Val Pro Ile Asn Val Lys Cys Lys Ile Ser Arg Gln Cys Ile Glu

```
                 1               5                  10                 15
Pro Cys Lys Asp Ala Gly Met Arg Phe Gly Lys Cys Met Asn Gly Lys
                20                 25                 30

Cys His Cys Thr Pro Lys Pro Pro Thr Arg
             35                 40
```

<210> SEQ ID NO 288
<211> LENGTH: 42
<212> TYPE: PRT
<213> ORGANISM: Artificial sequence
<220> FEATURE:
<223> OTHER INFORMATION: Odk2 variant

<400> SEQUENCE: 288

```
Gly Val Pro Ile Asn Val Lys Cys Lys Ile Ser Arg Gln Cys Ile Glu
1               5                   10                  15
Pro Cys Lys Asp Ala Gly Met Arg Phe Gly Lys Cys Met Asn Gly Lys
                20                  25                  30
Cys His Cys Thr Pro Lys His His Thr Thr
             35                  40
```

<210> SEQ ID NO 289
<211> LENGTH: 42
<212> TYPE: PRT
<213> ORGANISM: Artificial sequence
<220> FEATURE:
<223> OTHER INFORMATION: Odk2 variant

<400> SEQUENCE: 289

```
Gly Val Pro Ile Asn Val Lys Cys Lys Ile Ser Arg Gln Cys Ile Glu
1               5                   10                  15
Pro Cys Lys Asp Ala Gly Met Arg Phe Gly Lys Cys Met Asn Gly Lys
                20                  25                  30
Cys His Cys Thr Pro Lys His Arg Pro Ala
             35                  40
```

<210> SEQ ID NO 290
<211> LENGTH: 42
<212> TYPE: PRT
<213> ORGANISM: Artificial sequence
<220> FEATURE:
<223> OTHER INFORMATION: Odk2 variant

<400> SEQUENCE: 290

```
Gly Val Pro Ile Asn Val Lys Cys Lys Ile Ser Arg Gln Cys Ile Glu
1               5                   10                  15
Pro Cys Lys Asp Ala Gly Met Arg Phe Gly Lys Cys Met Asn Gly Lys
                20                  25                  30
Cys His Cys Thr Pro Lys Lys Ala His Pro
             35                  40
```

<210> SEQ ID NO 291
<211> LENGTH: 42
<212> TYPE: PRT
<213> ORGANISM: Artificial sequence
<220> FEATURE:
<223> OTHER INFORMATION: Odk2 variant

<400> SEQUENCE: 291

```
Gly Val Pro Ile Asn Val Lys Cys Lys Ile Ser Arg Gln Cys Ile Glu
1               5                   10                  15
Pro Cys Lys Asp Ala Gly Met Arg Phe Gly Lys Cys Met Asn Gly Lys
```

```
                    20                  25                  30

Cys His Cys Thr Pro Lys Gln Thr Thr Gln
        35                  40

<210> SEQ ID NO 292
<211> LENGTH: 42
<212> TYPE: PRT
<213> ORGANISM: Artificial sequence
<220> FEATURE:
<223> OTHER INFORMATION: Odk2 variant

<400> SEQUENCE: 292

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Thr Pro Thr
        35                  40

<210> SEQ ID NO 293
<211> LENGTH: 42
<212> TYPE: PRT
<213> ORGANISM: Artificial sequence
<220> FEATURE:
<223> OTHER INFORMATION: Odk2 variant

<400> SEQUENCE: 293

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Gln Ala Pro
        35                  40

<210> SEQ ID NO 294
<211> LENGTH: 42
<212> TYPE: PRT
<213> ORGANISM: Artificial sequence
<220> FEATURE:
<223> OTHER INFORMATION: Odk2 variant

<400> SEQUENCE: 294

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Lys Pro His
        35                  40

<210> SEQ ID NO 295
<211> LENGTH: 42
<212> TYPE: PRT
<213> ORGANISM: Artificial sequence
<220> FEATURE:
<223> OTHER INFORMATION: Odk2 variant

<400> SEQUENCE: 295

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Thr Pro Pro
```

<210> SEQ ID NO 296
<211> LENGTH: 42
<212> TYPE: PRT
<213> ORGANISM: Artificial sequence
<220> FEATURE:
<223> OTHER INFORMATION: Odk2 variant

<400> SEQUENCE: 296

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Lys Pro Pro
        35                  40

<210> SEQ ID NO 297
<211> LENGTH: 42
<212> TYPE: PRT
<213> ORGANISM: Artificial sequence
<220> FEATURE:
<223> OTHER INFORMATION: Odk2 variant

<400> SEQUENCE: 297

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Arg Pro Thr
        35                  40

<210> SEQ ID NO 298
<211> LENGTH: 42
<212> TYPE: PRT
<213> ORGANISM: Artificial sequence
<220> FEATURE:
<223> OTHER INFORMATION: Odk2 variant

<400> SEQUENCE: 298

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Lys Gln Thr Ala
        35                  40

<210> SEQ ID NO 299
<211> LENGTH: 42
<212> TYPE: PRT
<213> ORGANISM: Artificial sequence
<220> FEATURE:
<223> OTHER INFORMATION: Odk2 variant

<400> SEQUENCE: 299

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro His Thr Pro
        35                  40

```
<210> SEQ ID NO 300
<211> LENGTH: 42
<212> TYPE: PRT
<213> ORGANISM: Artificial sequence
<220> FEATURE:
<223> OTHER INFORMATION: Odk2 variant

<400> SEQUENCE: 300

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Thr Pro Pro
        35                  40

<210> SEQ ID NO 301
<211> LENGTH: 42
<212> TYPE: PRT
<213> ORGANISM: Artificial sequence
<220> FEATURE:
<223> OTHER INFORMATION: Odk2 variant

<400> SEQUENCE: 301

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Ala Lys Pro
        35                  40

<210> SEQ ID NO 302
<211> LENGTH: 42
<212> TYPE: PRT
<213> ORGANISM: Artificial sequence
<220> FEATURE:
<223> OTHER INFORMATION: Odk2 variant

<400> SEQUENCE: 302

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Arg Arg Pro
        35                  40

<210> SEQ ID NO 303
<211> LENGTH: 42
<212> TYPE: PRT
<213> ORGANISM: Artificial sequence
<220> FEATURE:
<223> OTHER INFORMATION: Odk2 variant

<400> SEQUENCE: 303

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Thr Thr Pro
        35                  40

<210> SEQ ID NO 304
<211> LENGTH: 42
<212> TYPE: PRT
```

<213> ORGANISM: Artificial sequence
<220> FEATURE:
<223> OTHER INFORMATION: Odk2 variant

<400> SEQUENCE: 304

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Gln His Ala
        35                  40

<210> SEQ ID NO 305
<211> LENGTH: 42
<212> TYPE: PRT
<213> ORGANISM: Artificial sequence
<220> FEATURE:
<223> OTHER INFORMATION: Odk2 variant

<400> SEQUENCE: 305

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Thr Arg Pro
        35                  40

<210> SEQ ID NO 306
<211> LENGTH: 42
<212> TYPE: PRT
<213> ORGANISM: Artificial sequence
<220> FEATURE:
<223> OTHER INFORMATION: Odk2 variant

<400> SEQUENCE: 306

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Ala Pro His
        35                  40

<210> SEQ ID NO 307
<211> LENGTH: 42
<212> TYPE: PRT
<213> ORGANISM: Artificial sequence
<220> FEATURE:
<223> OTHER INFORMATION: Odk2 variant

<400> SEQUENCE: 307

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Asp Lys Pro
        35                  40

<210> SEQ ID NO 308
<211> LENGTH: 42
<212> TYPE: PRT
<213> ORGANISM: Artificial sequence
<220> FEATURE:
<223> OTHER INFORMATION: Odk2 variant

<400> SEQUENCE: 308

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro His His Gln
        35                  40

<210> SEQ ID NO 309
<211> LENGTH: 42
<212> TYPE: PRT
<213> ORGANISM: Artificial sequence
<220> FEATURE:
<223> OTHER INFORMATION: Odk2 variant

<400> SEQUENCE: 309

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gly Arg Arg Thr
        35                  40

<210> SEQ ID NO 310
<211> LENGTH: 42
<212> TYPE: PRT
<213> ORGANISM: Artificial sequence
<220> FEATURE:
<223> OTHER INFORMATION: Odk2 variant

<400> SEQUENCE: 310

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Pro Asp Ala
        35                  40

<210> SEQ ID NO 311
<211> LENGTH: 42
<212> TYPE: PRT
<213> ORGANISM: Artificial sequence
<220> FEATURE:
<223> OTHER INFORMATION: Odk2 variant

<400> SEQUENCE: 311

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asn His Arg Pro
        35                  40

<210> SEQ ID NO 312
<211> LENGTH: 42
<212> TYPE: PRT
<213> ORGANISM: Artificial sequence
<220> FEATURE:
<223> OTHER INFORMATION: Odk2 variant

<400> SEQUENCE: 312

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asn His Gln Gly
        35                  40

<210> SEQ ID NO 313
<211> LENGTH: 42
<212> TYPE: PRT
<213> ORGANISM: Artificial sequence
<220> FEATURE:
<223> OTHER INFORMATION: Odk2 variant

<400> SEQUENCE: 313

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Ala Pro Pro
        35                  40

<210> SEQ ID NO 314
<211> LENGTH: 42
<212> TYPE: PRT
<213> ORGANISM: Artificial sequence
<220> FEATURE:
<223> OTHER INFORMATION: Odk2 variant

<400> SEQUENCE: 314

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg His Pro His
        35                  40

<210> SEQ ID NO 315
<211> LENGTH: 42
<212> TYPE: PRT
<213> ORGANISM: Artificial sequence
<220> FEATURE:
<223> OTHER INFORMATION: Odk2 variant

<400> SEQUENCE: 315

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Ser Arg Pro
        35                  40

<210> SEQ ID NO 316
<211> LENGTH: 42
<212> TYPE: PRT
<213> ORGANISM: Artificial sequence
<220> FEATURE:
<223> OTHER INFORMATION: Odk2 variant

<400> SEQUENCE: 316

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Gln His Gln
            35                  40

<210> SEQ ID NO 317
<211> LENGTH: 42
<212> TYPE: PRT
<213> ORGANISM: Artificial sequence
<220> FEATURE:
<223> OTHER INFORMATION: Odk2 variant

<400> SEQUENCE: 317

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Thr Gln His
            35                  40

<210> SEQ ID NO 318
<211> LENGTH: 42
<212> TYPE: PRT
<213> ORGANISM: Artificial sequence
<220> FEATURE:
<223> OTHER INFORMATION: Odk2 variant

<400> SEQUENCE: 318

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Thr Lys Pro
            35                  40

<210> SEQ ID NO 319
<211> LENGTH: 42
<212> TYPE: PRT
<213> ORGANISM: Artificial sequence
<220> FEATURE:
<223> OTHER INFORMATION: Odk2 variant

<400> SEQUENCE: 319

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Lys Lys Pro
            35                  40

<210> SEQ ID NO 320
<211> LENGTH: 42
<212> TYPE: PRT
<213> ORGANISM: Artificial sequence
<220> FEATURE:
<223> OTHER INFORMATION: Odk2 variant

<400> SEQUENCE: 320

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Asn Arg Pro
        35                  40

<210> SEQ ID NO 321
<211> LENGTH: 42
<212> TYPE: PRT
<213> ORGANISM: Artificial sequence
<220> FEATURE:
<223> OTHER INFORMATION: Odk2 variant

<400> SEQUENCE: 321

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
                20                  25                  30

Cys His Cys Thr Pro Lys Pro Glu Lys Pro
        35                  40

<210> SEQ ID NO 322
<211> LENGTH: 42
<212> TYPE: PRT
<213> ORGANISM: Artificial sequence
<220> FEATURE:
<223> OTHER INFORMATION: Odk2 variant

<400> SEQUENCE: 322

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
                20                  25                  30

Cys His Cys Thr Pro Lys Arg Ala Gln Thr
        35                  40

<210> SEQ ID NO 323
<211> LENGTH: 42
<212> TYPE: PRT
<213> ORGANISM: Artificial sequence
<220> FEATURE:
<223> OTHER INFORMATION: Odk2 variant

<400> SEQUENCE: 323

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
                20                  25                  30

Cys His Cys Thr Pro Lys Pro Ala Ala Thr
        35                  40

<210> SEQ ID NO 324
<211> LENGTH: 42
<212> TYPE: PRT
<213> ORGANISM: Artificial sequence
<220> FEATURE:
<223> OTHER INFORMATION: Odk2 variant

<400> SEQUENCE: 324

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
                20                  25                  30

Cys His Cys Thr Pro Lys Arg Thr Glu Gln
        35                  40

<210> SEQ ID NO 325
<211> LENGTH: 42
<212> TYPE: PRT
<213> ORGANISM: Artificial sequence
<220> FEATURE:
<223> OTHER INFORMATION: Odk2 variant

<400> SEQUENCE: 325

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Pro Ala Lys
        35                  40
```

<210> SEQ ID NO 326
<211> LENGTH: 42
<212> TYPE: PRT
<213> ORGANISM: Artificial sequence
<220> FEATURE:
<223> OTHER INFORMATION: Odk2 variant

<400> SEQUENCE: 326

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Glu Pro Arg Pro
        35                  40
```

<210> SEQ ID NO 327
<211> LENGTH: 42
<212> TYPE: PRT
<213> ORGANISM: Artificial sequence
<220> FEATURE:
<223> OTHER INFORMATION: Odk2 variant

<400> SEQUENCE: 327

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Ala Thr His
        35                  40
```

<210> SEQ ID NO 328
<211> LENGTH: 42
<212> TYPE: PRT
<213> ORGANISM: Artificial sequence
<220> FEATURE:
<223> OTHER INFORMATION: Odk2 variant

<400> SEQUENCE: 328

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Arg Pro Asp
        35                  40
```

<210> SEQ ID NO 329
<211> LENGTH: 42

<212> TYPE: PRT
<213> ORGANISM: Artificial sequence
<220> FEATURE:
<223> OTHER INFORMATION: Odk2 variant

<400> SEQUENCE: 329

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala His Pro His
        35                  40

<210> SEQ ID NO 330
<211> LENGTH: 42
<212> TYPE: PRT
<213> ORGANISM: Artificial sequence
<220> FEATURE:
<223> OTHER INFORMATION: Odk2 variant

<400> SEQUENCE: 330

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Ala Pro Ser
        35                  40

<210> SEQ ID NO 331
<211> LENGTH: 42
<212> TYPE: PRT
<213> ORGANISM: Artificial sequence
<220> FEATURE:
<223> OTHER INFORMATION: Odk2 variant

<400> SEQUENCE: 331

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Pro Arg Pro
        35                  40

<210> SEQ ID NO 332
<211> LENGTH: 42
<212> TYPE: PRT
<213> ORGANISM: Artificial sequence
<220> FEATURE:
<223> OTHER INFORMATION: Odk2 variant

<400> SEQUENCE: 332

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Asp Lys Pro
        35                  40

<210> SEQ ID NO 333
<211> LENGTH: 42
<212> TYPE: PRT
<213> ORGANISM: Artificial sequence
<220> FEATURE:

<223> OTHER INFORMATION: Odk2 variant

<400> SEQUENCE: 333

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Pro His Pro
        35                  40

<210> SEQ ID NO 334
<211> LENGTH: 42
<212> TYPE: PRT
<213> ORGANISM: Artificial sequence
<220> FEATURE:
<223> OTHER INFORMATION: Odk2 variant

<400> SEQUENCE: 334

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Thr Arg Pro
        35                  40

<210> SEQ ID NO 335
<211> LENGTH: 42
<212> TYPE: PRT
<213> ORGANISM: Artificial sequence
<220> FEATURE:
<223> OTHER INFORMATION: Odk2 variant

<400> SEQUENCE: 335

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Gln Gln His
        35                  40

<210> SEQ ID NO 336
<211> LENGTH: 42
<212> TYPE: PRT
<213> ORGANISM: Artificial sequence
<220> FEATURE:
<223> OTHER INFORMATION: Odk2 variant

<400> SEQUENCE: 336

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Arg Arg Pro
        35                  40

<210> SEQ ID NO 337
<211> LENGTH: 42
<212> TYPE: PRT
<213> ORGANISM: Artificial sequence
<220> FEATURE:
<223> OTHER INFORMATION: Odk2 variant

<400> SEQUENCE: 337

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Arg Arg Pro
        35                  40
```

<210> SEQ ID NO 338
<211> LENGTH: 42
<212> TYPE: PRT
<213> ORGANISM: Artificial sequence
<220> FEATURE:
<223> OTHER INFORMATION: Odk2 variant

<400> SEQUENCE: 338

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Gln Pro Pro
        35                  40
```

<210> SEQ ID NO 339
<211> LENGTH: 42
<212> TYPE: PRT
<213> ORGANISM: Artificial sequence
<220> FEATURE:
<223> OTHER INFORMATION: Odk2 variant

<400> SEQUENCE: 339

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Thr Pro Pro
        35                  40
```

<210> SEQ ID NO 340
<211> LENGTH: 42
<212> TYPE: PRT
<213> ORGANISM: Artificial sequence
<220> FEATURE:
<223> OTHER INFORMATION: Odk2 variant

<400> SEQUENCE: 340

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Glu Lys Pro Thr
        35                  40
```

<210> SEQ ID NO 341
<211> LENGTH: 42
<212> TYPE: PRT
<213> ORGANISM: Artificial sequence
<220> FEATURE:
<223> OTHER INFORMATION: Odk2 variant

<400> SEQUENCE: 341

```
Gly Val Pro Ile Asn Val Lys Cys Lys Ile Ser Arg Gln Cys Ile Glu
1               5                   10                  15
```

Pro Cys Lys Asp Ala Gly Met Arg Phe Gly Lys Cys Met Asn Gly Lys
            20                  25                  30

Cys His Cys Thr Pro Lys Gly His Thr Ala
        35                  40

<210> SEQ ID NO 342
<211> LENGTH: 42
<212> TYPE: PRT
<213> ORGANISM: Artificial sequence
<220> FEATURE:
<223> OTHER INFORMATION: Odk2 variant

<400> SEQUENCE: 342

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Thr Lys Pro
        35                  40

<210> SEQ ID NO 343
<211> LENGTH: 42
<212> TYPE: PRT
<213> ORGANISM: Artificial sequence
<220> FEATURE:
<223> OTHER INFORMATION: Odk2 variant

<400> SEQUENCE: 343

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Thr Thr Pro
        35                  40

<210> SEQ ID NO 344
<211> LENGTH: 42
<212> TYPE: PRT
<213> ORGANISM: Artificial sequence
<220> FEATURE:
<223> OTHER INFORMATION: Odk2 variant

<400> SEQUENCE: 344

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Gly His Thr
        35                  40

<210> SEQ ID NO 345
<211> LENGTH: 42
<212> TYPE: PRT
<213> ORGANISM: Artificial sequence
<220> FEATURE:
<223> OTHER INFORMATION: Odk2 variant

<400> SEQUENCE: 345

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gly Gly Pro Gln
        35                  40

<210> SEQ ID NO 346
<211> LENGTH: 42
<212> TYPE: PRT
<213> ORGANISM: Artificial sequence
<220> FEATURE:
<223> OTHER INFORMATION: Odk2 variant

<400> SEQUENCE: 346

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Arg Arg Gln
        35                  40

<210> SEQ ID NO 347
<211> LENGTH: 42
<212> TYPE: PRT
<213> ORGANISM: Artificial sequence
<220> FEATURE:
<223> OTHER INFORMATION: Odk2 variant

<400> SEQUENCE: 347

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Asn Ala Pro
        35                  40

<210> SEQ ID NO 348
<211> LENGTH: 42
<212> TYPE: PRT
<213> ORGANISM: Artificial sequence
<220> FEATURE:
<223> OTHER INFORMATION: Odk2 variant

<400> SEQUENCE: 348

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Gln Pro Gln
        35                  40

<210> SEQ ID NO 349
<211> LENGTH: 42
<212> TYPE: PRT
<213> ORGANISM: Artificial sequence
<220> FEATURE:
<223> OTHER INFORMATION: Odk2 variant

<400> SEQUENCE: 349

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asn Arg Arg Pro
        35                  40

<210> SEQ ID NO 350
<211> LENGTH: 42
<212> TYPE: PRT
<213> ORGANISM: Artificial sequence
<220> FEATURE:
<223> OTHER INFORMATION: Odk2 variant

<400> SEQUENCE: 350

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gln Ala Ala Pro
        35                  40

<210> SEQ ID NO 351
<211> LENGTH: 42
<212> TYPE: PRT
<213> ORGANISM: Artificial sequence
<220> FEATURE:
<223> OTHER INFORMATION: Odk2 variant

<400> SEQUENCE: 351

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gln Pro Gln Asp
        35                  40

<210> SEQ ID NO 352
<211> LENGTH: 42
<212> TYPE: PRT
<213> ORGANISM: Artificial sequence
<220> FEATURE:
<223> OTHER INFORMATION: Odk2 variant

<400> SEQUENCE: 352

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Thr Arg Pro
        35                  40

<210> SEQ ID NO 353
<211> LENGTH: 42
<212> TYPE: PRT
<213> ORGANISM: Artificial sequence
<220> FEATURE:
<223> OTHER INFORMATION: Odk2 variant

<400> SEQUENCE: 353

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asn Arg Pro Pro
        35                  40

<210> SEQ ID NO 354

<211> LENGTH: 42
<212> TYPE: PRT
<213> ORGANISM: Artificial sequence
<220> FEATURE:
<223> OTHER INFORMATION: Odk2 variant

<400> SEQUENCE: 354

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Arg Pro
        35                  40

<210> SEQ ID NO 355
<211> LENGTH: 42
<212> TYPE: PRT
<213> ORGANISM: Artificial sequence
<220> FEATURE:
<223> OTHER INFORMATION: Odk2 variant

<400> SEQUENCE: 355

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala His Arg His
        35                  40

<210> SEQ ID NO 356
<211> LENGTH: 42
<212> TYPE: PRT
<213> ORGANISM: Artificial sequence
<220> FEATURE:
<223> OTHER INFORMATION: Odk2 variant

<400> SEQUENCE: 356

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Gln Arg Pro
        35                  40

<210> SEQ ID NO 357
<211> LENGTH: 42
<212> TYPE: PRT
<213> ORGANISM: Artificial sequence
<220> FEATURE:
<223> OTHER INFORMATION: Odk2 variant

<400> SEQUENCE: 357

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Ser Asp Thr
        35                  40

<210> SEQ ID NO 358
<211> LENGTH: 42
<212> TYPE: PRT
<213> ORGANISM: Artificial sequence
<220> FEATURE:
<223> OTHER INFORMATION: Odk2 variant

<400> SEQUENCE: 358

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Arg Pro Gly
        35                  40

<210> SEQ ID NO 359
<211> LENGTH: 42
<212> TYPE: PRT
<213> ORGANISM: Artificial sequence
<220> FEATURE:
<223> OTHER INFORMATION: Odk2 variant

<400> SEQUENCE: 359

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gln Ser Lys Ala
        35                  40

<210> SEQ ID NO 360
<211> LENGTH: 42
<212> TYPE: PRT
<213> ORGANISM: Artificial sequence
<220> FEATURE:
<223> OTHER INFORMATION: Odk2 variant

<400> SEQUENCE: 360

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Gly Pro Arg
        35                  40

<210> SEQ ID NO 361
<211> LENGTH: 42
<212> TYPE: PRT
<213> ORGANISM: Artificial sequence
<220> FEATURE:
<223> OTHER INFORMATION: Odk2 variant

<400> SEQUENCE: 361

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Ser Arg Thr
        35                  40

<210> SEQ ID NO 362
<211> LENGTH: 42
<212> TYPE: PRT
<213> ORGANISM: Artificial sequence
<220> FEATURE:
<223> OTHER INFORMATION: Odk2 variant

<400> SEQUENCE: 362

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg His Lys Arg
        35                  40

<210> SEQ ID NO 363
<211> LENGTH: 42
<212> TYPE: PRT
<213> ORGANISM: Artificial sequence
<220> FEATURE:
<223> OTHER INFORMATION: Odk2 variant

<400> SEQUENCE: 363

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asn Ala Ala Lys
        35                  40

<210> SEQ ID NO 364
<211> LENGTH: 42
<212> TYPE: PRT
<213> ORGANISM: Artificial sequence
<220> FEATURE:
<223> OTHER INFORMATION: Odk2 variant

<400> SEQUENCE: 364

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Pro His Thr
        35                  40

<210> SEQ ID NO 365
<211> LENGTH: 42
<212> TYPE: PRT
<213> ORGANISM: Artificial sequence
<220> FEATURE:
<223> OTHER INFORMATION: Odk2 variant

<400> SEQUENCE: 365

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gly Gly Lys Arg
        35                  40

<210> SEQ ID NO 366
<211> LENGTH: 42
<212> TYPE: PRT
<213> ORGANISM: Artificial sequence
<220> FEATURE:
<223> OTHER INFORMATION: Odk2 variant

<400> SEQUENCE: 366

Gly Val Pro Ile Asn Val Lys Cys Lys Ile Ser Arg Gln Cys Ile Glu

```
1               5                   10                  15
Pro Cys Lys Asp Ala Gly Met Arg Phe Gly Lys Cys Met Asn Gly Lys
            20                  25                  30

Cys His Cys Thr Pro Lys Arg Arg Glu Pro
            35                  40
```

<210> SEQ ID NO 367
<211> LENGTH: 42
<212> TYPE: PRT
<213> ORGANISM: Artificial sequence
<220> FEATURE:
<223> OTHER INFORMATION: Odk2 variant

<400> SEQUENCE: 367

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Thr Arg Thr
            35                  40
```

<210> SEQ ID NO 368
<211> LENGTH: 42
<212> TYPE: PRT
<213> ORGANISM: Artificial sequence
<220> FEATURE:
<223> OTHER INFORMATION: Odk2 variant

<400> SEQUENCE: 368

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asn His Arg Thr
            35                  40
```

<210> SEQ ID NO 369
<211> LENGTH: 42
<212> TYPE: PRT
<213> ORGANISM: Artificial sequence
<220> FEATURE:
<223> OTHER INFORMATION: Odk2 variant

<400> SEQUENCE: 369

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Asn Arg Thr
            35                  40
```

<210> SEQ ID NO 370
<211> LENGTH: 42
<212> TYPE: PRT
<213> ORGANISM: Artificial sequence
<220> FEATURE:
<223> OTHER INFORMATION: Odk2 variant

<400> SEQUENCE: 370

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
```

Cys His Cys Thr Pro Lys Pro Lys Thr Ala
        35                  40

<210> SEQ ID NO 371
<211> LENGTH: 42
<212> TYPE: PRT
<213> ORGANISM: Artificial sequence
<220> FEATURE:
<223> OTHER INFORMATION: Odk2 variant

<400> SEQUENCE: 371

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Arg Arg Pro
        35                  40

<210> SEQ ID NO 372
<211> LENGTH: 42
<212> TYPE: PRT
<213> ORGANISM: Artificial sequence
<220> FEATURE:
<223> OTHER INFORMATION: Odk2 variant

<400> SEQUENCE: 372

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg His Asn Thr
        35                  40

<210> SEQ ID NO 373
<211> LENGTH: 42
<212> TYPE: PRT
<213> ORGANISM: Artificial sequence
<220> FEATURE:
<223> OTHER INFORMATION: Odk2 variant

<400> SEQUENCE: 373

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Asp Ala Arg
        35                  40

<210> SEQ ID NO 374
<211> LENGTH: 42
<212> TYPE: PRT
<213> ORGANISM: Artificial sequence
<220> FEATURE:
<223> OTHER INFORMATION: Odk2 variant

<400> SEQUENCE: 374

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Arg Gln Gln

<210> SEQ ID NO 375
<211> LENGTH: 42
<212> TYPE: PRT
<213> ORGANISM: Artificial sequence
<220> FEATURE:
<223> OTHER INFORMATION: Odk2 variant

<400> SEQUENCE: 375

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asn Gln Arg Thr
        35                  40

<210> SEQ ID NO 376
<211> LENGTH: 42
<212> TYPE: PRT
<213> ORGANISM: Artificial sequence
<220> FEATURE:
<223> OTHER INFORMATION: Odk2 variant

<400> SEQUENCE: 376

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Pro Arg His
        35                  40

<210> SEQ ID NO 377
<211> LENGTH: 42
<212> TYPE: PRT
<213> ORGANISM: Artificial sequence
<220> FEATURE:
<223> OTHER INFORMATION: Odk2 variant

<400> SEQUENCE: 377

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Asn Glu Thr
        35                  40

<210> SEQ ID NO 378
<211> LENGTH: 42
<212> TYPE: PRT
<213> ORGANISM: Artificial sequence
<220> FEATURE:
<223> OTHER INFORMATION: Odk2 variant

<400> SEQUENCE: 378

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Arg Asn Ala
        35                  40

<210> SEQ ID NO 379
<211> LENGTH: 42
<212> TYPE: PRT
<213> ORGANISM: Artificial sequence
<220> FEATURE:
<223> OTHER INFORMATION: Odk2 variant

<400> SEQUENCE: 379

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Thr Arg Thr
        35                  40

<210> SEQ ID NO 380
<211> LENGTH: 42
<212> TYPE: PRT
<213> ORGANISM: Artificial sequence
<220> FEATURE:
<223> OTHER INFORMATION: Odk2 variant

<400> SEQUENCE: 380

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Arg Arg Asn
        35                  40

<210> SEQ ID NO 381
<211> LENGTH: 42
<212> TYPE: PRT
<213> ORGANISM: Artificial sequence
<220> FEATURE:
<223> OTHER INFORMATION: Odk2 variant

<400> SEQUENCE: 381

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Gly Arg Lys
        35                  40

<210> SEQ ID NO 382
<211> LENGTH: 42
<212> TYPE: PRT
<213> ORGANISM: Artificial sequence
<220> FEATURE:
<223> OTHER INFORMATION: Odk2 variant

<400> SEQUENCE: 382

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Ser Asp Asn
        35                  40

<210> SEQ ID NO 383
<211> LENGTH: 42
<212> TYPE: PRT

<213> ORGANISM: Artificial sequence
<220> FEATURE:
<223> OTHER INFORMATION: Odk2 variant

<400> SEQUENCE: 383

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Glu Arg Thr
        35                  40

<210> SEQ ID NO 384
<211> LENGTH: 42
<212> TYPE: PRT
<213> ORGANISM: Artificial sequence
<220> FEATURE:
<223> OTHER INFORMATION: Odk2 variant

<400> SEQUENCE: 384

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Pro His Arg
        35                  40

<210> SEQ ID NO 385
<211> LENGTH: 42
<212> TYPE: PRT
<213> ORGANISM: Artificial sequence
<220> FEATURE:
<223> OTHER INFORMATION: Odk2 variant

<400> SEQUENCE: 385

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Arg Thr Ala
        35                  40

<210> SEQ ID NO 386
<211> LENGTH: 42
<212> TYPE: PRT
<213> ORGANISM: Artificial sequence
<220> FEATURE:
<223> OTHER INFORMATION: Odk2 variant

<400> SEQUENCE: 386

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asn Thr Arg Thr
        35                  40

<210> SEQ ID NO 387
<211> LENGTH: 42
<212> TYPE: PRT
<213> ORGANISM: Artificial sequence
<220> FEATURE:
<223> OTHER INFORMATION: Odk2 variant

<400> SEQUENCE: 387

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Thr Thr Arg
        35                  40

<210> SEQ ID NO 388
<211> LENGTH: 42
<212> TYPE: PRT
<213> ORGANISM: Artificial sequence
<220> FEATURE:
<223> OTHER INFORMATION: Odk2 variant

<400> SEQUENCE: 388

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gln Arg Asn Gly
        35                  40

<210> SEQ ID NO 389
<211> LENGTH: 42
<212> TYPE: PRT
<213> ORGANISM: Artificial sequence
<220> FEATURE:
<223> OTHER INFORMATION: Odk2 variant

<400> SEQUENCE: 389

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala His Arg Asn
        35                  40

<210> SEQ ID NO 390
<211> LENGTH: 42
<212> TYPE: PRT
<213> ORGANISM: Artificial sequence
<220> FEATURE:
<223> OTHER INFORMATION: Odk2 variant

<400> SEQUENCE: 390

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Arg Ser Ala
        35                  40

<210> SEQ ID NO 391
<211> LENGTH: 42
<212> TYPE: PRT
<213> ORGANISM: Artificial sequence
<220> FEATURE:
<223> OTHER INFORMATION: Odk2 variant

<400> SEQUENCE: 391

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gln Arg Gln Ser
        35                  40

<210> SEQ ID NO 392
<211> LENGTH: 42
<212> TYPE: PRT
<213> ORGANISM: Artificial sequence
<220> FEATURE:
<223> OTHER INFORMATION: Odk2 variant

<400> SEQUENCE: 392

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gln Arg Lys
        35                  40

<210> SEQ ID NO 393
<211> LENGTH: 42
<212> TYPE: PRT
<213> ORGANISM: Artificial sequence
<220> FEATURE:
<223> OTHER INFORMATION: Odk2 variant

<400> SEQUENCE: 393

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Arg Ala Lys
        35                  40

<210> SEQ ID NO 394
<211> LENGTH: 42
<212> TYPE: PRT
<213> ORGANISM: Artificial sequence
<220> FEATURE:
<223> OTHER INFORMATION: Odk2 variant

<400> SEQUENCE: 394

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Thr Arg Gln
        35                  40

<210> SEQ ID NO 395
<211> LENGTH: 42
<212> TYPE: PRT
<213> ORGANISM: Artificial sequence
<220> FEATURE:
<223> OTHER INFORMATION: Odk2 variant

<400> SEQUENCE: 395

Gly Val Pro Ile Asn Val Lys Cys Lys Ile Ser Arg Gln Cys Ile Glu
1               5                   10                  15

```
Pro Cys Lys Asp Ala Gly Met Arg Phe Gly Lys Cys Met Asn Gly Lys
            20                  25                  30

Cys His Cys Thr Pro Lys Ala Lys Arg Asp
            35                  40
```

<210> SEQ ID NO 396
<211> LENGTH: 42
<212> TYPE: PRT
<213> ORGANISM: Artificial sequence
<220> FEATURE:
<223> OTHER INFORMATION: Odk2 variant

<400> SEQUENCE: 396

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asp Asp Gly Ala
            35                  40
```

<210> SEQ ID NO 397
<211> LENGTH: 42
<212> TYPE: PRT
<213> ORGANISM: Artificial sequence
<220> FEATURE:
<223> OTHER INFORMATION: Odk2 variant

<400> SEQUENCE: 397

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Asp Lys Thr
            35                  40
```

<210> SEQ ID NO 398
<211> LENGTH: 42
<212> TYPE: PRT
<213> ORGANISM: Artificial sequence
<220> FEATURE:
<223> OTHER INFORMATION: Odk2 variant

<400> SEQUENCE: 398

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Arg Arg Lys
            35                  40
```

<210> SEQ ID NO 399
<211> LENGTH: 42
<212> TYPE: PRT
<213> ORGANISM: Artificial sequence
<220> FEATURE:
<223> OTHER INFORMATION: Odk2 variant

<400> SEQUENCE: 399

```
Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30
```

Cys His Cys Thr Pro Lys Arg Gln Thr Arg
        35                  40

<210> SEQ ID NO 400
<211> LENGTH: 42
<212> TYPE: PRT
<213> ORGANISM: Artificial sequence
<220> FEATURE:
<223> OTHER INFORMATION: Odk2 variant

<400> SEQUENCE: 400

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Asn Arg Asp
        35                  40

<210> SEQ ID NO 401
<211> LENGTH: 42
<212> TYPE: PRT
<213> ORGANISM: Artificial sequence
<220> FEATURE:
<223> OTHER INFORMATION: Odk2 variant

<400> SEQUENCE: 401

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Arg His Lys
        35                  40

<210> SEQ ID NO 402
<211> LENGTH: 42
<212> TYPE: PRT
<213> ORGANISM: Artificial sequence
<220> FEATURE:
<223> OTHER INFORMATION: Odk2 variant

<400> SEQUENCE: 402

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys His Arg Asn Arg
        35                  40

<210> SEQ ID NO 403
<211> LENGTH: 42
<212> TYPE: PRT
<213> ORGANISM: Artificial sequence
<220> FEATURE:
<223> OTHER INFORMATION: Odk2 variant

<400> SEQUENCE: 403

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Arg Ala Lys Arg
        35                  40

<210> SEQ ID NO 404
<211> LENGTH: 42
<212> TYPE: PRT
<213> ORGANISM: Artificial sequence
<220> FEATURE:
<223> OTHER INFORMATION: Odk2 variant

<400> SEQUENCE: 404

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Gln Arg Thr Arg
        35                  40

<210> SEQ ID NO 405
<211> LENGTH: 42
<212> TYPE: PRT
<213> ORGANISM: Artificial sequence
<220> FEATURE:
<223> OTHER INFORMATION: Odk2 variant

<400> SEQUENCE: 405

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Thr Arg His
        35                  40

<210> SEQ ID NO 406
<211> LENGTH: 42
<212> TYPE: PRT
<213> ORGANISM: Artificial sequence
<220> FEATURE:
<223> OTHER INFORMATION: Odk2 variant

<400> SEQUENCE: 406

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Arg Arg Ser
        35                  40

<210> SEQ ID NO 407
<211> LENGTH: 42
<212> TYPE: PRT
<213> ORGANISM: Artificial sequence
<220> FEATURE:
<223> OTHER INFORMATION: Odk2 variant

<400> SEQUENCE: 407

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Lys Thr Arg
        35                  40

<210> SEQ ID NO 408
<211> LENGTH: 42

```
<212> TYPE: PRT
<213> ORGANISM: Artificial sequence
<220> FEATURE:
<223> OTHER INFORMATION: Odk2 variant

<400> SEQUENCE: 408

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asn Ala Arg Gln
        35                  40

<210> SEQ ID NO 409
<211> LENGTH: 42
<212> TYPE: PRT
<213> ORGANISM: Artificial sequence
<220> FEATURE:
<223> OTHER INFORMATION: Odk2 variant

<400> SEQUENCE: 409

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Asn Arg Gln Arg
        35                  40

<210> SEQ ID NO 410
<211> LENGTH: 42
<212> TYPE: PRT
<213> ORGANISM: Artificial sequence
<220> FEATURE:
<223> OTHER INFORMATION: Odk2 variant

<400> SEQUENCE: 410

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Thr Asn Ala
        35                  40

<210> SEQ ID NO 411
<211> LENGTH: 42
<212> TYPE: PRT
<213> ORGANISM: Artificial sequence
<220> FEATURE:
<223> OTHER INFORMATION: Odk2 variant

<400> SEQUENCE: 411

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Arg Thr Asp
        35                  40

<210> SEQ ID NO 412
<211> LENGTH: 42
<212> TYPE: PRT
<213> ORGANISM: Artificial sequence
<220> FEATURE:
```

<223> OTHER INFORMATION: Odk2 variant

<400> SEQUENCE: 412

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Ala Asp Thr Arg
        35                  40

<210> SEQ ID NO 413
<211> LENGTH: 42
<212> TYPE: PRT
<213> ORGANISM: Artificial sequence
<220> FEATURE:
<223> OTHER INFORMATION: Odk2 variant

<400> SEQUENCE: 413

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Thr Ser Arg Gln
        35                  40

<210> SEQ ID NO 414
<211> LENGTH: 42
<212> TYPE: PRT
<213> ORGANISM: Artificial sequence
<220> FEATURE:
<223> OTHER INFORMATION: Odk2 variant

<400> SEQUENCE: 414

Gly Val Pro Ile Asn Val Lys Cys Lys Ile Ser Arg Gln Cys Ile Glu
1               5                   10                  15

Pro Cys Lys Asp Ala Gly Met Arg Phe Gly Lys Cys Met Asn Gly Lys
            20                  25                  30

Cys His Cys Thr Pro Lys Pro Arg Asn Thr
        35                  40

<210> SEQ ID NO 415
<211> LENGTH: 42
<212> TYPE: PRT
<213> ORGANISM: Artificial sequence
<220> FEATURE:
<223> OTHER INFORMATION: Odk2 variant

<400> SEQUENCE: 415

Gly Val Pro Thr Asp Val Lys Cys Arg Ile Ser Arg Gln Cys Glu Lys
1               5                   10                  15

Pro Cys Lys Asp Ala Gly Met Arg Phe Gly Lys Cys Met Asn Gly Lys
            20                  25                  30

Cys His Cys Thr Pro Lys Ala His Arg His
        35                  40

<210> SEQ ID NO 416
<211> LENGTH: 42
<212> TYPE: PRT
<213> ORGANISM: Artificial sequence
<220> FEATURE:
<223> OTHER INFORMATION: Odk2 variant

<400> SEQUENCE: 416

Gly Val Pro Thr Asp Val Lys Cys Arg Ile Ser Arg Gln Cys Glu Lys
1               5                   10                  15

Pro Cys Lys Asp Ala Gly Met Arg Phe Gly Lys Cys Met Asn Gly Lys
            20                  25                  30

Cys His Cys Thr Pro Lys Thr Gly Arg Lys
        35                  40

<210> SEQ ID NO 417
<211> LENGTH: 42
<212> TYPE: PRT
<213> ORGANISM: Artificial sequence
<220> FEATURE:
<223> OTHER INFORMATION: Odk2 variant

<400> SEQUENCE: 417

Gly Val Pro Thr Asp Val Lys Cys Arg Ile Ser Arg Gln Cys Glu Lys
1               5                   10                  15

Pro Cys Lys Asp Ala Gly Met Arg Phe Gly Lys Cys Met Asn Gly Lys
            20                  25                  30

Cys His Cys Thr Pro Lys Ala Arg Arg Asn
        35                  40

<210> SEQ ID NO 418
<211> LENGTH: 575
<212> TYPE: PRT
<213> ORGANISM: Homo sapiens

<400> SEQUENCE: 418

Met Asp Glu Arg Leu Ser Leu Leu Arg Ser Pro Pro Pro Ser Ala
1               5                   10                  15

Arg His Arg Ala His Pro Pro Gln Arg Pro Ala Ser Ser Gly Gly Ala
            20                  25                  30

His Thr Leu Val Asn His Gly Tyr Ala Glu Pro Ala Ala Gly Arg Glu
        35                  40                  45

Leu Pro Pro Asp Met Thr Val Val Pro Gly Asp His Leu Leu Glu Pro
    50                  55                  60

Glu Val Ala Asp Gly Gly Ala Pro Pro Gln Gly Gly Cys Gly Gly
65                  70                  75                  80

Gly Gly Cys Asp Arg Tyr Glu Pro Leu Pro Ser Leu Pro Ala Ala
                85                  90                  95

Gly Glu Gln Asp Cys Cys Gly Glu Arg Val Val Ile Asn Ile Ser Gly
            100                 105                 110

Leu Arg Phe Glu Thr Gln Leu Lys Thr Leu Cys Gln Phe Pro Glu Thr
        115                 120                 125

Leu Leu Gly Asp Pro Lys Arg Arg Met Arg Tyr Phe Asp Pro Leu Arg
    130                 135                 140

Asn Glu Tyr Phe Phe Asp Arg Asn Arg Pro Ser Phe Asp Ala Ile Leu
145                 150                 155                 160

Tyr Tyr Tyr Gln Ser Gly Gly Arg Ile Arg Arg Pro Val Asn Val Pro
                165                 170                 175

Ile Asp Ile Phe Ser Glu Glu Ile Arg Phe Tyr Gln Leu Gly Glu Glu
            180                 185                 190

Ala Met Glu Lys Phe Arg Glu Asp Glu Gly Phe Leu Arg Glu Glu Glu
        195                 200                 205

Arg Pro Leu Pro Arg Arg Asp Phe Gln Arg Gln Val Trp Leu Leu Phe
    210                 215                 220

-continued

Glu Tyr Pro Glu Ser Ser Gly Pro Ala Arg Gly Ile Ala Ile Val Ser
225                 230                 235                 240

Val Leu Val Ile Leu Ile Ser Ile Val Ile Phe Cys Leu Glu Thr Leu
            245                 250                 255

Pro Glu Phe Arg Asp Glu Lys Asp Tyr Pro Ala Ser Thr Ser Gln Asp
        260                 265                 270

Ser Phe Glu Ala Ala Gly Asn Ser Thr Ser Gly Ser Arg Ala Gly Ala
    275                 280                 285

Ser Ser Phe Ser Asp Pro Phe Val Val Glu Thr Leu Cys Ile Ile
290                 295                 300

Trp Phe Ser Phe Glu Leu Leu Val Arg Phe Phe Ala Cys Pro Ser Lys
305                 310                 315                 320

Ala Thr Phe Ser Arg Asn Ile Met Asn Leu Ile Asp Ile Val Ala Ile
                325                 330                 335

Ile Pro Tyr Phe Ile Thr Leu Gly Thr Glu Leu Ala Glu Arg Gln Gly
            340                 345                 350

Asn Gly Gln Gln Ala Met Ser Leu Ala Ile Leu Arg Val Ile Arg Leu
    355                 360                 365

Val Arg Val Phe Arg Ile Phe Lys Leu Ser Arg His Ser Lys Gly Leu
370                 375                 380

Gln Ile Leu Gly Gln Thr Leu Lys Ala Ser Met Arg Glu Leu Gly Leu
385                 390                 395                 400

Leu Ile Phe Phe Leu Phe Ile Gly Val Ile Leu Phe Ser Ser Ala Val
                405                 410                 415

Tyr Phe Ala Glu Ala Asp Asp Pro Thr Ser Gly Phe Ser Ser Ile Pro
        420                 425                 430

Asp Ala Phe Trp Trp Ala Val Val Thr Met Thr Thr Val Gly Tyr Gly
    435                 440                 445

Asp Met His Pro Val Thr Ile Gly Gly Lys Ile Val Gly Ser Leu Cys
450                 455                 460

Ala Ile Ala Gly Val Leu Thr Ile Ala Leu Pro Val Pro Val Ile Val
465                 470                 475                 480

Ser Asn Phe Asn Tyr Phe Tyr His Arg Glu Thr Glu Gly Glu Glu Gln
                485                 490                 495

Ser Gln Tyr Met His Val Gly Ser Cys Gln His Leu Ser Ser Ala
        500                 505                 510

Glu Glu Leu Arg Lys Ala Arg Ser Asn Ser Thr Leu Ser Lys Ser Glu
    515                 520                 525

Tyr Met Val Ile Glu Gly Gly Met Asn His Ser Ala Phe Pro Gln
530                 535                 540

Thr Pro Phe Lys Thr Gly Asn Ser Thr Ala Thr Cys Thr Thr Asn Asn
545                 550                 555                 560

Asn Pro Asn Ser Cys Val Asn Ile Lys Lys Ile Phe Thr Asp Val
                565                 570                 575

<210> SEQ ID NO 419
<211> LENGTH: 499
<212> TYPE: PRT
<213> ORGANISM: Homo sapiens

<400> SEQUENCE: 419

Met Thr Val Ala Thr Gly Asp Pro Ala Asp Glu Ala Ala Ala Leu Pro
1               5                   10                  15

Gly His Pro Gln Asp Thr Tyr Asp Pro Glu Ala Asp His Glu Cys Cys
            20                  25                  30

```
Glu Arg Val Val Ile Asn Ile Ser Gly Leu Arg Phe Glu Thr Gln Leu
             35                  40                  45

Lys Thr Leu Ala Gln Phe Pro Glu Thr Leu Leu Gly Asp Pro Lys Lys
 50                  55                  60

Arg Met Arg Tyr Phe Asp Pro Leu Arg Asn Glu Tyr Phe Phe Asp Arg
 65                  70                  75                  80

Asn Arg Pro Ser Phe Asp Ala Ile Leu Tyr Tyr Tyr Gln Ser Gly Gly
                 85                  90                  95

Arg Leu Arg Arg Pro Val Asn Val Pro Leu Asp Ile Phe Ser Glu Glu
            100                 105                 110

Ile Arg Phe Tyr Glu Leu Gly Glu Glu Ala Met Glu Met Phe Arg Glu
            115                 120                 125

Asp Glu Gly Tyr Ile Lys Glu Glu Arg Pro Leu Pro Glu Asn Glu
            130                 135                 140

Phe Gln Arg Gln Val Trp Leu Leu Phe Glu Tyr Pro Glu Ser Ser Gly
145                 150                 155                 160

Pro Ala Arg Ile Ile Ala Ile Val Ser Val Met Val Ile Leu Ile Ser
                165                 170                 175

Ile Val Ser Phe Cys Leu Glu Thr Leu Pro Ile Phe Arg Asp Glu Asn
            180                 185                 190

Glu Asp Met His Gly Ser Gly Val Thr Phe His Thr Tyr Ser Asn Ser
            195                 200                 205

Thr Ile Gly Tyr Gln Gln Ser Thr Ser Phe Thr Asp Pro Phe Phe Ile
            210                 215                 220

Val Glu Thr Leu Cys Ile Ile Trp Phe Ser Phe Glu Phe Leu Val Arg
225                 230                 235                 240

Phe Phe Ala Cys Pro Ser Lys Ala Gly Phe Phe Thr Asn Ile Met Asn
                245                 250                 255

Ile Ile Asp Ile Val Ala Ile Ile Pro Tyr Phe Ile Thr Leu Gly Thr
            260                 265                 270

Glu Leu Ala Glu Lys Pro Glu Asp Ala Gln Gln Gly Gln Gln Ala Met
            275                 280                 285

Ser Leu Ala Ile Leu Arg Val Ile Arg Leu Val Arg Val Phe Arg Ile
290                 295                 300

Phe Lys Leu Ser Arg His Ser Lys Gly Leu Gln Ile Leu Gly Gln Thr
305                 310                 315                 320

Leu Lys Ala Ser Met Arg Glu Leu Gly Leu Leu Ile Phe Phe Leu Phe
                325                 330                 335

Ile Gly Val Ile Leu Phe Ser Ser Ala Val Tyr Phe Ala Glu Ala Asp
            340                 345                 350

Glu Arg Glu Ser Gln Phe Pro Ser Ile Pro Asp Ala Phe Trp Trp Ala
            355                 360                 365

Val Val Ser Met Thr Thr Val Gly Tyr Gly Asp Met Val Pro Thr Thr
370                 375                 380

Ile Gly Gly Lys Ile Val Gly Ser Leu Cys Ala Ile Ala Gly Val Leu
385                 390                 395                 400

Thr Ile Ala Leu Pro Val Pro Val Ile Val Ser Asn Phe Asn Tyr Phe
                405                 410                 415

Tyr His Arg Glu Thr Glu Gly Glu Glu Gln Ala Gln Tyr Leu Gln Val
            420                 425                 430

Thr Ser Cys Pro Lys Ile Pro Ser Ser Pro Asp Leu Lys Lys Ser Arg
            435                 440                 445
```

```
Ser Ala Ser Thr Ile Ser Lys Ser Asp Tyr Met Glu Ile Gln Glu Gly
    450             455                 460

Val Asn Asn Ser Asn Glu Asp Phe Arg Glu Glu Asn Leu Lys Thr Ala
465             470                 475                 480

Asn Cys Thr Leu Ala Asn Thr Asn Tyr Val Asn Ile Thr Lys Met Leu
                485                 490                 495

Thr Asp Val

<210> SEQ ID NO 420
<211> LENGTH: 495
<212> TYPE: PRT
<213> ORGANISM: Homo sapiens

<400> SEQUENCE: 420

Met Thr Val Met Ser Gly Glu Asn Val Asp Glu Ala Ser Ala Ala Pro
1               5                   10                  15

Gly His Pro Gln Asp Gly Ser Tyr Pro Arg Gln Ala Asp His Asp Asp
                20                  25                  30

His Glu Cys Cys Glu Arg Val Val Ile Asn Ile Ser Gly Leu Arg Phe
            35                  40                  45

Glu Thr Gln Leu Lys Thr Leu Ala Gln Phe Pro Asn Thr Leu Leu Gly
    50                  55                  60

Asn Pro Lys Lys Arg Met Arg Tyr Phe Asp Pro Leu Arg Asn Glu Tyr
65              70                  75                  80

Phe Phe Asp Arg Asn Arg Pro Ser Phe Asp Ala Ile Leu Tyr Tyr Tyr
                85                  90                  95

Gln Ser Gly Gly Arg Leu Arg Arg Pro Val Asn Val Pro Leu Asp Met
            100                 105                 110

Phe Ser Glu Glu Ile Lys Phe Tyr Glu Leu Gly Glu Glu Ala Met Glu
    115                 120                 125

Lys Phe Arg Glu Asp Glu Gly Phe Ile Lys Glu Glu Glu Arg Pro Leu
130                 135                 140

Pro Glu Lys Glu Tyr Gln Arg Gln Val Trp Leu Leu Phe Glu Tyr Pro
145                 150                 155                 160

Glu Ser Ser Gly Pro Ala Arg Val Ile Ala Ile Val Ser Val Met Val
                165                 170                 175

Ile Leu Ile Ser Ile Val Ile Phe Cys Leu Glu Thr Leu Pro Glu Leu
            180                 185                 190

Lys Asp Asp Lys Asp Phe Thr Gly Thr Val His Arg Ile Asp Asn Thr
    195                 200                 205

Thr Val Ile Tyr Asn Ser Asn Ile Phe Thr Asp Pro Phe Phe Ile Val
210                 215                 220

Glu Thr Leu Cys Ile Ile Trp Phe Ser Phe Glu Leu Val Val Arg Phe
225                 230                 235                 240

Phe Ala Cys Pro Ser Lys Thr Asp Phe Lys Asn Ile Met Asn Phe
                245                 250                 255

Ile Asp Ile Val Ala Ile Ile Pro Tyr Phe Ile Thr Leu Gly Thr Glu
            260                 265                 270

Ile Ala Glu Gln Glu Gly Asn Gln Lys Gly Glu Gln Ala Thr Ser Leu
    275                 280                 285

Ala Ile Leu Arg Val Ile Arg Leu Val Arg Val Phe Arg Ile Phe Lys
290                 295                 300

Leu Ser Arg His Ser Lys Gly Leu Gln Ile Leu Gly Gln Thr Leu Lys
305                 310                 315                 320
```

```
Ala Ser Met Arg Glu Leu Gly Leu Leu Ile Phe Phe Leu Phe Ile Gly
            325                 330                 335

Val Ile Leu Phe Ser Ala Val Tyr Phe Ala Glu Ala Glu Ala
        340                 345                 350

Glu Ser His Phe Ser Ser Ile Pro Asp Ala Phe Trp Trp Ala Val Val
            355                 360                 365

Ser Met Thr Thr Val Gly Tyr Gly Asp Met Tyr Pro Val Thr Ile Gly
    370                 375                 380

Gly Lys Ile Val Gly Ser Leu Cys Ala Ile Ala Gly Val Leu Thr Ile
385                 390                 395                 400

Ala Leu Pro Val Pro Val Ile Val Ser Asn Phe Asn Tyr Phe Tyr His
                405                 410                 415

Arg Glu Thr Glu Gly Glu Glu Gln Ala Gln Leu Leu His Val Ser Ser
            420                 425                 430

Pro Asn Leu Ala Ser Asp Ser Asp Leu Ser Arg Arg Ser Ser Ser Thr
            435                 440                 445

Met Ser Lys Ser Glu Tyr Met Glu Ile Glu Glu Asp Met Asn Asn Ser
    450                 455                 460

Ile Ala His Tyr Arg Gln Val Asn Ile Arg Thr Ala Asn Cys Thr Thr
465                 470                 475                 480

Ala Asn Gln Asn Cys Val Asn Lys Ser Lys Leu Leu Thr Asp Val
                485                 490                 495

<210> SEQ ID NO 421
<211> LENGTH: 613
<212> TYPE: PRT
<213> ORGANISM: Homo sapiens

<400> SEQUENCE: 421

Met Glu Ile Ala Leu Val Pro Leu Glu Asn Gly Gly Ala Met Thr Val
1               5                   10                  15

Arg Gly Gly Asp Glu Ala Arg Ala Gly Cys Gly Gln Ala Thr Gly Gly
            20                  25                  30

Glu Leu Gln Cys Pro Pro Thr Ala Gly Leu Ser Asp Gly Pro Lys Glu
        35                  40                  45

Pro Ala Pro Lys Gly Arg Gly Ala Gln Arg Asp Ala Asp Ser Gly Val
    50                  55                  60

Arg Pro Leu Pro Pro Leu Pro Asp Pro Gly Val Arg Pro Leu Pro Pro
65                  70                  75                  80

Leu Pro Glu Glu Leu Pro Arg Pro Arg Arg Pro Pro Glu Asp Glu
                85                  90                  95

Glu Glu Glu Gly Asp Pro Gly Leu Gly Thr Val Glu Asp Gln Ala Leu
            100                 105                 110

Gly Thr Ala Ser Leu His His Gln Arg Val His Ile Asn Ile Ser Gly
        115                 120                 125

Leu Arg Phe Glu Thr Gln Leu Gly Thr Leu Ala Gln Phe Pro Asn Thr
    130                 135                 140

Leu Leu Gly Asp Pro Ala Lys Arg Leu Arg Tyr Phe Asp Pro Leu Arg
145                 150                 155                 160

Asn Glu Tyr Phe Phe Asp Arg Asn Arg Pro Ser Phe Gly Ile Leu
                165                 170                 175

Tyr Tyr Tyr Gln Ser Gly Gly Arg Leu Arg Arg Pro Val Asn Val Ser
            180                 185                 190

Leu Asp Val Phe Ala Asp Glu Ile Arg Phe Tyr Gln Leu Gly Asp Glu
        195                 200                 205
```

```
Ala Met Glu Arg Phe Arg Glu Asp Glu Gly Phe Ile Lys Glu Glu
    210                 215                 220

Lys Pro Leu Pro Arg Asn Glu Phe Gln Arg Gln Val Trp Leu Ile Phe
225             230                 235                 240

Glu Tyr Pro Glu Ser Ser Gly Ser Ala Arg Ala Ile Ala Ile Val Ser
                245                 250                 255

Val Leu Val Ile Leu Ile Ser Ile Ile Thr Phe Cys Leu Glu Thr Leu
            260                 265                 270

Pro Glu Phe Arg Asp Glu Arg Glu Leu Leu Arg His Pro Ala Pro
        275                 280                 285

His Gln Pro Pro Ala Pro Ala Pro Gly Ala Asn Gly Ser Gly Val Met
    290                 295                 300

Ala Pro Pro Ser Gly Pro Thr Val Ala Pro Leu Leu Pro Arg Thr Leu
305             310                 315                 320

Ala Asp Pro Phe Phe Ile Val Glu Thr Thr Cys Val Ile Trp Phe Thr
                325                 330                 335

Phe Glu Leu Leu Val Arg Phe Phe Ala Cys Pro Ser Lys Ala Gly Phe
            340                 345                 350

Ser Arg Asn Ile Met Asn Ile Ile Asp Val Val Ala Ile Phe Pro Tyr
        355                 360                 365

Phe Ile Thr Leu Gly Thr Glu Leu Ala Glu Gln Gln Pro Gly Gly Gly
    370                 375                 380

Gly Gly Gly Gln Asn Gly Gln Gln Ala Met Ser Leu Ala Ile Leu Arg
385             390                 395                 400

Val Ile Arg Leu Val Arg Val Phe Arg Ile Phe Lys Leu Ser Arg His
                405                 410                 415

Ser Lys Gly Leu Gln Ile Leu Gly Lys Thr Leu Gln Ala Ser Met Arg
            420                 425                 430

Glu Leu Gly Leu Leu Ile Phe Phe Leu Phe Ile Gly Val Ile Leu Phe
        435                 440                 445

Ser Ser Ala Val Tyr Phe Ala Glu Ala Asp Asn Gln Gly Thr His Phe
    450                 455                 460

Ser Ser Ile Pro Asp Ala Phe Trp Trp Ala Val Val Thr Met Thr Thr
465             470                 475                 480

Val Gly Tyr Gly Asp Met Arg Pro Ile Thr Val Gly Gly Lys Ile Val
                485                 490                 495

Gly Ser Leu Cys Ala Ile Ala Gly Val Leu Thr Ile Ala Leu Pro Val
            500                 505                 510

Pro Val Ile Val Ser Asn Phe Asn Tyr Phe Tyr His Arg Glu Thr Asp
        515                 520                 525

His Glu Glu Pro Ala Val Leu Lys Glu Glu Gly Thr Gln Ser Gln
    530                 535                 540

Gly Pro Gly Leu Asp Arg Gly Val Gln Arg Lys Val Ser Gly Ser Arg
545             550                 555                 560

Gly Ser Phe Cys Lys Ala Gly Gly Thr Leu Glu Asn Ala Asp Ser Ala
                565                 570                 575

Arg Arg Gly Ser Cys Pro Leu Glu Lys Cys Asn Val Lys Ala Lys Ser
            580                 585                 590

Asn Val Asp Leu Arg Arg Ser Leu Tyr Ala Leu Cys Leu Asp Thr Ser
        595                 600                 605

Arg Glu Thr Asp Leu
    610
```

<210> SEQ ID NO 422
<211> LENGTH: 525
<212> TYPE: PRT
<213> ORGANISM: Rattus norvegius

<400> SEQUENCE: 422

```
Met Thr Val Val Pro Gly Asp His Leu Leu Glu Pro Glu Ala Ala Gly
1               5                   10                  15

Gly Gly Gly Gly Asp Pro Pro Gln Gly Gly Cys Val Ser Gly Gly Gly
            20                  25                  30

Cys Asp Arg Tyr Glu Pro Leu Pro Ala Leu Pro Ala Ala Gly Glu
        35                  40                  45

Gln Asp Cys Cys Gly Glu Arg Val Val Ile Asn Ile Ser Gly Leu Arg
50                  55                  60

Phe Glu Thr Gln Leu Lys Thr Leu Cys Gln Phe Pro Glu Thr Leu Leu
65                  70                  75                  80

Gly Asp Pro Lys Arg Arg Met Arg Tyr Phe Asp Pro Leu Arg Asn Glu
                85                  90                  95

Tyr Phe Phe Asp Arg Asn Arg Pro Ser Phe Asp Ala Ile Leu Tyr Tyr
            100                 105                 110

Tyr Gln Ser Gly Gly Arg Ile Arg Arg Pro Val Asn Val Pro Ile Asp
        115                 120                 125

Ile Phe Ser Glu Glu Ile Arg Phe Tyr Gln Leu Gly Glu Glu Ala Met
130                 135                 140

Glu Lys Phe Arg Glu Asp Glu Gly Phe Leu Arg Glu Glu Glu Arg Pro
145                 150                 155                 160

Leu Pro Arg Arg Asp Phe Gln Arg Gln Val Trp Leu Leu Phe Glu Tyr
                165                 170                 175

Pro Glu Ser Ser Gly Pro Ala Arg Gly Ile Ala Ile Val Ser Val Leu
            180                 185                 190

Val Ile Leu Ile Ser Ile Val Ile Phe Cys Leu Glu Thr Leu Pro Glu
        195                 200                 205

Phe Arg Asp Glu Lys Asp Tyr Pro Ala Ser Pro Ser Gln Asp Val Phe
210                 215                 220

Glu Ala Ala Asn Asn Ser Thr Ser Gly Ala Ser Ser Gly Ala Ser Ser
225                 230                 235                 240

Phe Ser Asp Pro Phe Phe Val Val Glu Thr Leu Cys Ile Ile Trp Phe
                245                 250                 255

Ser Phe Glu Leu Leu Val Arg Phe Phe Ala Cys Pro Ser Lys Ala Thr
            260                 265                 270

Phe Ser Arg Asn Ile Met Asn Leu Ile Asp Ile Val Ala Ile Ile Pro
        275                 280                 285

Tyr Phe Ile Thr Leu Gly Thr Glu Leu Ala Glu Arg Gln Gly Asn Gly
290                 295                 300

Gln Gln Ala Met Ser Leu Ala Ile Leu Arg Val Ile Arg Leu Val Arg
305                 310                 315                 320

Val Phe Arg Ile Phe Lys Leu Ser Arg His Ser Lys Gly Leu Gln Ile
                325                 330                 335

Leu Gly Gln Thr Leu Lys Ala Ser Met Arg Glu Leu Gly Leu Leu Ile
            340                 345                 350

Phe Phe Leu Phe Ile Gly Val Ile Leu Phe Ser Ser Ala Val Tyr Phe
        355                 360                 365

Ala Glu Ala Asp Asp Pro Ser Ser Gly Phe Asn Ser Ile Pro Asp Ala
370                 375                 380
```

```
Phe Trp Trp Ala Val Val Thr Met Thr Thr Val Gly Tyr Gly Asp Met
385                 390                 395                 400

His Pro Val Thr Ile Gly Gly Lys Ile Val Gly Ser Leu Cys Ala Ile
            405                 410                 415

Ala Gly Val Leu Thr Ile Ala Leu Pro Val Pro Val Ile Val Ser Asn
        420                 425                 430

Phe Asn Tyr Phe Tyr His Arg Glu Thr Glu Gly Glu Glu Gln Ala Gln
        435                 440                 445

Tyr Met His Val Gly Ser Cys Gln His Leu Ser Ser Ser Ala Glu Glu
    450                 455                 460

Leu Arg Lys Ala Arg Ser Asn Ser Thr Leu Lys Ser Glu Tyr Met
465                 470                 475                 480

Val Ile Glu Glu Gly Gly Met Asn His Ser Ala Phe Pro Gln Thr Pro
            485                 490                 495

Phe Lys Thr Gly Asn Ser Thr Ala Thr Cys Thr Thr Asn Asn Asn Pro
            500                 505                 510

Asn Ser Cys Val Asn Ile Lys Lys Ile Phe Thr Asp Val
            515                 520                 525

<210> SEQ ID NO 423
<211> LENGTH: 495
<212> TYPE: PRT
<213> ORGANISM: Rattus norvegius

<400> SEQUENCE: 423

Met Thr Val Met Ser Gly Glu Asn Ala Asp Glu Ala Ser Ala Ala Pro
1               5                   10                  15

Gly His Pro Gln Asp Gly Ser Tyr Pro Arg Gln Ala Asp His Asp Asp
            20                  25                  30

His Glu Cys Cys Glu Arg Val Val Ile Asn Ile Ser Gly Leu Arg Phe
        35                  40                  45

Glu Thr Gln Leu Lys Thr Leu Ala Gln Phe Pro Asn Thr Leu Leu Gly
    50                  55                  60

Asn Pro Lys Lys Arg Met Arg Tyr Phe Asp Pro Leu Arg Asn Glu Tyr
65                  70                  75                  80

Phe Phe Asp Arg Asn Arg Pro Ser Phe Asp Ala Ile Leu Tyr Tyr Tyr
            85                  90                  95

Gln Ser Gly Gly Arg Leu Arg Arg Pro Val Asn Val Pro Leu Asp Met
            100                 105                 110

Phe Ser Glu Glu Ile Lys Phe Tyr Glu Leu Gly Glu Glu Ala Met Glu
        115                 120                 125

Lys Phe Arg Glu Asp Glu Gly Phe Ile Lys Glu Glu Glu Arg Pro Leu
    130                 135                 140

Pro Glu Lys Glu Tyr Gln Arg Gln Val Trp Leu Leu Phe Glu Tyr Pro
145                 150                 155                 160

Glu Ser Ser Gly Pro Ala Arg Val Ile Ala Ile Val Ser Val Met Val
            165                 170                 175

Ile Leu Ile Ser Ile Val Ile Phe Cys Leu Glu Thr Leu Pro Glu Leu
        180                 185                 190

Lys Asp Asp Lys Asp Phe Thr Gly Thr Ile His Arg Ile Asp Asn Thr
    195                 200                 205

Thr Val Ile Tyr Thr Ser Asn Ile Phe Thr Asp Pro Phe Phe Ile Val
210                 215                 220

Glu Thr Leu Cys Ile Ile Trp Phe Ser Phe Glu Leu Val Val Arg Phe
```

```
            225                 230                 235                 240
        Phe Ala Cys Pro Ser Lys Thr Asp Phe Phe Lys Asn Ile Met Asn Phe
                        245                 250                 255

Ile Asp Ile Val Ala Ile Ile Pro Tyr Phe Ile Thr Leu Gly Thr Glu
                        260                 265                 270

Ile Ala Glu Gln Glu Gly Asn Gln Lys Gly Glu Gln Ala Thr Ser Leu
                        275                 280                 285

Ala Ile Leu Arg Val Ile Arg Leu Val Arg Val Phe Arg Ile Phe Lys
                        290                 295                 300

Leu Ser Arg His Ser Lys Gly Leu Gln Ile Leu Gly Gln Thr Leu Lys
        305                 310                 315                 320

Ala Ser Met Arg Glu Leu Gly Leu Leu Ile Phe Phe Leu Phe Ile Gly
                        325                 330                 335

Val Ile Leu Phe Ser Ser Ala Val Tyr Phe Ala Glu Ala Glu Glu Ala
                        340                 345                 350

Glu Ser His Phe Ser Ser Ile Pro Asp Ala Phe Trp Trp Ala Val Val
                        355                 360                 365

Ser Met Thr Thr Val Gly Tyr Gly Asp Met Tyr Pro Val Thr Ile Gly
        370                 375                 380

Gly Lys Ile Val Gly Ser Leu Cys Ala Ile Ala Gly Val Leu Thr Ile
        385                 390                 395                 400

Ala Leu Pro Val Pro Val Ile Val Ser Asn Phe Asn Tyr Phe Tyr His
                        405                 410                 415

Arg Glu Thr Glu Gly Glu Glu Gln Ala Gln Leu Leu His Val Ser Ser
                        420                 425                 430

Pro Asn Leu Ala Ser Asp Ser Asp Leu Ser Arg Arg Ser Ser Ser Thr
                        435                 440                 445

Ile Ser Lys Ser Glu Tyr Met Glu Ile Glu Glu Asp Met Asn Asn Ser
                        450                 455                 460

Ile Ala His Tyr Arg Gln Ala Asn Ile Arg Thr Gly Asn Cys Thr Ala
        465                 470                 475                 480

Thr Asp Gln Asn Cys Val Asn Lys Ser Lys Leu Leu Thr Asp Val
                        485                 490                 495

<210> SEQ ID NO 424
<211> LENGTH: 575
<212> TYPE: PRT
<213> ORGANISM: Papio cynocephalus

<400> SEQUENCE: 424

Met Asp Glu His Leu Ser Leu Leu Arg Ser Pro Pro Pro Ser Ala
        1               5                   10                  15

Arg His Arg Ala His Pro Ala Gln Arg Pro Ala Ser Ser Gly Gly Ala
                        20                  25                  30

His Thr Leu Val Asn Pro Gly Tyr Ala Glu Pro Ala Ala Gly Pro Glu
                        35                  40                  45

Leu Pro Pro Asp Met Thr Val Val Pro Gly Asp His Leu Leu Glu Pro
                        50                  55                  60

Glu Val Ala Asp Gly Gly Ala Pro Gln Gly Gly Cys Gly Gly
        65                  70                  75                  80

Gly Gly Cys Asp Arg Tyr Glu Pro Leu Pro Pro Ser Leu Pro Ala Ala
                        85                  90                  95

Gly Glu Gln Asp Cys Cys Gly Glu Arg Val Val Ile Asn Ile Ser Gly
                        100                 105                 110
```

Leu Arg Phe Glu Thr Gln Leu Lys Thr Leu Cys Gln Phe Pro Glu Thr
115                 120                 125

Leu Leu Gly Asp Pro Lys Arg Arg Met Arg Tyr Phe Asp Pro Leu Arg
    130                 135                 140

Asn Glu Tyr Phe Phe Asp Arg Asn Arg Pro Ser Phe Asp Ala Ile Leu
145                 150                 155                 160

Tyr Tyr Tyr Gln Ser Gly Arg Ile Arg Arg Pro Val Asn Val Pro
            165                 170                 175

Ile Asp Ile Phe Ser Glu Ile Arg Phe Tyr Gln Leu Gly Glu Glu
                180                 185                 190

Ala Met Glu Lys Phe Arg Glu Asp Gly Phe Leu Arg Glu Glu
                195                 200                 205

Arg Pro Leu Pro Arg Arg Asp Phe Gln Arg Gln Val Trp Leu Leu Phe
    210                 215                 220

Glu Tyr Pro Glu Ser Ser Gly Pro Ala Arg Gly Ile Ala Ile Val Ser
225                 230                 235                 240

Val Leu Val Ile Leu Ile Ser Ile Val Ile Phe Cys Leu Glu Thr Leu
                245                 250                 255

Pro Glu Phe Arg Asp Glu Lys Asp Tyr Pro Ala Ser Pro Ser Gln Asp
            260                 265                 270

Ser Phe Asp Ala Ala Gly Asn Ser Thr Ser Gly Ala Ala Ala Gly Ala
    275                 280                 285

Ser Ser Phe Ser Asp Pro Phe Phe Val Val Glu Thr Leu Cys Ile Ile
    290                 295                 300

Trp Phe Ser Phe Glu Leu Leu Val Arg Phe Phe Ala Cys Pro Ser Lys
305                 310                 315                 320

Ala Thr Phe Ser Arg Asn Ile Met Asn Leu Ile Asp Ile Val Ala Ile
                325                 330                 335

Ile Pro Tyr Phe Ile Thr Leu Gly Thr Glu Leu Ala Glu Arg Gln Gly
            340                 345                 350

Asn Gly Gln Gln Ala Met Ser Leu Ala Ile Leu Arg Val Ile Arg Leu
    355                 360                 365

Val Arg Val Phe Arg Ile Phe Lys Leu Ser Arg His Ser Lys Gly Leu
370                 375                 380

Gln Ile Leu Gly Gln Thr Leu Lys Ala Ser Met Arg Glu Leu Gly Leu
385                 390                 395                 400

Leu Ile Phe Phe Leu Phe Ile Gly Val Ile Leu Phe Ser Ser Ala Val
            405                 410                 415

Tyr Phe Ala Glu Ala Asp Asp Pro Thr Ser Gly Phe Ser Ser Ile Pro
            420                 425                 430

Asp Ala Phe Trp Trp Ala Val Val Thr Met Thr Thr Val Gly Tyr Gly
            435                 440                 445

Asp Met His Pro Val Thr Ile Gly Gly Lys Ile Val Gly Ser Leu Cys
            450                 455                 460

Ala Ile Ala Gly Val Leu Thr Ile Ala Leu Pro Val Pro Val Ile Val
465                 470                 475                 480

Ser Asn Phe Asn Tyr Phe Tyr His Arg Glu Thr Glu Gly Glu Glu Gln
            485                 490                 495

Ala Gln Tyr Met His Val Gly Ser Cys Gln His Leu Ser Ser Ala
            500                 505                 510

Glu Glu Leu Arg Lys Ala Arg Ser Asn Ser Thr Leu Ser Lys Ser Glu
            515                 520                 525

Tyr Met Val Ile Glu Glu Gly Gly Met Asn His Ser Ala Phe Pro Gln

```
               530                 535                 540

Thr Pro Phe Lys Thr Gly Asn Ser Thr Ala Thr Cys Thr Thr Asn Asn
545                 550                 555                 560

Asn Pro Asn Ser Cys Val Asn Ile Lys Lys Ile Phe Thr Asp Val
                565                 570                 575

<210> SEQ ID NO 425
<211> LENGTH: 282
<212> TYPE: PRT
<213> ORGANISM: Artificial sequence
<220> FEATURE:
<223> OTHER INFORMATION: Odk2 fusion protein

<400> SEQUENCE: 425

Gly Val Pro Thr Asp Val Lys Cys Arg Gly Ser Pro Gln Cys Ile Gln
1               5                   10                  15

Pro Cys Lys Asp Ala Gly Met Arg Phe Gly Lys Cys Met Asn Gly Lys
                20                  25                  30

Cys His Cys Thr Pro Lys Gly Ser Gly Gly Gly Ser Gly Gly Gly
            35                  40                  45

Gly Ser Gly Gly Gly Ser Gly Gly Gly Ser Cys Pro Pro Cys
50                  55                  60

Pro Ala Pro Glu Ala Ala Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser Gln Glu Asp Pro Glu Val Gln Phe Asn Trp
            100                 105                 110

Tyr Val Asp Gly Val Glu Val His Asn Ala Lys Thr Lys Pro Arg Glu
        115                 120                 125

Glu Gln Phe Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Gly Leu Pro Ser Ser Ile Glu Lys Thr Ile Ser Lys Ala Lys Gly
                165                 170                 175

Gln Pro Arg Glu Pro Gln Val Tyr Thr Leu Pro Pro Ser Gln Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Arg Leu Thr Val Asp Lys Ser Arg Trp Gln Glu Gly Asn
                245                 250                 255

Val Phe Ser Cys Ser Val Met His Glu Ala Leu His Asn His Tyr Thr
            260                 265                 270

Gln Lys Ser Leu Ser Leu Ser Leu Gly Lys
        275                 280

<210> SEQ ID NO 426
<211> LENGTH: 48
<212> TYPE: PRT
<213> ORGANISM: Artificial sequence
<220> FEATURE:
<223> OTHER INFORMATION: Odk2 variant
```

```
<220> FEATURE:
<221> NAME/KEY: VARIANT
<222> LOCATION: (4)..(4)
<223> OTHER INFORMATION: Xaa may be Ile, Thr, Qln or Glu
<220> FEATURE:
<221> NAME/KEY: VARIANT
<222> LOCATION: (7)..(7)
<223> OTHER INFORMATION: Xaa may be Asn or Asp
<220> FEATURE:
<221> NAME/KEY: VARIANT
<222> LOCATION: (13)..(13)
<223> OTHER INFORMATION: Xaa may be Lys, Arg, Glu, Ala or Qln
<220> FEATURE:
<221> NAME/KEY: VARIANT
<222> LOCATION: (21)..(21)
<223> OTHER INFORMATION: Xaa may be Ile, Glu, Leu, Asp, Qln, His, val,
      Lys or Ala
<220> FEATURE:
<221> NAME/KEY: VARIANT
<222> LOCATION: (24)..(24)
<223> OTHER INFORMATION: Xaa may be Glu, Lys, Leu, Qln, Asp, Val or His

<400> SEQUENCE: 426

Gly Val Pro Xaa Ala Ala Xaa Ala Ala Val Lys Cys Xaa Ala Ala Ile
1               5                   10                  15

Ser Arg Gln Cys Xaa Ala Ala Xaa Ala Ala Pro Cys Lys Asp Ala Gly
            20                  25                  30

Met Arg Phe Gly Lys Cys Met Asn Gly Lys Cys His Cys Thr Pro Lys
        35                  40                  45

<210> SEQ ID NO 427
<211> LENGTH: 48
<212> TYPE: PRT
<213> ORGANISM: Artificial sequence
<220> FEATURE:
<223> OTHER INFORMATION: Odk2 variant
<220> FEATURE:
<221> NAME/KEY: VARIANT
<222> LOCATION: (4)..(4)
<223> OTHER INFORMATION: Xaa may be Ile or Thr
<220> FEATURE:
<221> NAME/KEY: VARIANT
<222> LOCATION: (5)..(5)
<223> OTHER INFORMATION: Xaa may be Asn or Asp
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: Xaa may be Lys or Arg
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: VARIANT
<222> LOCATION: (15)..(15)
<223> OTHER INFORMATION: Xaa may be Ile or Glu
<220> FEATURE:
<221> NAME/KEY: VARIANT
<222> LOCATION: (16)..(16)
<223> OTHER INFORMATION: Xaa may be Glu or Lys
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 427
```

```
Gly Val Pro Xaa Ala Ala Xaa Ala Ala Val Lys Cys Xaa Ala Ala Ile
1               5               10                  15

Ser Arg Gln Cys Xaa Ala Ala Xaa Ala Ala Pro Cys Lys Asp Ala Gly
            20              25              30

Met Arg Phe Gly Lys Cys Met Asn Gly Lys Cys His Cys Thr Pro Lys
        35              40              45
```

<210> SEQ ID NO 428
<211> LENGTH: 44
<212> TYPE: PRT
<213> ORGANISM: Artificial sequence
<220> FEATURE:
<223> OTHER INFORMATION: Linker

<400> SEQUENCE: 428

```
Gly Ser Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro Ala Pro Ala Ser
        35                  40
```

<210> SEQ ID NO 429
<211> LENGTH: 114
<212> TYPE: DNA
<213> ORGANISM: Artificial sequence
<220> FEATURE:
<223> OTHER INFORMATION: peptide 261 cDNA

<400> SEQUENCE: 429
ggcgtgccta tcaacgtcaa gtgtaagatc tctcggcaat gtatcgagcc gtgcaaagat    60
gctggaatgc gcttcgggaa atgtatgaat ggcaagtgtc actgcacacc taag          114

<210> SEQ ID NO 430
<211> LENGTH: 114
<212> TYPE: DNA
<213> ORGANISM: Artificial sequence
<220> FEATURE:
<223> OTHER INFORMATION: Peptide p579 cDNA

<400> SEQUENCE: 430
ggcgtgccca ccgacgtgaa gtgccggatc agccggcagt gcgagaagcc ctgcaaggac    60
gccggcatgc ggttcggcaa gtgcatgaac ggcaagtgcc actgcacccc caag          114

<210> SEQ ID NO 431
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 431

```
Arg Asn Arg Glu
1
```

<210> SEQ ID NO 432
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 432

```
His His Arg Gln
1

<210> SEQ ID NO 433
<211> LENGTH: 4
<212> TYPE: PRT
<213> ORGANISM: Artificial sequence
<220> FEATURE:
<223> OTHER INFORMATION: C-terminal peptide extension

<400> SEQUENCE: 433

Thr Arg Ala Lys
1
```